US008022177B2

(12) United States Patent
Best et al.

(10) Patent No.: US 8,022,177 B2
(45) Date of Patent: Sep. 20, 2011

(54) PEPTIDES AND CALCIUM REGULATION IN MAMMALIAN CELLS

(75) Inventors: Philip M. Best, Urbana, IL (US); Janice Jones, Champaign, IL (US); Jared P. Hansen, Peoria, IL (US); Zuojun Lin, Urbana, IL (US); Karen E. Weis, Champaign, IL (US); Po-Ju Chu, Taipei (TW)

(73) Assignee: The Board of Trustees of the University of Illinois, Urbana, IL (US)

( * ) Notice: Subject to any disclaimer, the term of this patent is extended or adjusted under 35 U.S.C. 154(b) by 316 days.

(21) Appl. No.: 11/537,323

(22) Filed: Sep. 29, 2006

(65) Prior Publication Data

US 2007/0213267 A1  Sep. 13, 2007

Related U.S. Application Data

(60) Provisional application No. 60/722,707, filed on Sep. 30, 2005.

(51) Int. Cl.
*A61K 38/00* (2006.01)
*C07H 21/04* (2006.01)
*C12P 21/06* (2006.01)
*C12N 5/00* (2006.01)

(52) U.S. Cl. ..... 530/324; 514/12.1; 536/23.5; 435/69.1; 435/325

(58) Field of Classification Search .......................... None
See application file for complete search history.

(56) References Cited

U.S. PATENT DOCUMENTS

| 5,364,842 | A | 11/1994 | Justice et al. |
| 5,795,864 | A | 8/1998 | Amstutz et al. |
| 6,011,035 | A | 1/2000 | Snutch et al. |
| 6,267,945 | B1 | 7/2001 | Zamponi |
| 6,310,059 | B1 | 10/2001 | Snutch |
| 6,365,337 | B1 | 4/2002 | Letts et al. |
| 6,387,897 | B1 | 5/2002 | Snutch |
| 6,492,375 | B2 | 12/2002 | Snutch |
| 6,617,322 | B2 | 9/2003 | Snutch |
| 6,943,168 | B2 | 9/2005 | Snutch et al. |
| 6,949,554 | B2 | 9/2005 | Snutch et al. |
| 2004/0034035 | A1 | 2/2004 | Snutch et al. |
| 2004/0044004 | A1 | 3/2004 | Snutch et al. |
| 2005/0014748 | A1 | 1/2005 | Pajouhesh et al. |
| 2005/0203040 | A1 | 9/2005 | Richards et al. |
| 2005/0209179 | A1 | 9/2005 | McSwiggen et al. |
| 2005/0209180 | A1 | 9/2005 | Jadhav et al. |

OTHER PUBLICATIONS

Hansen et al Calcium channel c6 subunits are unique modulators of low voltage-activated (Cav3.1) calcium current.Journal of Molecular and Cellular Cardiology 37 (2004) 1147-1158.*
Ahern et al. (2001) "Modulation of L-Type Ca2+ Current but Not Activation of Ca2+ Release by the Gamma-1 Subunit of the Dihydropyridine Receptor of Skeletal Muscle," *BMC Physiol.* 1(1):8.
Arikkath et al. (2003) "Auxiliary Subunits: Essential Components of the Voltage-Gated Calcium Channel Complex," *Curr. Opin. Neurobiol.* 13(3):298-307.
Arikkath et al. (2003) "Gama 1 Subunit Interactions Within the Skeletal Muscle L-Type Voltage-Gated Calcium Channels," *J. Biol. Chem.* 278(2):1212-1219.
Bahinski et al. (1997) "Charged Amino Acids Near the Pore Entrance Influence Ion-Conduction of a Human L-Type Cardiac Calcium Channel," *Mol. Cell. Biochem.* 166(1-2):125-134.
Black et al. (1999) "Identification and Cloning of Putative Human Neuronal Voltage-Gated Calcium Channel Gamma-2 and Gamma-3 Subunits: Neurologic Implications," *Mayo Clin. Proc.* 74(4):357-361.
Burgess et al. (1999) "Identification of Three Novel Ca(2+) Channel Gamma Subunit Genes Reveals Molecular Diversification by Tandem and Chromosome Duplication," *Genome Res.* 9(12):1204-1213.
Burgess et al. (2001) "A Cluster of Three Novel Ca2+ Channel Gamma Subunit Genes on Chromosome 19q13.4: Evolution and Expression Profile of the Gamma Subunit Gene Family," *Genomics* 71(3):339-350.
Campbell et al. (1988) "Structural Characterization of the Nitrendiphine Receptor of the Voltage-Dependent Ca2+ Channel: Evidence for a 52,000 Da Subunit," *J. Cardiovasc. Pharmacol.* 12(4):S86-S90.
Catterall, W.A. (2000) "Structure and Regulation of Voltage-Gated Ca2+ Channels," *Ann. Rev. Cell. Dev. Biol.* 16:521-555.
Catterall, W.A. (1988) "Molecular Properties of Voltage-Sensitive Sodium and Calcium Channels," *Braz. J. Med. Biol. Res.* 21(6):1129-1144.
Chen et al. (2000) "Stargazin Regulates Synaptic Targeting of AMPA Receptors by Two Distinct Mechanisms," *Nature* 408:936-943.
Chu et al. (2001) "Calcium Channel Gamma Subunits Provide Insights into the Evolution of this Gene Family," *Gene* 280(1-2):37-48.
Claycomb et al. (1998) HL-1 Cells: A Cardiac Muscle Cell Line that Contracts and Retains Phenotypic Characteristics of the Adult Cardiomyocyte, *Proc. Nat. Acad. Sci. USA* 95(6):2979-2984.
Costagliola et al. (2002) "Tyrosine Sulfonation is Required for Agonist Recognition by Glycoprotein Hormone Receptors," *EMBO J.* 21(4):504-513.
Curtis et al. (1984) "Purification of the Calcium Antagonist Receptor of the Voltage-Sensitive Calcium Channel from Skeletal Muscle Transverse Tubules," *Biochem.* 23(10):2113-2118.
Curran et al. (2003) "Sequence Motifs, Polar Interactions and Conformational Changes in Helical Membrane Proteins," *Curr. Opin. Struct. Biol.* 13(4):412-417.

(Continued)

*Primary Examiner* — Manjunath Rao
*Assistant Examiner* — Kagnew H Gebreyesus
(74) *Attorney, Agent, or Firm* — Greenlee Sullivan P.C.

(57) ABSTRACT

Calcium channels in a variety of tissues may contain different subunits, including several different γ (gamma) subunits. We report studies regarding structural features of certain gamma subunits, for example the N-terminal first transmembrane domain (TM1) of the subunit γ6. We disclose that certain structural motifs, for example a GxxxG-like structural motif as described herein, can mediate subunit function for calcium channels. A particular peptide motif that has been identified as significant for the ability to mediate a decrease in calcium current is GxxxA. Compositions and methods are disclosed which are useful in modifying calcium regulation in mammalian cells. In various embodiments, calcium current is modified.

14 Claims, 38 Drawing Sheets

OTHER PUBLICATIONS

De Jongh et al. (1991) "Characterization of the Two Size Forms of the Alpha 1 Subunit of Skeletal Muscle L-Type Calcium Channels," *Proc. Nat. Acad. Sci USA* 88(23):10778-10782.

De Waard et al. (1996) "Structural and Functional Diversity of Voltage-Activated Calcium Channels," *Ion Channels* 4:41-87.

De Waard et al. (1994) "Ca2+ Channel Regulation by a Conserved Beta Subunit Domain," *Neuron.* 13(2):495-503.

De Waard et al. (1996) "Identification of Critical Amino Acids Involved in Alpha 1-Beta Interaction in Voltage-Dependent Ca2+ Channels," *FEBS Lett.* 380(3):272-276.

Doura et al. (2004) "Sequence Context Modulates the Stability of GxxxG-Mediated Transmembrane Helix-Helix Dimer," *J. Mol. Biol.* 341(4):991-998.

Dubel et al. (2004) "Plasma Membrane Expression of T-Type Calcium Channel Alpha 1 Subunits is Modulated by HVA Auxiliary Subunits," *J. Biol. Chem.* 279:29263-29269.

Eberst et al. (1997) "Identification and Functional Characterization of a Calcium Channel Gama Subunit," *Pflugers Arch.* 433(5):633-637.

Fletcher et all. (1998) "Genetic Analysis of Voltage Dependent Calcium Channels," *J. Bioeng. Biomembr.* 30(4):387-398.

Flockerzi et al. (1986) "Purified Dihydropyridine-Binding Site from Skeletal Muscle T-Tubules is a Functional Calcium Channel," *Nature* 323:66-68.

Freise et al. (2000) "Absence of the Gamma Subunit of the Skeletal Muscle Dihydropyridine Receptor Increases L-Type Ca2+ Currents and Alters Channel Inactivation Properties," *J. Biol. Chem.* 275(19):14476-14481.

Green, P. (2001) "Kinetic Modification of the Alpha1I Subunit-Mediated T-Type Ca2+ Channel by a Human Neuronal Ca2+ Channel Gamma Subunit," *J. Physiol.* 533(2):467-478.

Gurnett et al. (1997) "Extracellular Interaction of the Voltage Dependant Ca2+ Channel Aplpha 2 Delta and Alpha 1 Subunits," *J. Biol. Chem.* 272(29):18508-18512.

Hansen et al. (2004) "Calcium Channel γ6 Subunits are Unique Modulators of Low Voltage-Activated (Cav3.1) Calcium Current," *J. Mol. Cell. Cardiol.* 37:1147-1158.

Held et al. (2002) "Skeletal Muscle L-Type Ca($2^+$) Current Modulation in Gamma 1-Deficient and Wildtype Murine Myotubes by the Gamma1 Subunit and cAMP," *J. Physiol.* 539(2):459-468.

Hofmann et al. (1999) "Voltage-Dependent Calcium Channels: From Structure to Function," *Rev. Phys. Biochem. Pharmacol.* 139(2):33-87.

Jay et al. (1990) "Primary Structure of the Gamma Subunit of the DHP Sensitive Calcium Channel from Skeletal Muscle," *Science* 248:490-492.

Kang et al. (2001) "Biochemical and Biophysical Evidence for Gamma 2 Subunit Association with Neuronal Voltage-Activated $Ca^{2+}$ Channels," *J. Biol. Chem.* 276(35):32917-32924.

Kang et al. (2003) "Gamma Subunit of Voltage-Activated Calcium Channels," *J. Biol. Chem.* 2778(24):21315-21318.

Kleiger et al. (2002) "GXXXG and AXXXA: Common Alpha-Helical Interaction Motifs in Proteins, Particularly in Extremophiles," *Biochem.* 41(19):5990-5997.

Klugbauer et al. (2000) "A Family of Gamma-Like Calcium Channel Subunits," *FEBS* 470(2):189-197.

Klugbauer et al. (1999) "Molecular Diversity of the Calcium Channel Alpha 2 Delta Subunit," *J. Neurosci.* 19(2):684-691.

Lacinova et al. (2004) "Modulation of Gating Currents of the Ca(v)3.1 Calcium Channel by Alpha 2 Delta 2 and Gamma 5 Subunits," *Arch. Biochem. Biohys.* 425(2):207-213.

Larson et al. (2002) "Quantitative Analysis of the Expression and Distribution of Calcium Channel Alpha 1 Subunit mRNA in the Atria and Ventricles of the Rat Heart," *J. Mol. Cell. Cardiol.* 34(5):519-532.

Leonov et al. (2005) "A Periodicity Analysis of Transmembrane Helices," *Bioinformatics* 21(11):2604-2610.

Letts et al. (1998) "The Mouse Stargazer Gene Encodes a Neuronal $Ca^{2+}$-Channel Gamma Subunit," *Nat. Genet.* 19(4):340-347.

Leung et al. (1987) "Growth Hormone Receptor and Serum Binding Protein: Purification, Cloning and Expression," *Nature* 330:537-543.

Li et al. (2004) "Single-Channel Analysis of KCNQ $K^+$ Channels Reveals the Mechanism of Augmentation by Cysteine-Modifying Reagent," *J. Neurosci* 24(22):5079-5090.

Liu et al. (2002) "Genomic Analysis of Membrane Protein Families: Abundance and Conserved Motifs," *Genome. Biol.* 3(10):Research0054.1-0054.12.

Melnyk et al. (2004) "The Affinity of GXXXG Motifs in Transmembrane Helix-Helix Interactions is Modulated by Long-Range Communication," *J. Biol. Chem.* 279(16):16591-16597.

Moreno et al. (1997) "Beta Subunits Influence the Biophysical and Pharmacological Differences Between P- and Q-Type Calcium Currents Expressed in a Mammalian Cell Line," *Proc. Nat. Acad. Sci. USA* 94(25):14042-14047.

Moss et al. (2002) "The Novel Product of a Five-Exon Stargazin-Related Gene Abolishes Ca(V)2.2 Calcium Channel Expression," *Embo J.* 21(7):1514-1523.

Njue et al. (2004) "Mutations in the Extracellular Domains of Glutamate-Gated Chloride Channel Alpha3 and Beta Subunits From Ivermectin-Resistant Cooperia Oncophora Affect Agonist Sensitivity," *J. Neurochem.* 89(5):1137-1147.

Nuss et al. (1993) "T-Type Ca2+ Current is Expressed in Hypertrophied Adult Feline Left Ventricular Myocytes," *Circ. Res.* 73(4):777-782.

Pichler et al. (1997) "Beta Subunit Heterogeneity in Neuronal L-Type Ca2+ Channels," *J. Biol. Chem.* 272(21):13877-13882.

Pollack, A. (2005) "The Search for the Killer Painkiller," The New York Times Online Article, Feb. 15, 2005, http://www.nytimes.com2005/02/15/health/15pain,html?pagewanted=print&position=.

Pragnell et al. (1994) "Calcium Channel Beta-Subunit Binds to a Conserved Motif in the I-II Cytoplasmic Linker of the Alpha 1-Subunit," *Nature* 368:67-70.

Priel et al. (2005) "Stargazin Reduced Desensitization and Slows Deactivation of the AMPA-Type Glutamate Receptors," *J. Neurosci.* 25(10):2682-2686.

Rousset et al. (2001) "Functional Roles of Gamma-2, Gamma-3 and Gamma-4, Three New Ca2+ Channel Subunits, in P/Q-Type Ca2+ Channel Expressed in Xenopus Oocytes," *J. Physol.* 532(3):583-593.

Scott et al. (1996) "Beta Subunit Heterogeneity in N-Type Ca2+ Channels," *J. Biol. Chem.* 271(6):3207-3212.

Senes et al. (2000) "Statistical Analysis of Amino Acid Patterns in Transmembrane Helices: The GxxxG Motif Occurs Frequently and in Association with Beta-Branched Residues at Neighboring Positions," *J. Mol. Biol.* 296(3):921-936.

Sharp et al. (2001) "Biochemical and Anatomical Evidence for Specialized Voltage Dependent Calcium Channel Gamma Isoform Expression in the Epileptic and Ataxic Mouse, Stargazer," *Neurosci.* 105(3):599-617.

Singer et al. (1991) "The Roles of the Subunits in the Function of the Calcium Channel," *Science* 253(5027):1553-1557.

Tomita et al. (2003) "Functional Studies and Distribution Define a Family of Transmembrane AMPA Receptor Regulatory Proteins," *J. Cell. Biol.* 161(4):805-816.

Tomita et al. (2005) "Stargazin Modulates AMPA Receptor Gating and Trafficking by Distinct Domains," *Nature* 435:1052-1058.

Van Petegem et al. (2004) "Structure of a Complex Between a Voltage0Gated Calcium Channel Beta-Subunit and an Alpha-Subunit Domain," *Nature* 429:671-675.

Vandenberghe et al. (2005) "Stargazin is an AMPA Receptor Auxiliary Subunit," *Proc. Nat. Acad. Sci. USA* 102(2):485-490.

Wagner et al. (2004) "An Arginine Involved in GABA Binding and Unbinding but Not Gating of the GABA(A) Receptor," *J. Neurosci.* 24(11):2733-2741.

Wei et al. (1991) "Heterologous Regulation of the Cardiac Ca2+ Channel Alpha 1 Subunit by Skeletal Muscle Beta and Gamma Subunits. Implications for the Structure of Cardiac L-Type Ca2+ Channles," *J. Biol. Chem.* 266(32):21943-21947.

Williams et al. (1992) "Structure and Functional Expression of Alpha 1, Alpha2, and Beta Subunits of a Novel Human Neuronal Calcium Channel Subtype," *Neuron* 8(1):71-84.

Xu et al. (1990) "Increase in T-Type Calcium Current in Atrial Myocytes from Adult Rats with Growth Hormone-Secreting Tumors," *Proc. Nat. Acad. Sci. USA* 87:4655-4659.

Xu et al. (1992) "Postnatal Changes in T-Type Calcium Current Density in Rat Atrial Myocytes," *J. Physiol.* 454:657-672.

Zhang et al. (2002) "Mutations in High Voltage Activate Calcium Genes Stimulate Low Voltage Activated Currents in Mouse Thalamic Relay Neurons," *J. Neurosci.* 22:6362-6371.

Zhou et al. (2000) "Interhelical Hydrogen Binding Drives Strong Interactions in Membrane Proteins," *Nat. Struct. Biol.* 7(2):154-160.

Lin Z. et al., "A critical GxxxA motif in the γ6 calcium channel subunit mediates its inhibitory effect on Cav3.1 calcium current," J Physiol 586(22): 5349-5366, 2008.

International Search Report, International Application No. PCT/US06/38179, Apr. 16, 2008, 5 pages.

GenBank Accession AF361341, Gene 2001.

X. Qiao et al., Nonchannel functions of the calcium channel ? subunit: Insight from research on the Stargazer mutant, Journal of Bioenergetics and Biomembranes 35(6):661-670, 2003.

Arselin et al. (2003) "The GXXXG Motif of the Transmembrane Domain of Subunit e is Involved in the Dimerization/Oligomaerization of the Yeast ATP Synthase Complex in the Mitochondrial Membrane," *Eur. J. Biochem.* 270:1875-1884.

Chen et al. (May 2009) "A Small Peptide Inhibitor of the Low Voltage-Activated Calcium Channel Cav3.1," *Mol. Pharmacol.* 75(5):1042-1051.

Chinault et al. (Apr. 16, 2004) "Subunits of a Yeast Oligomeric G Protein-Coupled Receptor are Activated Independently by Agonist but Function in Concert to Activate G Protein Heterotrimers," *J. Biol. Chem.* 279(16):16091-16100.

Gerber et al. (May 14, 2004) "Two Motifs within a Transmembrane Domain, One for Homodimerization and the Other for Heterodimerization," *J. Biol. Chem.* 279(20):21177-21182.

Humphrey et al. (1996) "VMD—Visual Molecular Dynamics," *J. Mol. Graphics* 14:33-38.

Kleiger et al. (Oct. 11, 2002) "GXXXG and GXXXA Motifs Stabilize FAD and NAD(P)-Binding Rossmann Folds Through $C^{\alpha}$-H•••O Hydrogen Bonds and van der Waals Interactions," *J. Mol. Biol.* 323(1):69-76.

Kobus et al. (Feb. 8, 2005) "The GXXXG-Containing Transmembrane Domain of the CCK4 Oncogene Does Not Encode Preferential Self-Interactions," *Biochemistry* 44(5):1464-1470.

Lemmon et al. (Apr. 15, 1992) "Glycophorin A Dimerization is Driven by Specific Interactions Between Transmembrane α-Helices," *J. Biol. Chem.* 267(11):7683-7689.

Mendrola et al. (Feb. 15, 2002) "The Single Transmembrane Domains of ErbB Receptors Self-Associated in Cell Membranes," *J. Biol. Chem.* 277(7):4704-4712.

Mottamal et al. (Feb. 8, 2005) "The Contribution of $C_{\alpha}$-H•••O Hydrogen Bonds to Membrane Protein Stability Depends on the Position of the Amide," *Biochemistry* 44(5):1607-1613.

Osten et al. (Jun. 2006) "Learning from Stargazin: The Mouse the Phenotype and the Unexpected," *Curr. Opin. Neurobiol.* 16(3):275-280.

Parthasarathy et al. (2008) "Transmembrane Helices that Form Two Opposite Homodimeric Interactions: An Asparagine Scan Study of αM and β2 Integrins," *Prot. Sci.* 17:930-938.

Russ et al. (Feb. 25, 2000) "The GXXXG Motif: A Framework for Transmemebrane Helix-Helix Association," *J. Mol. Biol.* 296(3):911-919.

Schneider et al. (Oct. 29, 2004) "Motifs of Two Small Residues can Assist but are not Sufficient to Mediate Transmembrane Helix Interactions," *J. Mol. Biol.* 343(4):799-804.

Senes et al. (Aug. 2004) "Folding of Helical Membrane Proteins: The Role of Polar, GxxxG-like and Proline Motifs" *Curr. Opin. Struct. Biol.* 14(4):465-479.

VMD Visual Molecular Dynamics, Webpage Document, Theoretical and Computational Biophys Group, University of Illinois at Urbana-Champaign, NIH Resource for Macromolecular Modeling and Bioinformatics; [online], Aug. 2005 [Retrieved on Sep. 29, 2005]. Retrieved from the Internet: URL: http://www.ks.uiuc.edu/Research/vmd/.

Lin, Zuojun (2005), The calcium channel γ6 (gamma 6) subunit—analysis of function and determination of a sequence motif critical for its effect, Doctoral dissertation, University of Illinois at Urbana-Champaign, Urbana, Illinois (according to the Graduate College, deposited on Dec. 2, 2005).

* cited by examiner

γ6L N-terminal truncated (SEQ ID NO:3)

5'-ATCAAGCTTATCGATACCGTCGACCTCGAGGCATGACTCCGGAGCGAGAGGGCAAGATCAAGCTGGGGTTGCTG
GTGGCTATCGTGGGTGCCACTCTGGCTGTGCTAGCTGTGGGCACCGAGTTCTGGGTGGAACTCAATACATACAAGACCAACGG
CAGCGCCGTCTGTGAGGCCGCCCATTTGGGGCTGTGGAAGGTGTGCATCAAGCGACTGTGGCAGGCGGATGTACCCGCGGG
CAGGGAGACCTGTGGCCCAGCTGAGCTGCCAGGAGAAGCAAACTGCACCTACTTCAAGTTCTTCACCACGGGGGAAAATGCG
CACATCTTCCAGAGAACCACCAAGAAAGAGGTAAACCTGGCAGCTGCTGTGATAGCTGTGCTGGGCCTGACAGCCATGGCCTT
GGGCTGCCTCTGTGTCATCATGGTGCTCAGTAAAGGTGCAGAGTTCCTGCTCCGCTTGGGAGCTGTCTGCTTTGGCCTCTCAG
GCCTGCTGCTCTTTGTCAGCCTGGAGGTGTTCCGGCATTCCGTCAGAGCCCTGCTGCAGGGGGTCAACCCTGAGACCCCTCC
AGCTCCACGCCTGGCCTATGAGTATTCCTGGTCCCTAGGCTGTGGTGTGGGCGCTGGTCTAATCCTGCTGCTGGGGGGAGTCT
GTTTCCTCCTGCTCACCCTGCCTTCCTGGCCCTGGAGGTCACTGTGCCCCAAGCGGGGTGGCCCAACTGCCTAGAAGCCGAAT
TCTGCAGTCGACGGTACCGCGGGCCCGGGATCCACCGGATCTAGATAACTGATC-3'

γ4 C-terminal truncated (SEQ ID NO:4)

5'-ATCAAGCTTATCGATACCGTCGACCTCGAGCTCAAGCTTCGAATTCACCATGGTGCGATGCGACCGCGGGCTGCA
GATGCTGCTGACCACGGCTGGAGCCTTCGCCGCCTTCTCGCTCATGGCCATCGCCATCGGCACTGACTACTGGCTGTACTCCA
GCGCGCACATCTGCAACGGCACCAACCTGACCATGGACGACGGGCCCCCGCCCCGCCGGCGCCCGCGGCGACCTCACCCATT
CGGGACTGTGGCGGGTGTGTTGCATCGAAGGCATCTACAAGGGGCACTGCTTCCGGATCAACCACTTCCCAGAGGACAACGA
TTATGACCACGACAGCTCCGAGTACCTCCTCCGCATTGTGCGAGCCTCCAGTGTCTTCCCCATCCTCAGCACCATTCTGCTCCT
GCTTGGAGGGCTCTGCATCGGCGCTGGGAGGATCTACAGCCGCAAGAACAACATTGTCCTCAGTGCAGGAATCCTCTTTGTGG
CTGCAGGCCTCAGTAATATCATCGGCATCATCGTCTACATTTCCAGCAACACGGGCGACCCCAGTGACAAGCGTGACGAAGAC
AAGAAGAACCATTACAACTACGGCTGGTCTTTTTACTTTGGAGCCCTGTCGTTTATTGTGGCGGAGACCGTGGGCGTTCTGGCT
GTAAACATTTACATTGAGAAAAACAAAGAGTTGAGGTTTAAGACCAAGCGGGAGTTCCTCAAGGCCTCTTCCTCCTCTCCTTACT
CCAGGATGCCGAGTTACAGGTACCGGTGACGGCGCTCCAGGTCCAGTTCGAGGTCCACTGAGGCCTCACCCTCTAGAGATGC
CTCTCCTGTGGGCCTGAAGATCACGGGGGCCATTCCCATGGGTGAGCTGTCCATGTACACGCTGTCCAGAGAACCCCTCAAG
GTGACCACAGGGGATCCACCGGATCTAGATAACTGATC-3'

γ6444 (SEQ ID NO:5)

5'-ATCAAGCTTATCGATACCGTCGACCTCGAGCTCAAGCTTCGAATTCGGCTTATGATGTGGTCTAACTTCTTCATGCA
AGAGGAAGACCGTCGTCGGACGGCTGTGGGCCGGCGTCGTGCCCAAGAACAGCAGAATCTCGGCTTGACTCCGGAGCGAGA
GGGCAAGATCAAGCTGGGGTTGCTGGTGGCTATCGTGGGTGCCACTCTGGCTGTGCTAGCTGTGGGCACCGAGTTCTGGGTG
GAACTCAATACATACAAGACCAACGGCAGCGCCGTCTGTGAGGCCGCCCATTTGGGGCTGTGGAAGGTGTGCATCAAGCGAC
TGTGGCAGGCGGATGTACCCGCGGGCATCTACAAGGGGCACTGCTTCCGGATCAACCACTTCCCAGAGGACAACGATTATGA
CCACGACAGCTCCGAGTACCTCCTCCGCATTGTGCGAGCCTCCAGTGTCTTCCCCATCCTCAGCACCATTCTGCTCCTGCTTG
GAGGGCTCTGCATCGGCGCTGGGAGGATCTACAGCCGCAAGAACAACATTGTCCTCAGTGCAGGAATCCTCTTTGTGGCTGCA
GGCCTCAGTAATATCATCGGCATCATCGTCTACATTTCCAGCAACACGGGCGACCCCAGTGACAAGCGTGACGAAGACAAGAA
GAACCATTACAACTACGGCTGGTCTTTTTACTTTGGAGCCCTGTCGTTTATTGTGGCGGAGACCGTGGGCGTTCTGGCTGTAAA
CATTTACATTGAGAAAAACAAAGAGTTGAGGTTTAAGACCAAGCGGGAGTTCCTCAAGGCCTCTTCCTCCTCTCCTTACTCCAG
GATGCCGAGTTACAGGTACCGGCGACGGCGCTCCAGGTCCAGTTCGAGGTCCACTGAGGCCTCACCCTCTAGAGATGCCTCT
CCTGTGGGCCTGAAGATCACGGGGGCCATTCCCATGGGTGAGCTGTCCATGTACACGCTGTCCAGAGAACCCCTCAAGGTGA
CCACAGCTGCCAGCTACAGTCCGGATCAGGATGCTGGCTTCCTACAGATGCATGACTTCTTCCAACAGGACCTAAAGGAGGGT
TTCCACGTCAGCATGCTGAACCGACGGACGACCCCTGTGTGACGAATTCTGCAGTCGACGGTACCGCGGGCCCGGGATCCAC
CGGATCTAGATAACTGATC-3'

FIG. 11A

γ4446 (SEQ ID NO:6)

5'-ATCAAGCTTATCGATACCGTCGACCTCGAGCTCAAGCTTCGAATTCACCATGGTGCGATGCGACCGCGGGCTGCA
GATGCTGCTGACCACGGCTGGAGCCTTCGCCGCCTTCTCGCTCATGGCCATCGCCATCGGCACTGACTACTGGCTGTACTCCA
GCGCGCACATCTGCAACGGCACCAACCTGACCATGGACGACGGGCCCCCGCCCCGCCGCGCCCGCGGCGACCTCACCCATT
CGGGACTGTGGCGGGTGTGTTGCATCGAAGGCATCTACAAGGGGCACTGCTTCCGGATCAACCACTTCCCAGAGGACAACGA
TTATGACCACGACAGCTCCGAGTACCTCCTCCGCATTGTGCGAGCCTCCAGTGTCTTCCCCATCCTCAGCACCATTCTGCTCCT
GCTTGGAGGGCTCTGCATCGGCGCTGGGAGGATCTACAGCCGCAAGAACAACATTGTCCTCAGTGCAGGAATCCTCTTTGTGG
CTGCAGGCCTCAGTAATATCATCGGCATCATCGTCTACCGGCATTCCGTCAGAGCCCTGCTGCAGGGGGTCAACCCTGAGACC
CCTCCAGCTCCACGCCTGGCCTATGAGTATTCCTGGTCCCTAGGCTGTGGTGTGGGCGCTGGTCTAATCCTGCTGCTGGGGG
GAGTCTGTTTCCTCCTGCTCACCCTGCCTTCCTGGCCCTGGAGGTCACTGTGCCCCAAGCGGGGTGGCCCAACTGCCTAGAAG
CCGAATTCTGCAGTCGACGGTACCGCGGGCCCGGGATCCACCGGATCTAGATAACTGATC-3'

γ6664 (SEQ ID NO:7)

5'-ATCAAGCTTATCGATACCGTCGACCTCGAGCTCAAGCTTCGAATTCGGCTTATGATGTGGTCTAACTTCTTCATGCA
AGAGGAAGACCGTCGTCGGACGGCTGTGGGCCGGCGTCGTGCCCAAGAACAGCAGAATCTCGGCTTGACTCCGGAGCGAGA
GGGCAAGATCAAGCTGGGGTTGCTGGTGGCTATCGTGGGTGCCACTCTGGCTGTGCTAGCTGTGGGCACCGAGTTCTGGGTG
GAACTCAATACATACAAGACCAACGGCAGCGCCGTCTGTGAGGCCGCCCATTTGGGGCTGTGGAAGGTGTGCATCAAGCGAC
TGTGGCAGGCGGATGTACCCGCGGGCAGGGAGACCTGTGGCCCAGCTGAGCTGCCAGGAGAAGCAAACTGCACCTACTTCAA
GTTCTTCACCACGGGGGAAAATGCGCACATCTTCCAGAGAACCACCAAGAAAGAGGTAAACCTGGCAGCTGCTGTGATAGCTG
TGCTGGGCCTGACAGCCATGGCCTTGGGCTGCCTCTGTGTCATCATGGTGCTCAGTAAAGGTGCAGAGTTCCTGCTCCGCTTG
GGAGCTGTCTGCTTTGGCCTCTCAGGCCTGCTGCTCTTTGTCAGCCTGGAGGTGTTCCGGCATTCCGTCAGAGCCCTGCTGCA
GAACCATTACAACTACGGCTGGTCTTTTTACTTTGGAGCCCTGTCGTTTATTGTGGCGGAGACCGTGGGCGTTCTGGCTGTAAA
CATTTACATTGAGAAAAACAAAGAGTTGAGGTTTAAGACCAAGCGGGAGTTCCTCAAGGCCTCTTCCTCCTCTCCTTACTCCAG
GATGCCGAGTTACAGGTACCGGCGACGGCGCTCCAGGTCCAGTTCGAGGTCCACTGAGGGCCTCACCCTCTAGAGATGCCTCT
CCTGTGGGCCTGAAGATCACGGGGGCCATTCCCATGGGTGAGCTGTCCATGTACACGCTGTCCAGAGAACCCCTCAAGGTGA
CCACAGCTGCCAGCTACAGTCCGGATCAGGATGCTGGCTTCCTACAGATGCATGACTTCTTCCAACAGGACCTAAAGGAGGGT
TTCCACGTCAGCATGCTGAACCGACGGACGACCCCTGTGTGACGAATTCTGCAGTCGACGGTACCGCGGGCCCGGGATCCAC
CGGATCTAGATAACTGATC-3'

γ4666 (SEQ ID NO:8)

5'-ATCAAGCTTATCGATACCGTCGACCTCGAGCTCAAGCTTCGAATTCACCATGGTGCGATGCGACCGCGGGCTGCA
GATGCTGCTGACCACGGCTGGAGCCTTCGCCGCCTTCTCGCTCATGGCCATCGCCATCGGCACTGACTACTGGCTGTACTCCA
GCGCGCACATCTGCAACGGCACCAACCTGACCATGGACGACGGGCCCCCGCCCCGCCGCGCCCGCGGCGACCTCACCCATT
CGGGACTGTGGCGGGTGTGTTGCATCGAAGGCATCTACAAGGGGCACTGCTTCCGGATCAACCACTTCCCAGAGGACAACGA
TTATGACCACGACAGCTCCGAGTACCTCCTCCGCATTGTGCCAGCTGCTGTGATAGCTGTGCTGGGCCTGACAGCCATGGCCT
TGGGCTGCCTCTGTGTCATCATGGTGCTCAGTAAAGGTGCAGAGTTCCTGCTCCGCTTGGGAGCTGTCTGCTTTGGCCTCTCA
GGCCTGCTGCTCTTTGTCAGCCTGGAGGTGTTCCGGCATTCCGTCAGAGCCCTGCTGCAGGGGGTCAACCCTGAGACCCCTC
CAGCTCCACGCCTGGCCTATGAGTATTCCTGGTCCCTAGGCTGTGGTGTGGGCGCTGGTCTAATCCTGCTGCTGGGGGGAGT
CTGTTTCCTCCTGCTCACCCTGCCTTCCTGGCCCTGGAGGTCACTGTGCCCCAAGCGGGGTGGCCCAACTGCCTAGAAGCCG
AATTCTGCAGTCGACGGTACCGCGGGCCCGGGATCCACCGGATCTAGATAACTGATC-3'

FIG. 11B

γ6446 (SEQ ID NO:9)

5'-ATCAAGCTTATCGATACCGTCGACCTCGAGCTCAAGCTTCGAATTCGGCTTATGATGTGGTCTAACTTCTTCATGCA
AGAGGAAGACCGTCGTCGGACGGCTGTGGGCCGGCGTCGTGCCCAAGAACAGCAGAATCTCGGCTTGACTCCGGAGCGAGA
GGGCAAGATCAAGCTGGGGTTGCTGGTGGCTATCGTGGGTGCCACTCTGGCTGTGCTAGCTGTGGGCACCGAGTTCTGGGTG
GAACTCAATACATACAAGACCAACGGCAGCGCCGTCTGTGAGGCCGCCCATTTGGGGCTGTGGAAGGTGTGCATCAAGCGAC
TGTGGCAGGCGGATGTACCCGCGGGCATCTACAAGGGGCACTGCTTCCGGATCAACCACTTCCCAGAGGACAACGATTATGA
CCACGACAGCTCCGAGTACCTCCTCCGCATTGTGCGAGCCTCCAGTGTCTTCCCCATCCTCAGCACCATTCTGCTCCTGCTTG
GAGGGCTCTGCATCGGCGCTGGGAGGATCTACAGCCGCAAGAACAACATTGTCCTCAGTGCAGGAATCCTCTTTGTGGCTGCA
GGCCTCAGTAATATCATCGGCATCATCGTCTACCGGCATTCCGTCAGAGCCCTGCTGCAGGGGGTCAACCCTGAGACCCCTCC
AGCTCCACGCCTGGCCTATGAGTATTCCTGGTCCCTAGGCTGTGGTGTGGGCGCTGGTCTAATCCTGCTGCTGGGGGGAGTCT
GTTTCCTCCTGCTCACCCTGCCTTCCTGGCCCTGGAGGTCACTGTGCCCCAAGCGGGGTGGCCCAACTGCCTAGAAGCCGAAT
TCTGCAGTCGACGGTACCGCGGGCCCGGGATCCACCGGATCTAGATAACTGATC-3'

γ4.6666 (SEQ ID NO:10)

5'-ATCAAGCTTATCGATACCGTCGACCTCGAGCTCAAGCTTCGAATTCACCATGGTGCGATGCGACCGCGGGCTGCA
GATGCTGGGGTTGCTGGTGGCTATCGTGGGTGCCACTCTGGCTGTGCTAGCTGTGGGCACCGAGTTCTGGGTGGAACTCAAT
ACATACAAGACCAACGGCAGCGCCGTCTGTGAGGCCGCCCATTTGGGGCTGTGGAAGGTGTGCATCAAGCGACTGTGGCAGG
CGGATGTACCCGCGGGCAGGGAGACCTGTGGCCCAGCTGAGCTGCCAGGAGAAGCAAACTGCACCTACTTCAAGTTCTTCAC
CACGGGGGAAAATGCGCACATCTTCCAGAGAACCACCAAGAAAGAGGTAAACCTGGCAGCTGCTGTGATAGCTGTGCTGGGC
CTGACAGCCATGGCCTTGGGCTGCCTCTGTGTCATCATGGTGCTCAGTAAAGGTGCAGAGTTCCTGCTCCGCTTGGGAGCTGT
CTGCTTTGGCCTCTCAGGCCTGCTGCTCTTTGTCAGCCTGGAGGTGTTCCGGCATTCCGTCAGAGCCCTGCTGCAGGGGGTCA
ACCCTGAGACCCCTCCAGCTCCACGCCTGGCCTATGAGTATTCCTGGTCCCTAGGCTGTGGTGTGGGCGCTGGTCTAATCCTG
CTGCTGGGGGGAGTCTGTTTCCTCCTGCTCACCCTGCCTTCCTGGCCCTGGAGGTCACTGTGCCCCAAGCGGGGTGGCCCAA
CTGCCTAGAAGCCGAATTCTGCAGTCGACGGTACCGCGGGCCCGGGATCCACCGGATCTAGATAACTGATC-3'

γ6 N-terminal deleted (SEQ ID NO:11)

5'-ATCAAGCTTATCGATACCGTCGACCTCGAGCATGCTGGGGTTGCTGGTGGCTATCGTGGGTGCCACTCTGGCTGT
GCTAGCTGTGGGCACCGAGTTCTGGGTGGAACTCAATACATACAAGACCAACGGCAGCGCCGTCTGTGAGGCCGCCCATTTG
GGGCTGTGGAAGGTGTGCATCAAGCGACTGTGGCAGGCGGATGTACCCGCGGGCAGGGAGACCTGTGGCCCAGCTGAGCTG
CCAGGAGAAGCAAACTGCACCTACTTCAAGTTCTTCACCACGGGGGAAAATGCGCACATCTTCCAGAGAACCACCAAGAAAGA
GGTAAACCTGGCAGCTGCTGTGATAGCTGTGCTGGGCCTGACAGCCATGGCCTTGGGCTGCCTCTGTGTCATCATGGTGCTCA
GTAAAGGTGCAGAGTTCCTGCTCCGCTTGGGAGCTGTCTGCTTTGGCCTCTCAGGCCTGCTGCTCTTTGTCAGCCTGGAGGTG
TTCCGGCATTCCGTCAGAGCCCTGCTGCAGGGGGTCAACCCTGAGACCCCTCCAGCTCCACGCCTGGCCTATGAGTATTCCTG
GTCCCTAGGCTGTGGTGTGGGCGCTGGTCTAATCCTGCTGCTGGGGGGAGTCTGTTTCCTCCTGCTCACCCTGCCTTCCTGGC
CCTGGAGGTCACTGTGCCCCAAGCGGGGTGGCCCAACTGCCTAGAAGCCGAATTCTGCAGTCGACGGTACCGCGGGCCCGG
GATCCACCGGATCTAGATAACTGATC-3'

FIG. 11C

TM1 Alignment

```
                                Position
                                                                SEQ ID
                    1 2 3 4 5 6 7 8 9 10 11 12 13 14 15 16 17 18 19 20   NO:
          γ6    N-  K L G L L V A I V  G  A  T  L  A  V  L  A  V  G  T  -C   12

γ1    N-  R V T L F F I L A  G  G  V  L  A  M  V  A  V  V  T  -C   13

TARP's
          γ3    N-  L I T T V G A F A  A  F  S  L  M  T  I  A  V  G  T  -C   14
          γ2    N-  L L T T V G A F A  A  F  S  L  M  T  I  A  V  G  T  -C   15
          γ8    N-  L L T T I G A F A  A  F  G  L  M  T  I  A  I  S  T  -C   16
          γ4    N-  L L T T A G A F A  A  F  S  L  M  A  I  A  I  G  T  -C   17

γ7    N-  L L S S V F G A C  G  L  L  L  V  G  I  A  V  S  T  -C   18
          γ5    N-  L L S S V F A V C  G  L  G  L  L  G  I  A  V  S  T  -C   19
```

Bold = Agreement

FIG. 20

TM1 Agreement by Amino Acid Side Chain Type

Position

| | γ6 | γ4 | γ7 | γ1 |
|---|---|---|---|---|
| 1 | lys (basic) | leu (non-polar) | leu (non-polar) | arg (basic) |
| 2 | leu (non-polar) | leu (non-polar) | leu (non-polar) | val (non-polar) |
| 3 | gly (non-polar) | thr (uncharged polar) | ser (uncharged polar) | thr (uncharged polar) |
| 4 | leu (non-polar) | thr (uncharged polar) | ser (uncharged polar) | leu (non-polar) |
| 5 | leu (non-polar) | ala (non-polar) | val (non-polar) | phe (non-polar aromatic) |
| 6 | val (non-polar) | gly (non-polar) | phe (non-polar aromatic) | phe (non-polar aromatic) |
| 7 | ala (non-polar) | ala (non-polar) | gly (non-polar) | ile (non-polar) |
| 8 | ile (non-polar) | phe (non-polar aromatic) | ala (non-polar) | leu (non-polar) |
| 9 | val (non-polar) | ala (non-polar) | cys (sulfhydral) | ala (non-polar) |
| 10 | gly (non-polar) | ala (non-polar) | gly (non-polar) | gly (non-polar) |
| 11 | ala (non-polar) | phe (non-polar aromatic) | leu (non-polar) | gly (non-polar) |
| 12 | thr (uncharged polar) | ser (uncharged polar) | leu (non-polar) | val (non-polar) |
| 13 | leu (non-polar) | leu (non-polar) | leu (non-polar) | leu (non-polar) |
| 14 | ala (non-polar) | met (thioether) | val (non-polar) | ala (non-polar) |
| 15 | val (non-polar) | ala (non-polar) | gly (non-polar) | met (thioether) |
| 16 | leu (non-polar) | ile (non-polar) | ile (non-polar) | val (non-polar) |
| 17 | ala (non-polar) | ala (non-polar) | ala (non-polar) | ala (non-polar) |
| 18 | val (non-polar) | ile (non-polar) | val (non-polar) | val (non-polar) |
| 19 | gly (non-polar) | gly (non-polar) | ser (uncharged polar) | val (non-polar) |
| 20 | thr (uncharged polar) | thr (uncharged polar) | thr (uncharged polar) | thr (uncharged polar) |

FIG. 21

|   | 1  | 2  | 3  | 4  | 5  | 6  | 7  | 8  | 9  | 10 | 11 | 12 | 13 | 14 | 15 | 16 | 17 | 18 | 19 | 20 |
|---|----|----|----|----|----|----|----|----|----|----|----|----|----|----|----|----|----|----|----|----|
|   | 40 | 41 | 42 | 43 | 44 | 45 | 46 | 47 | 48 | 49 | 50 | 51 | 52 | 53 | 54 | 55 | 56 | 57 | 58 | 59 |
| γ6 | K | L | G | L | V | A | I | V | G | A | T | L | A | V | L | A | V | G | T |
| γ4 | L | L | T | T | A | G | A | F | A | A | F | S | L | M | A | I | A | I | G | T |
|   | 11 | 12 | 13 | 14 | 15 | 16 | 17 | 18 | 19 | 20 | 21 | 22 | 23 | 24 | 25 | 26 | 27 | 28 | 29 | 30 |

γ6 = SEQ ID NO:12
γ4 = SEQ ID NO:17

|   | 1 | 2 | 3 | 4 | 5 | 6 | 7 | 8 | 9 | 10 | 11 | 12 | 13 | 14 | 15 | 16 | 17 | 18 | 19 | 20 |
|---|---|---|---|---|---|---|---|---|---|----|----|----|----|----|----|----|----|----|----|----|
|   | 40 | 41 | 42 | 43 | 44 | 45 | 46 | 47 | 48 | 49 | 50 | 51 | 52 | 53 | 54 | 55 | 56 | 57 | 58 | 59 |
| γ6 | K | L | G | L | L | V | A | I | V | G | A | $\underline{T}$ | L | A | V | L | A | V | G | $\underline{T}$ |
| γ6(G42L) | K | L | L | L | L | V | A | I | V | G | A | $\underline{T}$ | L | A | V | L | A | V | G | $\underline{T}$ |
| γ6(G49L) | K | L | G | L | L | V | A | I | V | L | A | $\underline{T}$ | L | A | V | L | A | V | G | $\underline{T}$ |

γ6(G42L) = SEQ ID NO:20
γ6(G49L) = SEQ ID NO:21

|   | 1 | 2 | 3 | 4 | 5 | 6 | 7 | 8 | 9 | 10 | 11 | 12 | 13 | 14 | 15 | 16 | 17 | 18 | 19 | 20 |
|---|---|---|---|---|---|---|---|---|---|----|----|----|----|----|----|----|----|----|----|----|
|   | 11 | 12 | 13 | 14 | 15 | 16 | 17 | 18 | 19 | 20 | 21 | 22 | 23 | 24 | 25 | 26 | 27 | 28 | 29 | 30 |
| γ4 | L | L | T | T | A | G | A | F | A | F | S | L | M | A | I | A | I | G | T |
| γ4(L23G) | L | L | T | T | A | G | A | F | A | F | S | G | M | A | I | A | I | G | T |

γ4(L23G) = SEQ ID NO:22

A
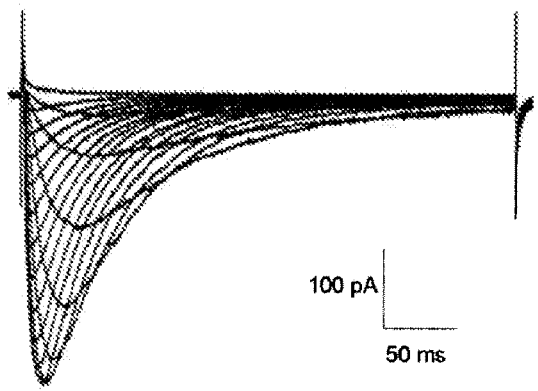
B
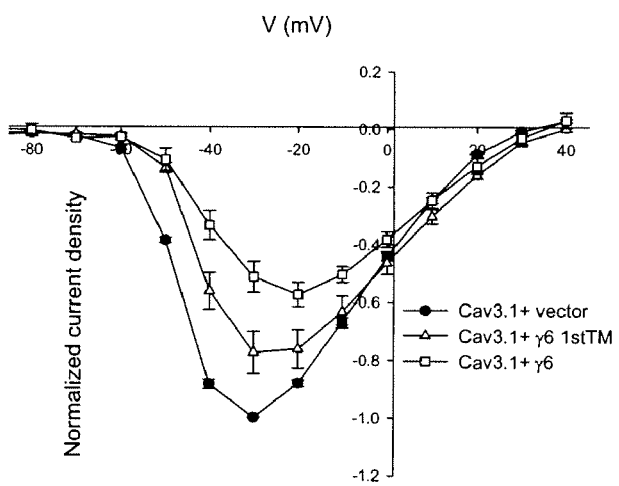
C
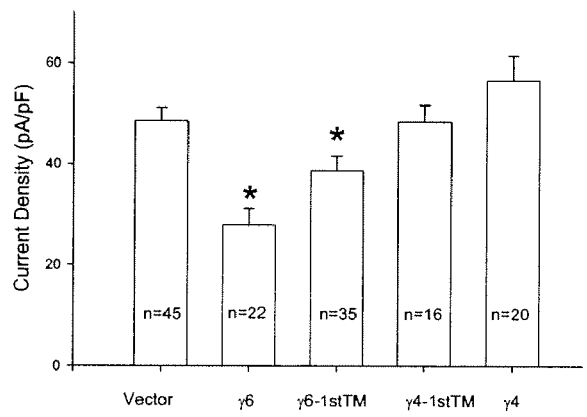
FIG. 25

Single, fully conserved residue: positions 13, 17, 20
Relatively conserved: positions 2, 6, 10, 18
No consensus: positions 1, 3,4,5,7,8,9,11,12,14,15,16,19
Candidate for mutation: g6 at position 1 (K), 3 (G), 4 (L)

Glycine

Gly, Glycine
NP, Nonpolar
U, Uncharged-polar

|    | 40 | 41 | 42 | 43 | 44 | 45 | 46 | 47 | 48 | 49 | 50 | 51 | 52 | 53 | 54 | 55 | 56 | 57 | 58 | 59 |
|----|----|----|----|----|----|----|----|----|----|----|----|----|----|----|----|----|----|----|----|----|
| g6 | K  | L  | Ⓖ  | L  | L  | V  | Ⓐ  | I  | V  | Ⓖ  | A  | T  | L  | Ⓐ  | V  | L  | A  | V  | G  | T  |
| g1 | R  | V  | T  | L  | F  | F  | I  | L  | A  | Ⓖ  | G  | T  | L  | Ⓐ  | M  | V  | A  | V  | V  | T  |
|    | 10 | 11 | 12 | 13 | 14 | 15 | 16 | 17 | 18 | 19 | 20 | 21 | 22 | 23 | 24 | 25 | 26 | 27 | 28 | 29 |

| g4 | L | L | T | T | A | G | A | F | A | A | F | S | L | M | A | I | A | I | G | T |
|----|---|---|---|---|---|---|---|---|---|---|---|---|---|---|---|---|---|---|---|---|
|    | 11| 12| 13| 14| 15| 16| 17| 18| 19| 20| 21| 22| 23| 24| 25| 26| 27| 28| 29| 30|

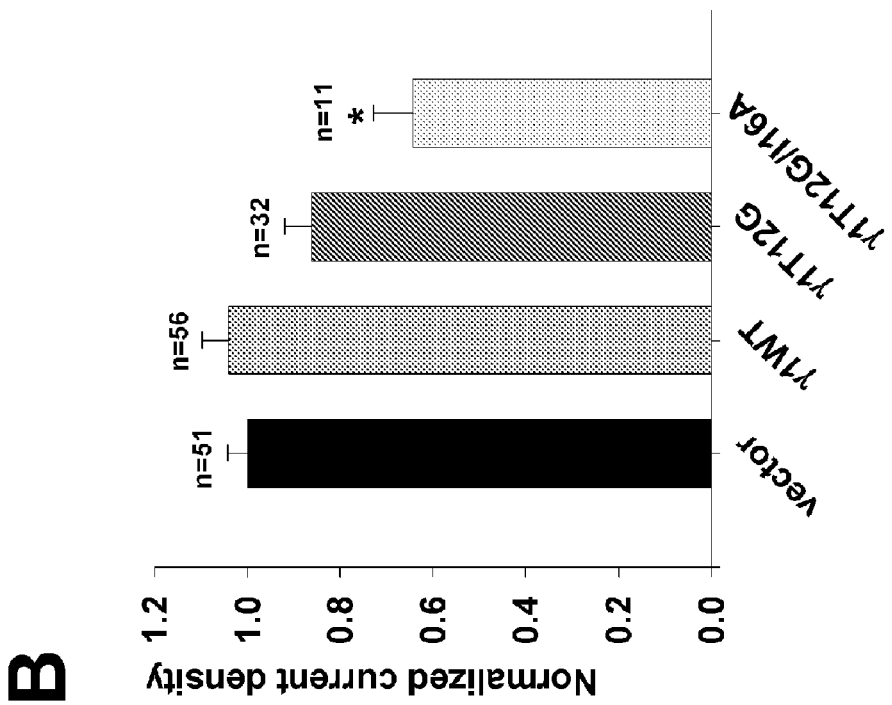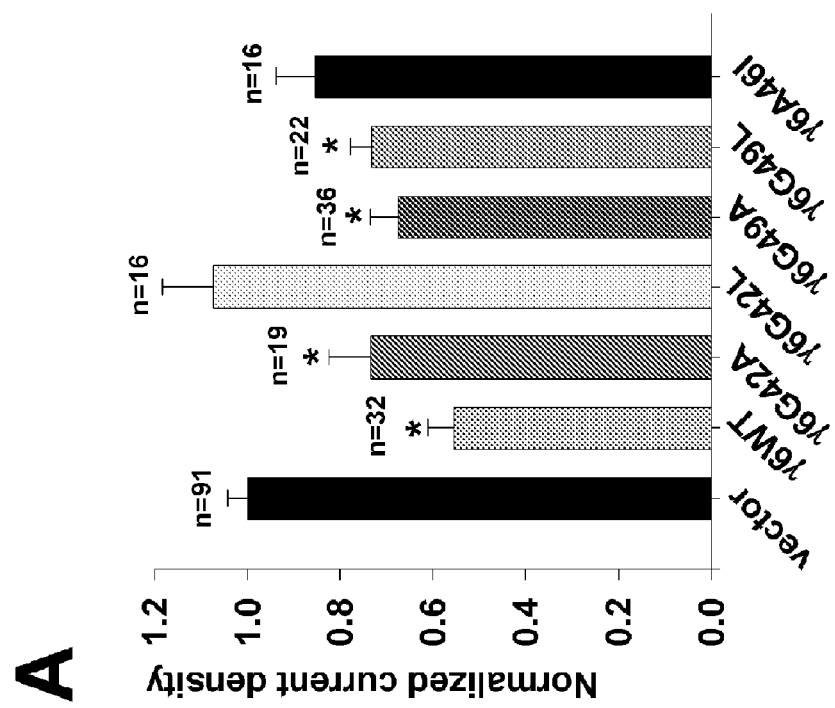
FIG. 41

SEQUENCE LISTING

<160> NUMBER OF SEQ ID NOS: 50

<210> SEQ ID NO 1
<211> LENGTH: 5
<212> TYPE: PRT
<213> ORGANISM: Artificial
<220> FEATURE:
<223> OTHER INFORMATION: Synthetic peptide/protein
<220> FEATURE:
<221> NAME/KEY: misc_feature
<222> LOCATION: (2)..(4)
<223> OTHER INFORMATION: Xaa can be any naturally occurring amino acid

```
<400> SEQUENCE: 1

Gly Xaa Xaa Xaa Gly
1               5

<210> SEQ ID NO 2
<211> LENGTH: 5
<212> TYPE: PRT
<213> ORGANISM: Artificial
<220> FEATURE:
<223> OTHER INFORMATION: Synthetic construct
<220> FEATURE:
<221> NAME/KEY: misc_feature
<222> LOCATION: (2)..(4)
<223> OTHER INFORMATION: Xaa can be any naturally occurring amino acid

<400> SEQUENCE: 2

Gly Xaa Xaa Xaa Ala
1               5

<210> SEQ ID NO 3
<211> LENGTH: 788
<212> TYPE: DNA
<213> ORGANISM: Artificial
<220> FEATURE:
<223> OTHER INFORMATION: Synthetic construct, gamma 6L N-terminal
      truncated

<400> SEQUENCE: 3
atcaagctta tcgataccgt cgacctcgag gcatgactcc ggagcgagag ggcaagatca      60
agctggggtt gctggtggct atcgtgggtg ccactctggc tgtgctagct gtgggcaccg     120
agttctgggt ggaactcaat acatacaaga ccaacggcag cgccgtctgt gaggccgccc     180
atttggggct gtggaaggtg tgcatcaagc gactgtggca ggcggatgta cccgcgggca     240
gggagacctg tgcccagct gagctgccag gagaagcaaa ctgcacctac ttcaagttct     300
tcaccacggg ggaaaatgcg cacatcttcc agagaaccac caagaaagag gtaaacctgg     360
cagctgctgt gatagctgtg ctgggcctga cagccatggc cttgggctgc ctctgtgtca     420
tcatggtgct cagtaaaggt gcagagttcc tgctccgctt gggagctgtc tgctttggcc     480
tctcaggcct gctgctcttt gtcagcctgg aggtgttccg gcattccgtc agagccctgc     540 tgcaggggt caaccctgag acccctccag ctccacgcct ggcctatgag tattcctggt     600
ccctaggctg tggtgtgggc gctggtctaa tcctgctgct ggggggagtc tgtttcctcc     660
tgctcaccct gccttcctgg ccctggaggt cactgtgccc caagcggggt ggcccaactg     720
cctagaagcc gaattctgca gtcgacggta ccgcgggccc gggatccacc ggatctagat     780
aactgatc                                                             788

<210> SEQ ID NO 4
<211> LENGTH: 942
<212> TYPE: DNA
<213> ORGANISM: Artificial
<220> FEATURE:
<223> OTHER INFORMATION: Synthetic construct, gamma 4 C-terminal
      truncated

<400> SEQUENCE: 4
atcaagctta tcgataccgt cgacctcgag ctcaagcttc gaattcacca tggtgcgatg      60
cgaccgcggg ctgcagatgc tgctgaccac ggctggagcc ttcgccgcct tctcgctcat     120
ggccatcgcc atcggcactg actactggct gtactccagc gcgcacatct gcaacggcac     180
caacctgacc atgacgacg ggccccgcc ccgccgcgcc cgcggcgacc tcacccattc     240
```

```
gggactgtgg cgggtgtgtt gcatcgaagg catctacaag gggcactgct tccggatcaa    300
ccacttccca gaggacaacg attatgacca cgacagctcc gagtacctcc tccgcattgt    360
gcgagcctcc agtgtcttcc ccatcctcag caccattctg ctcctgcttg gagggctctg    420
catcggcgct gggaggatct acagccgcaa gaacaacatt gtcctcagtg caggaatcct    480
ctttgtggct gcaggcctca gtaatatcat cggcatcatc gtctacattt ccagcaacac    540
gggcgacccc agtgacaagc gtgacgaaga caagaagaac cattacaact acggctggtc    600
ttttactttt ggagccctgt cgtttattgt ggcggagacc gtgggcgttc tggctgtaaa    660
catttacatt gagaaaaaca aagagttgag gtttaagacc aagcgggagt tcctcaaggc    720
ctcttcctcc tctccttact ccaggatgcc gagttacagg taccggtgac ggcgctccag    780
gtccagttcg aggtccactg aggcctcacc ctctagagat gcctctcctg tgggcctgaa    840
gatcacgggg gccattccca tgggtgagct gtccatgtac acgctgtcca gagaacccct    900
caaggtgacc acaggggatc caccggatct agataactga tc                       942

<210> SEQ ID NO 5
<211> LENGTH: 1169
<212> TYPE: DNA
<213> ORGANISM: Artificial
<220> FEATURE:
<223> OTHER INFORMATION: Synthetic construct, gamma 6444

<400> SEQUENCE: 5
atcaagctta tcgataccgt cgacctcgag ctcaagcttc gaattcggct tatgatgtgg     60
tctaacttct tcatgcaaga ggaagaccgt cgtcggacgg ctgtgggccg gcgtcgtgcc    120
caagaacagc agaatctcgg cttgactccg gagcgagagg gcaagatcaa gctggggttg    180
ctggtggcta tcgtgggtgc cactctggct gtgctagctg tgggcaccga gttctgggtg    240
gaactcaata catacaagac caacggcagc gccgtctgtg aggccgccca tttggggctg    300
tggaaggtgt gcatcaagcg actgtggcag gcggatgtac ccgcgggcat ctacaagggg    360
cactgcttcc ggatcaacca cttcccagag gacaacgatt atgaccacga cagctccgag    420
tacctcctcc gcattgtgcg agcctccagt gtcttcccca tcctcagcac cattctgctc    480
ctgcttggag ggctctgcat cggcgctggg aggatctaca gccgcaagaa caacattgtc    540
ctcagtgcag gaatcctctt tgtggctgca ggcctcagta atatcatcgg catcatcgtc    600
tacatttcca gcaacacggg cgaccccagt gacaagcgtg acgaagacaa gaagaaccat    660
tacaactacg gctggtcttt ttactttgga gccctgtcgt ttattgtggc ggagaccgtg    720
ggcgttctgg ctgtaaacat ttacattgag aaaaacaaag agttgaggtt taagaccaag    780
cgggagttcc tcaaggcctc ttcctcctct ccttactcca ggatgccgag ttacaggtac    840
cggcgacggc gctccaggtc cagttcgagg tccactgagg cctcaccctc tagagatgcc    900
tctcctgtgg gcctgaagat cacgggggcc attcccatgg gtgagctgtc catgtacacg    960
ctgtccagag aacccctcaa ggtgaccaca ggggatccac cggatctaga taactgatc   1020 ggcttcctac agatgcatga cttcttccaa caggacctaa aggagggttt ccacgtcagc   1080
atgctgaacc gacggacgac ccctgtgtga cgaattctgc agtcgacggt accgcgggcc   1140
cgggatccac cggatctaga taactgatc                                     1169

<210> SEQ ID NO 6
<211> LENGTH: 796
<212> TYPE: DNA
<213> ORGANISM: Artificial
```

```
<220> FEATURE:
<223> OTHER INFORMATION: Synthetic construct, gamma 4446

<400> SEQUENCE: 6
atcaagctta tcgataccgt cgacctcgag ctcaagcttc gaattcacca tggtgcgatg      60
cgaccgcggg ctgcagatgc tgctgaccac ggctggagcc ttcgccgcct tctcgctcat     120
ggccatcgcc atcggcactg actactggct gtactccagc gcgcacatct gcaacggcac     180
caacctgacc atggacgacg ggccccgcc ccgccgcgcc cgcggcgacc tcacccattc      240
gggactgtgg cgggtgtgtt gcatcgaagg catctacaag gggcactgct tccggatcaa     300
ccacttccca gaggacaacg attatgacca cgacagctcc gagtacctcc tccgcattgt     360
gcgagcctcc agtgtcttcc ccatcctcag caccattctg ctcctgcttg gagggctctg     420
catcggcgct gggaggatct acagccgcaa gaacaacatt gtcctcagtg caggaatcct     480
ctttgtggct gcaggcctca gtaatatcat cggcatcatc gtctaccggc attccgtcag     540
agccctgctg caggggtca accctgagac ccctccagct ccacgcctgg cctatgagta      600
ttcctggtcc ctaggctgtg gtgtgggcgc tggtctaatc ctgctgctgg ggggagtctg     660
tttcctcctg ctcacccctgc cttcctggcc ctggaggtca ctgtgcccca gcgggggtgg    720
cccaactgcc tagaagccga attctgcagt cgacggtacc gcgggcccgg gatccaccgg     780
atctagataa ctgatc                                                    796

<210> SEQ ID NO 7
<211> LENGTH: 1169
<212> TYPE: DNA
<213> ORGANISM: Artificial
<220> FEATURE:
<223> OTHER INFORMATION: Synthetic construct, gamma 6664

<400> SEQUENCE: 7
atcaagctta tcgataccgt cgacctcgag ctcaagcttc gaattcggct tatgatgtgg      60
tctaacttct tcatgcaaga ggaagaccgt cgtcggacgg ctgtgggccg gcgtcgtgcc     120
caagaacagc agaatctcgg cttgactccg gagcgagagg gcaagatcaa gctggggttg     180
ctggtggcta tcgtgggtgc cactctggct gtgctagctg tgggcaccga gttctgggtg     240
gaactcaata catacaagac caacggcagc gccgtctgtg aggccgccca tttggggctg     300
tggaaggtgt gcatcaagcg actgtggcag gcggatgtac ccgcgggcag ggagacctgt     360
ggcccagctg agctgccagg agaagcaaac tgcaccctact tcaagttctt caccacgggg     420
gaaaatgcgc acatcttcca gagaaccacc aagaaagagg taaacctggc agctgctgtg     480
atagctgtgc tgggcctgac agccatggcc ttgggctgcc tctgtgtcat catggtgctc     540
agtaaaggtg cagagttcct gctccgcttg ggagctgtct gctttggcct ctcaggcctg     600
ctgctctttg tcagcctgga ggtgttccgg cattccgtca gagccctgct gcagaaccat     660
tacaactacg gctggtcttt ttactttgga gccctgtcgt ttattgtggc ggagaccgtg     720
ggcgttctgg ctgtaaacat ttacattgag aaaaacaaag agttgaggtt taagaccaag     780
cgggagttcc tcaaggcctc ttcctcctct ccttactcca ggatgccgag ttacaggtac     840
cggcgacggc gctccaggtc cagttcgagg tccactgagg cctcaccctc tagagatgcc     900
tctcctgtgg gcctgaagat cacggggggcc attcccatgg gtgagctgtc catgtacacg     960
ctgtccagag aaccccctcaa ggtgaccaca gctgccagct acagtccgga tcaggatgct    1020
ggcttcctac agatgcatga cttcttccaa caggacctaa aggagggttt ccacgtcagc    1080
atgctgaacc gacggacgac ccctgtgtga cgaattctgc agtcgacggt accgcgggcc    1140
```

```
cgggatccac cggatctaga taactgatc                                     1169

<210> SEQ ID NO 8
<211> LENGTH: 790
<212> TYPE: DNA
<213> ORGANISM: Artificial
<220> FEATURE:
<223> OTHER INFORMATION: Synthetic construct, gamma 4666

<400> SEQUENCE: 8
atcaagctta tcgataccgt cgacctcgag ctcaagcttc gaattcacca tggtgcgatg       60
cgaccgcggg ctgcagatgc tgctgaccac ggctggagcc ttcgccgcct tctcgctcat      120
ggccatcgcc atcggcactg actactggct gtactccagc gcgcacatct gcaacggcac      180
caacctgacc atggacgacg ggcccccgcc ccgccgcgcc cgcggcgacc tcacccattc      240
gggactgtgg cgggtgtgtt gcatcgaagg catctacaag gggcactgct tccggatcaa      300
ccacttccca gaggacaacg attatgacca cgacagctcc gagtacctcc tccgcattgt      360
gccagctgct gtgatagctg tgctgggcct gacagccatg gccttgggct gcctctgtgt      420
catcatggtg ctcagtaaag gtgcagagtt cctgctccgc ttgggagctg tctgctttgg      480
cctctcaggc ctgctgctct ttgtcagcct ggaggtgttc cggcattccg tcagagccct      540
gctgcagggg gtcaaccctg agaccccctcc agctccacgc ctggcctatg agtattcctg      600
gtccctaggc tgtggtgtgg gcgctggtct aatcctgctg ctgggggag tctgtttcct      660 cctgctcacc ctgccttcct ggccctggag gtcactgtgc ccaagcgggg gtggcccaac      720
tgcctagaag ccgaattctg cagtcgacgg taccgcgggc ccgggatcca ccggatctag      780
ataactgatc                                                              790

<210> SEQ ID NO 9
<211> LENGTH: 873
<212> TYPE: DNA
<213> ORGANISM: Artificial
<220> FEATURE:
<223> OTHER INFORMATION: Synthetic construct, gamma 6446

<400> SEQUENCE: 9
atcaagctta tcgataccgt cgacctcgag ctcaagcttc gaattcggct tatgatgtgg       60
tctaacttct tcatgcaaga ggaagaccgt cgtcggacgg ctgtgggccg gcgtcgtgcc      120
caagaacagc agaatctcgg cttgactccg gagcgagagg gcaagatcaa gctgggggttg      180 ctggtggcta tcgtgggtgc cactctggct gtgctagctg tgggcaccga gttctgggtg      240
gaactcaata catacaagac caacggcagc gccgtctgtg aggccgccca tttgggggctg      300 tggaaggtgt gcatcaagcg actgtggcag gcggatgtac ccgcgggcat ctacaagggg      360
cactgcttcc ggatcaacca cttcccagag acaacgatt atgaccacga cagctccgag      420
tacctcctcc gcattgtgcg agcctccagt gtcttcccca tcctcagcac cattctgctc      480
ctgcttggag ggctctgcat cggcgctggg aggatctaca gccgcaagaa caacattgtc      540
ctcagtgcag gaatcctctt tgtggctgca ggcctcagta atatcatcgg catcatcgtc      600
taccggcatt ccgtcagagc cctgctgcag ggggtcaacc ctgagacccc tccagctcca      660
cgcctggcct atgagtattc ctggtcccta ggctgtggtg tgggcgctgg tctaatcctg      720
ctgctggggg gagtctgttt cctcctgctc accctgcctt cctggccctg gaggtcactg      780
tgccccaagc ggggtggccc aactgcctag aagccgaatt ctgcagtcga cggtaccgcg      840
ggcccgggat ccaccggatc tagataactg atc                                   873
```

<210> SEQ ID NO 10
<211> LENGTH: 805
<212> TYPE: DNA
<213> ORGANISM: Artificial
<220> FEATURE:
<223> OTHER INFORMATION: Synthetic construct, gamma 4.6666

<400> SEQUENCE: 10

| | | | | | |
|---|---|---|---|---|---|
| atcaagctta | tcgataccgt | cgacctcgag | ctcaagcttc | gaattcacca | tggtgcgatg | 60 |
| cgaccgcggg | ctgcagatgc | tggggttgct | ggtggctatc | gtgggtgcca | ctctggctgt | 120 |
| gctagctgtg | ggcaccgagt | tctgggtgga | actcaataca | tacaagacca | acggcagcgc | 180 |
| cgtctgtgag | gccgcccatt | tggggctgtg | gaaggtgtgc | atcaagcgac | tgtggcaggc | 240 |
| ggatgtaccc | gcgggcaggg | agacctgtgg | cccagctgag | ctgccaggag | aagcaaactg | 300 |
| cacctacttc | aagttcttca | ccacggggga | aaatgcgcac | atcttccaga | gaaccaccaa | 360 |
| gaaagaggta | aacctggcag | ctgctgtgat | agctgtgctg | gcctgacag | ccatggcctt | 420 |
| gggctgcctc | tgtgtcatca | tggtgctcag | taaaggtgca | gagttcctgc | tccgcttggg | 480 |
| agctgtctgc | tttggcctct | caggcctgct | gctctttgtc | agcctggagg | tgttccggca | 540 |
| ttccgtcaga | gccctgctgc | aggggggtcaa | ccctgagacc | cctccagctc | acgcctggc | 600 |
| ctatgagtat | tcctggtccc | taggctgtgg | tgtgggcgct | ggtctaatcc | tgctgctggg | 660 |
| gggagtctgt | ttcctcctgc | tcaccctgcc | ttcctggccc | tggaggtcac | tgtgccccaa | 720 |
| gcggggtggc | ccaactgcct | agaagccgaa | ttctgcagtc | gacggtaccg | cgggcccggg | 780 |
| atccaccgga | tctagataac | tgatc | | | | 805 |

<210> SEQ ID NO 11
<211> LENGTH: 760
<212> TYPE: DNA
<213> ORGANISM: Artificial
<220> FEATURE:
<223> OTHER INFORMATION: Synthetic construct, gamma 6 N-terminal deleted

<400> SEQUENCE: 11

| | | | | | |
|---|---|---|---|---|---|
| atcaagctta | tcgataccgt | cgacctcgag | catgctgggg | ttgctggtgg | ctatcgtggg | 60 |
| tgccactctg | gctgtgctag | ctgtgggcac | cgagttctgg | gtggaactca | atacatacaa | 120 |
| gaccaacggc | agcgccgtct | gtgaggccgc | ccatttgggg | ctgtggaagg | tgtgcatcaa | 180 |
| gcgactgtgg | caggcggatg | tacccgcggg | caggagacc | tgtggcccag | ctgagctgcc | 240 |
| aggagaagca | aactgcacct | acttcaagtt | cttcaccacg | ggggaaaatg | cgcacatctt | 300 |
| ccagagaacc | accaagaaag | aggtaaacct | ggcagctgct | gtgatagctg | tgctgggcct | 360 |
| gacagccatg | gccttgggct | gcctctgtgt | catcatggtg | ctcagtaaag | gtgcagagtt | 420 |
| cctgctccgc | ttgggagctg | tctgctttgg | cctctcaggc | ctgctgctct | ttgtcagcct | 480 |
| ggaggtgttc | cggcattccg | tcagagccct | gctgcagggg | gtcaaccctg | agacccctcc | 540 |
| agctccacgc | ctggcctatg | agtattcctg | gtccctaggc | tgtggtgtgg | gcgctggtct | 600 |
| aatcctgctg | ctggggggag | tctgtttcct | cctgctcacc | ctgccttcct | ggccctggag | 660 |
| gtcactgtgc | ccaagcgggg | tggcccaac | tgcctagaag | ccgaattctg | cagtcgacgg | 720 |
| taccgcgggc | ccgggatcca | ccggatctag | ataactgatc | | | 760 |

<210> SEQ ID NO 12
<211> LENGTH: 20
<212> TYPE: PRT
<213> ORGANISM: Artificial

<220> FEATURE:
<223> OTHER INFORMATION: Synthetic construct

<400> SEQUENCE: 12

```
Lys Leu Gly Leu Leu Val Ala Ile Val Gly Ala Thr Leu Ala Val Leu
1               5                   10                  15

Ala Val Gly Thr
            20
```

<210> SEQ ID NO 13
<211> LENGTH: 20
<212> TYPE: PRT
<213> ORGANISM: Artificial
<220> FEATURE:
<223> OTHER INFORMATION: Synthetic construct

<400> SEQUENCE: 13

```
Arg Val Thr Leu Phe Phe Ile Leu Ala Gly Gly Val Leu Ala Met Val
1               5                   10                  15

Ala Val Val Thr
            20
```

<210> SEQ ID NO 14
<211> LENGTH: 20
<212> TYPE: PRT
<213> ORGANISM: Artificial
<220> FEATURE:
<223> OTHER INFORMATION: Synthetic construct

<400> SEQUENCE: 14

```
Leu Ile Thr Thr Val Gly Ala Phe Ala Ala Phe Ser Leu Met Thr Ile
1               5                   10                  15

Ala Val Gly Thr
            20
```

<210> SEQ ID NO 15
<211> LENGTH: 20
<212> TYPE: PRT
<213> ORGANISM: Artificial
<220> FEATURE:
<223> OTHER INFORMATION: Synthetic construct

<400> SEQUENCE: 15

```
Leu Leu Thr Thr Val Gly Ala Phe Ala Ala Phe Ser Leu Met Thr Ile
1               5                   10                  15

Ala Val Gly Thr
            20
```

<210> SEQ ID NO 16
<211> LENGTH: 20
<212> TYPE: PRT
<213> ORGANISM: Artificial
<220> FEATURE:
<223> OTHER INFORMATION: Synthetic construct

<400> SEQUENCE: 16

```
Leu Leu Thr Thr Ile Gly Ala Phe Ala Ala Phe Gly Leu Met Thr Ile
1               5                   10                  15

Ala Ile Ser Thr
            20
```

<210> SEQ ID NO 17
<211> LENGTH: 20
<212> TYPE: PRT
<213> ORGANISM: Artificial

```
<220> FEATURE:
<223> OTHER INFORMATION: Synthetic construct

<400> SEQUENCE: 17

Leu Leu Thr Thr Ala Gly Ala Phe Ala Ala Phe Ser Leu Met Ala Ile
1               5                   10                  15

Ala Ile Gly Thr
            20

<210> SEQ ID NO 18
<211> LENGTH: 20
<212> TYPE: PRT
<213> ORGANISM: Artificial
<220> FEATURE:
<223> OTHER INFORMATION: Synthetic construct

<400> SEQUENCE: 18

Leu Leu Ser Ser Val Phe Gly Ala Cys Gly Leu Leu Val Gly Ile
1               5                   10                  15

Ala Val Ser Thr
            20

<210> SEQ ID NO 19
<211> LENGTH: 20
<212> TYPE: PRT
<213> ORGANISM: Artificial
<220> FEATURE:
<223> OTHER INFORMATION: Synthetic construct

<400> SEQUENCE: 19

Leu Leu Ser Ser Val Phe Ala Val Cys Gly Leu Gly Leu Leu Gly Ile
1               5                   10                  15

Ala Val Ser Thr
            20

<210> SEQ ID NO 20
<211> LENGTH: 20
<212> TYPE: PRT
<213> ORGANISM: Artificial
<220> FEATURE:
<223> OTHER INFORMATION: Synthetic construct

<400> SEQUENCE: 20

Lys Leu Leu Leu Leu Val Ala Ile Val Gly Ala Thr Leu Ala Val Leu
1               5                   10                  15

Ala Val Gly Thr
            20

<210> SEQ ID NO 21
<211> LENGTH: 20
<212> TYPE: PRT
<213> ORGANISM: Artificial
<220> FEATURE:
<223> OTHER INFORMATION: Synthetic construct

<400> SEQUENCE: 21

Lys Leu Gly Leu Leu Val Ala Ile Val Leu Ala Thr Leu Ala Val Leu
1               5                   10                  15

Ala Val Gly Thr
            20

<210> SEQ ID NO 22
<211> LENGTH: 20
<212> TYPE: PRT
<213> ORGANISM: Artificial
```

```
<220> FEATURE:
<223> OTHER INFORMATION: Synthetic construct

<400> SEQUENCE: 22

Leu Leu Thr Thr Ala Gly Ala Phe Ala Ala Phe Ser Gly Met Ala Ile
1               5                   10                  15

Ala Ile Gly Thr
            20

<210> SEQ ID NO 23
<211> LENGTH: 18
<212> TYPE: DNA
<213> ORGANISM: Artificial
<220> FEATURE:
<223> OTHER INFORMATION: Synthetic construct

<400> SEQUENCE: 23
aaatggtggt gaagatgg                                                 18

<210> SEQ ID NO 24
<211> LENGTH: 18
<212> TYPE: DNA
<213> ORGANISM: Artificial
<220> FEATURE:
<223> OTHER INFORMATION: Synthetic construct

<400> SEQUENCE: 24
gacgaagaaa cagagcag                                                 18

<210> SEQ ID NO 25
<211> LENGTH: 19
<212> TYPE: DNA
<213> ORGANISM: Artificial
<220> FEATURE:
<223> OTHER INFORMATION: Synthetic construct

<400> SEQUENCE: 25
gaggactgat gaccccaac                                                19

<210> SEQ ID NO 26
<211> LENGTH: 18
<212> TYPE: DNA
<213> ORGANISM: Artificial
<220> FEATURE:
<223> OTHER INFORMATION: Synthetic construct

<400> SEQUENCE: 26
atgatccggt gacacagg                                                 18

<210> SEQ ID NO 27
<211> LENGTH: 24
<212> TYPE: DNA
<213> ORGANISM: Artificial
<220> FEATURE:
<223> OTHER INFORMATION: Synthetic construct

<400> SEQUENCE: 27
tcccccgtct acttcgtcac cttc                                          24

<210> SEQ ID NO 28
<211> LENGTH: 25
<212> TYPE: DNA
<213> ORGANISM: Artificial
<220> FEATURE:
<223> OTHER INFORMATION: Synthetic construct

<400> SEQUENCE: 28
```
gcgagagcat cctggacaca gatac					25

<210> SEQ ID NO 29
<211> LENGTH: 21
<212> TYPE: DNA
<213> ORGANISM: Artificial
<220> FEATURE:
<223> OTHER INFORMATION: Synthetic construct

<400> SEQUENCE: 29
gaccatcggg aacatcgtaa t					21

<210> SEQ ID NO 30
<211> LENGTH: 21
<212> TYPE: DNA
<213> ORGANISM: Artificial
<220> FEATURE:
<223> OTHER INFORMATION: Synthetic construct

<400> SEQUENCE: 30
ggaagaggcg aagaaagtg a					21

<210> SEQ ID NO 31
<211> LENGTH: 18
<212> TYPE: DNA
<213> ORGANISM: Artificial
<220> FEATURE:
<223> OTHER INFORMATION: Synthetic construct

<400> SEQUENCE: 31
accagcaaga agaacgag					18

<210> SEQ ID NO 32
<211> LENGTH: 18
<212> TYPE: DNA
<213> ORGANISM: Artificial
<220> FEATURE:
<223> OTHER INFORMATION: Synthetic construct

<400> SEQUENCE: 32
agacacgaag aagatgcc					18

<210> SEQ ID NO 33
<211> LENGTH: 19
<212> TYPE: DNA
<213> ORGANISM: Artificial
<220> FEATURE:
<223> OTHER INFORMATION: Synthetic construct

<400> SEQUENCE: 33
caagtgacaa tgaaaccag					19

<210> SEQ ID NO 34
<211> LENGTH: 18
<212> TYPE: DNA
<213> ORGANISM: Artificial
<220> FEATURE:
<223> OTHER INFORMATION: Synthetic construct

<400> SEQUENCE: 34
agagacgaag aagatgcc					18

<210> SEQ ID NO 35
<211> LENGTH: 19
<212> TYPE: DNA
<213> ORGANISM: Artificial

```
<220> FEATURE:
<223> OTHER INFORMATION: Synthetic construct

<400> SEQUENCE: 35
tgacgaagac aaaaagaac                                                  19

<210> SEQ ID NO 36
<211> LENGTH: 19
<212> TYPE: DNA
<213> ORGANISM: Artificial
<220> FEATURE:
<223> OTHER INFORMATION: Synthetic construct

<400> SEQUENCE: 36
taaggagagg aggaagagg                                                  19

<210> SEQ ID NO 37
<211> LENGTH: 19
<212> TYPE: DNA
<213> ORGANISM: Artificial
<220> FEATURE:
<223> OTHER INFORMATION: Synthetic construct

<400> SEQUENCE: 37
cataatcctc ccacagaac                                                  19

<210> SEQ ID NO 38
<211> LENGTH: 17
<212> TYPE: DNA
<213> ORGANISM: Artificial
<220> FEATURE:
<223> OTHER INFORMATION: Synthetic construct

<400> SEQUENCE: 38
tacacagaca tcacccc                                                    17

<210> SEQ ID NO 39
<211> LENGTH: 20
<212> TYPE: DNA
<213> ORGANISM: Artificial
<220> FEATURE:
<223> OTHER INFORMATION: Synthetic construct

<400> SEQUENCE: 39
agctgccagg agaagcaaac                                                 20

<210> SEQ ID NO 40
<211> LENGTH: 21
<212> TYPE: DNA
<213> ORGANISM: Artificial
<220> FEATURE:
<223> OTHER INFORMATION: Synthetic construct

<400> SEQUENCE: 40
ctctgcacct ttactgagca c                                               21

<210> SEQ ID NO 41
<211> LENGTH: 20
<212> TYPE: DNA
<213> ORGANISM: Artificial
<220> FEATURE:
<223> OTHER INFORMATION: Synthetic construct

<400> SEQUENCE: 41
tggtgacgga aaacacggag                                                 20
```

```
<210> SEQ ID NO 42
<211> LENGTH: 21
<212> TYPE: DNA
<213> ORGANISM: Artificial
<220> FEATURE:
<223> OTHER INFORMATION: Synthetic construct

<400> SEQUENCE: 42
agaaaagagg aagcagcgaa g                                              21

<210> SEQ ID NO 43
<211> LENGTH: 18
<212> TYPE: DNA
<213> ORGANISM: Artificial
<220> FEATURE:
<223> OTHER INFORMATION: Synthetic construct

<400> SEQUENCE: 43
ggagtcattg aaacgctg                                                  18

<210> SEQ ID NO 44
<211> LENGTH: 17
<212> TYPE: DNA
<213> ORGANISM: Artificial
<220> FEATURE:
<223> OTHER INFORMATION: Synthetic construct

<400> SEQUENCE: 44
tcatcacctg ctgtgag                                                   17

<210> SEQ ID NO 45
<211> LENGTH: 20
<212> TYPE: DNA
<213> ORGANISM: Artificial
<220> FEATURE:
<223> OTHER INFORMATION: Synthetic construct

<400> SEQUENCE: 45
ctgcgaaagg caaggaggaa                                                20

<210> SEQ ID NO 46
<211> LENGTH: 20
<212> TYPE: DNA
<213> ORGANISM: Artificial
<220> FEATURE:
<223> OTHER INFORMATION: Synthetic construct

<400> SEQUENCE: 46
tggctccacg atcctcagca                                                20

<210> SEQ ID NO 47
<211> LENGTH: 984
<212> TYPE: DNA
<213> ORGANISM: Rattus norvegicus

<400> SEQUENCE: 47
atggtgcgat gcgaccgcgg gctgcagatg ctgctgacca cggctggagc cttcgccgcc     60
ttctcgctca tggccatcgc catcggcact gactactggc tgtactccag cgcgcacatc    120
tgcaacggca ccaacctgac catggacgac gggccccccgc cccgccgcgc ccgcggcgac    180
ctcacccatt cgggactgtg cgggtgtgt tgcatcgaag catctacaa ggggcactgc      240 ttccggatca accacttccc agaggacaac gattatgacc acgacagctc cgagtacctc    300
ctccgcattg tgcgagcctc cagtgtcttc cccatcctca gcaccattct gctcctgctt    360
ggagggctct gcatcggcgc tgggaggatc tacagccgca agaacaacat tgtcctcagt    420
```

-continued

```
gcaggaatcc tctttgtggc tgcaggcctc agtaatatca tcggcatcat cgtctacatt    480
tccagcaaca cgggcgaccc cagtgacaag cgtgacgaag acaagaagaa ccattacaac    540
tacggctggt cttttactt tggagccctg tcgtttattg tggcgagac cgtgggcgtt     600 ctggctgtaa acatttacat tgagaaaaac aaagagttga ggtttaagac caagcgggag    660
ttcctcaagg cctcttcctc ctctccttac tccaggatgc cgagttacag gtaccggcga    720
cggcgctcca ggtccagttc gaggtccact gaggcctcac cctctagaga tgcctctcct    780
gtgggcctga agatcacggg ggccattccc atgggtgagc tgtccatgta cacgctgtcc    840
agagaacccc tcaaggtgac cacagctgcc agctacagtc cggatcagga tgctggcttc    900
ctacagatgc atgacttctt ccaacaggac ctaaaggagg gtttccacgt cagcatgctg    960
aaccgacgga cgaccctgt gtga                                            984

<210> SEQ ID NO 48
<211> LENGTH: 783
<212> TYPE: DNA
<213> ORGANISM: Rattus norvegicus

<400> SEQUENCE: 48
atgatgtggt ctaacttctt catgcaagag gaagaccgtc gtcggacggc tgtgggccgg     60
cgtcgtgccc aagaacagca gaatctcggc ttgactccgg agcgagaggg caagatcaag    120
ctggggttgc tggtggctat cgtgggtgcc actctggctg tgctagctgt gggcaccgag    180
ttctgggtgg aactcaatac atacaagacc aacggcagcg ccgtctgtga ggccgcccat    240
ttggggctgt ggaaggtgtg catcaagcga ctgtggcagg cggatgtacc cgcgggcagg    300
gagacctgtg gcccagctga gctgccagga gaagcaaact gcacctactt caagttcttc    360
accacggggg aaaatgcgca catcttccag agaaccacca gaaagaggt aaacctggca    420 gctgctgtga tagctgtgct gggcctgaca gccatggcct tgggctgcct ctgtgtcatc    480
atggtgctca gtaaaggtgc agagttcctg ctccgcttgg gagctgtctg ctttggcctc    540
tcaggcctgc tgctctttgt cagcctggag gtgttccggc attccgtcag agccctgctg    600
cagggggtca accctgagac ccctccagct ccacgcctgg cctatgagta ttcctggtcc    660
ctaggctgtg gtgtgggcgc tggtctaatc ctgctgctgg ggggagtctg tttcctcctg    720
ctcaccctgc cttcctggcc ctggaggtca ctgtgcccca gcgggtgg cccaactgcc     780 tag                                                                   783

<210> SEQ ID NO 49
<211> LENGTH: 645
<212> TYPE: DNA
<213> ORGANISM: Rattus norvegicus

<400> SEQUENCE: 49
atgatgtggt ctaacttctt catgcaagag gaagaccgtc gtcggacggc tgtgggccgg     60
cgtcgtgccc aagaacagca gaatctcggc ttgactccgg agcgagaggg caagatcaag    120
ctggggttgc tggtggctat cgtgggtgcc actctggctg tgctagctgt gggcaccgag    180
ttctgggtgg aactcaatac atacaagacc aacggcagcg ccgtctgtga ggccgcccat    240
ttggggctgt ggaaggtgtg catcaagcga ctgtggcagg cggatgtacc cgcgggcagg    300
gagacctgtg gcccagctga gctgccagga gaagcaaact gcacctactt caagttcttc    360
accacggggg aaaatgcgca catcttccag agaaccacca gaaaggcct gctgctcttt    420 gtcagcctgg aggtgttccg gcattccgtc agagccctgc tgcaggggt caaccctgag    480
```

```
accoctocag ctccacgcct ggcctatgag tattcctggt ccctaggctg tggtgtgggc      540
gctggtctaa tcctgctgct ggggggagtc tgtttcctcc tgctcaccct gccttcctgg      600
ccctggaggt cactgtgccc caagcggggt ggcccaactg cctag                      645

<210> SEQ ID NO 50
<211> LENGTH: 828
<212> TYPE: DNA
<213> ORGANISM: Rattus norvegicus

<400> SEQUENCE: 50
atgagtcact gcagcagccg cgccctgacc ctgctgagca gcgtgtttgg tgcctgcggc       60
ctgctccttg tgggcatcgc ggtcagcacg gactactggc tgtatatgga ggaggggacc      120
gttttgccgc agaaccagac caccgaggtc aagatggcgc tgcacgctgg cctctggaga      180
gtctgcttct ttgcaggtcg ggagaagggg cgctgtgtgg cttctgagta ctttcttgaa      240
ccagagatca acttggtgac ggaaaacacg gagaatattc tgaagacagt acgcacggct      300 acaccttcc ctatggtcag tctcttcctt gtgttcaccg ccttcgtcat cagcaacatc       360
ggccacatcc gacctcagag gaccattctt gccttcgttt ctggcatctt tttcatttta      420
tcaggcctct ccttggtggt gggcttggtt ctatacatct ctagcatcaa cgatgaggtc      480
atgaacaggc ccagcagctc tgagcaatac tttcactatc gctacgggtg gtcgtttgcc      540
ttcgctgctt cttcctttct tctgaaagag ggggccggag tcatgtccgt gtacttattc      600
accaagcgct acgcggagga ggagatgtat cgcccgcacc cggccttcta ccgaccgcgt      660
ctcagcgact gctccgacta ctcgggccag tttctgcaac ccgaagcgtg gcgtcgtggc      720
cgcagccctt ccgacatttc tagcgacgtc tccatccaga tgacgcaaaa ttaccctccg      780
gccatcaagt acccggacca cctccacatc tccacttcac cctgctga                   828
```

PEPTIDES AND CALCIUM REGULATION IN MAMMALIAN CELLS

CROSS-REFERENCES TO RELATED APPLICATIONS

This application claims the benefit under 35 USC 119(e) of U.S. Provisional Patent Application Ser. 60/722,707 filed Sep. 30, 2005, which is incorporated by reference in entirety.

STATEMENT ON FEDERALLY SPONSORED RESEARCH OR DEVELOPMENT

This invention was made, at least in part, with government support under NIH Grant R01 AR44352 awarded by the National Institutes of Health. The government has certain rights in the invention.

BACKGROUND OF THE INVENTION

Voltage dependent calcium channels (VDCCs) are multimeric proteins that reside in the surface membranes of cells. When activated they allow calcium ions to move into the cell and thus contribute to the regulation of a wide range of cellular functions and physiological processes. For instance, the activation of voltage dependent calcium channels contributes to the electrical excitability and normal function of the brain, the release of neurotransmitters, the transmission of pain signals, skeletal and cardiac muscle contraction, the regulation of gene expression, cell motility, division, and development. Agents with the ability to alter calcium channel function have the potential to modify such important cellular and physiological processes.

Structurally, VDCCs are heteromeric proteins consisting of a pore-forming $\alpha_1$ subunit and, potentially, as many as three auxiliary subunits: $\alpha_2\delta$, $\beta$ and $\gamma$. The $\alpha_1$ subunit contains the permeation pathway for calcium ions and the voltage sensing regions that control channel gating. Thus they determine to a great extent the major characteristics of the calcium current carried by the different calcium channel subtypes. The auxiliary subunits act, in a sense, as regulators of VDCC current. For instance, when co-expressed with an $\alpha_1$ subunit the auxiliary subunits $\alpha_2\delta$ and $\beta$ act as positive regulators of calcium channel function. They enhance trafficking of the channel complex to the surface membrane thus increasing current density. They also alter the biophysical properties of the channel in ways that enhance activation. Two of the eight known $\gamma$ subunits ($\gamma_1$ and $\gamma_6$) seem to function primarily as negative regulators of calcium current. When co-expressed with calcium channel $\alpha_1$ subunits, $\gamma_1$ and $\gamma_6$ decrease calcium current density.

The unique ability of the $\gamma_6$ subunit to decrease calcium current in cells forms the basis for this invention. To address the need for new agents capable of regulating calcium transport, we report new compositions and methods for control of calcium channel function.

SUMMARY OF THE INVENTION

In general the terms and phrases used herein have their art-recognized meaning, which can be found by reference to standard texts, journal references and contexts known to those skilled in the art. The following definitions are provided to clarify their specific use in the context of the invention.

GXXXG-like motif. When used herein, the term refers to a peptide structural motif that has an initial and a terminal amino acid wherein each independently has a small side chain. Examples of amino acids with small side chains include glycine (G), alanine (A), and serine (S). A particular example of a GxxxG-like motif is GxxxA.

Cav. When used herein, the term refers to voltage dependent calcium channels. Particular designations in the format $Ca_vZZ$ (such as Cav3.1) indicate gene names for alpha1 subunits of voltage dependent calcium channels.

The following abbreviations are applicable. $\alpha$, alpha; $\beta$, beta; $\delta$, delta; $\gamma$, gamma; $\tau$, tau; LVA, low voltage-activated; TM, transmembrane; Cav, Calcium ion regulated by voltage; $V_{0.5}$, half-maximal potentials.

It is recognized that regardless of the ultimate correctness of any mechanistic explanation or hypothesis, an embodiment of the invention can nonetheless be operative and useful.

The invention broadly provides compositions and methods for modification of calcium regulation. In embodiments, the invention provides compositions and methods relating to the ability of calcium channels to mediate calcium current.

We have generally used protein engineering as well as cell biological and electrophysiological approaches to identify a specific region in the gamma6 subunit capable of effecting calcium regulation. In an embodiment, the region is both necessary and sufficient for its action as a negative regulator of calcium current.

In an embodiment, the invention provides peptides that can be used to regulate the density of calcium current in cells. In a particular embodiment, the peptide is a segment of one of the four subunits that can contribute to forming the native calcium channel in excitable cells. In an embodiment, a peptide of the invention is capable of effecting a reduction in calcium current. In a particular embodiment, the reduction of calcium current can be from about 10% to about 90%. In a particular embodiment, expression of the peptide within a cell can reduce the normal calcium current by about 20% to about 80%. In a particular embodiment, the reduction is about 30% to about 50%. In an embodiment, the peptide inhibits calcium current generated by $Ca_v3.1$, $Ca_v2.3$, and $Ca_v3.2$ calcium channels. In an embodiment, the peptide inhibits calcium current generated by any one or more of all of the known gene families (e.g., $Ca_v1$, $Ca_v2$, and $Ca_v3$) that are capable of encoding mammalian calcium channels.

In an embodiment, the invention provides a peptide agent to decrease calcium current density in cells. In an embodiment, the agent is introduced as an exogenous composition. In an embodiment, the agent is delivered via endogenous expression in a cell. In an embodiment, a targeted knockout of the subunit from which the peptide is derived is used to modify a calcium channel property, for example by increasing calcium current density. In an embodiment, a peptide agent selectively affects voltage dependent ion currents.

In an embodiment, a short, lipophilic region has been identified in a naturally occurring gamma6 protein that is capable of decreasing voltage dependent calcium current. In a particular embodiment, a GxxxA motif (or other motif as described herein) within a gamma6 peptide is required for functional activity. In a particular embodiment, a GxxxA motif is utilized within a native context in a gamma6 peptide. In an embodiment, the motif is introduced into a foreign receiving peptide (other than the native gamma6 peptide) or foreign position within a gamma6 receiving peptide to confer a different ability on the receiving peptide to regulate calcium. In an embodiment, a relative location of the motif within a peptide fragment can determine the selectivity of action on different types of calcium current. For example, selectivity can be achieved based on whether the current is high voltage gated or low voltage gated.

In an embodiment, a peptide length is from about 10 amino acids to about 40 amino acids. In a preferred embodiment, the peptide length is from about 20 amino acids. In a particular embodiment, the peptide modifies a calcium channel function. In a further particular embodiment, the peptide decreases current in a mammalian cell. In an embodiment, the mammalian cell is a neuron or myocyte.

In an embodiment, the peptide is a fragment of the gamma6 isoform of the gamma subunit of voltage dependent calcium channels. In an embodiment, the peptide utilizes a native sequence from a rat, human, or mouse source or a variant sequence. In an embodiment, the peptide has an amino acid homology of at least about 80%, 85%, 90%, or 95% to the rat, human, or mouse source. In an embodiment, the gamma6 subunit peptide is co-expressed with a pore forming subunit of a calcium channel. In an embodiment, the co-expression involves at least one other auxiliary subunit of a calcium channel. In an embodiment, the coexpression modifies a calcium channel function. In a preferred embodiment, the coexpression decreases calcium current. In particular embodiments, a gamma6 TM1 (transmembrane domain 1), or a fragment or fragment variant thereof, mediates a relative decrease in calcium current.

In an embodiment, a peptide of the invention is a relatively short portion of a naturally occurring calcium channel protein that is expressed in humans and other mammals. In an embodiment, the peptide has less than 20% of the normal sequence length of a native gamma6 protein. In a preferred embodiment, the peptide has less than 10% of the normal sequence length of a native gamma6 protein. In an embodiment, a peptide of the invention is lipophilic. In an embodiment, a peptide is readily able to incorporate into a cellular membrane.

In an embodiment, a peptide is used as a therapeutic agent for the treatment of a disorder relating to dysfunctional calcium regulation.

In an embodiment, a peptide is provided in isolated or purified form. In an embodiment, the invention provides nucleic acid sequences (DNA and RNA) capable of encoding peptides of the invention. In an embodiment, a nucleic acid is provided in isolated or purified form. In an embodiment, the invention provides a genetic construct containing a segment capable of encoding a peptide of the invention. In an embodiment, the invention provides a host cell comprising said genetic construct.

In an embodiment, the invention provides an isolated calcium channel gamma6 subunit peptide comprising an N-terminal transmembrane domain or continuous fragment thereof of at least about 5 to 15 amino acids, preferably at least 15 amino acids. In an embodiment, the N-terminal transmembrane domain is the first transmembrane domain. In an embodiment, the peptide has a total length of about 5 to 40, preferably of about 15 to 40 amino acids. In a particular embodiment, the peptide has a total length of about 20 amino acids. In an embodiment, the peptide is capable of modifying an ability of a calcium channel to regulate calcium in a cell. In a preferred embodiment, the ability is to regulate calcium current. In a particular embodiment, the calcium channel is a low voltage activated channel. In a particular embodiment, the calcium channel is a high voltage activated channel.

In an embodiment, a peptide of the invention has a homology level of about at least 80% to a gamma6 subunit amino acid sequence from a human source. In an embodiment, a peptide has a homology level of about at least 80% to a gamma6 subunit amino acid sequence from a rat source. In an embodiment, a peptide has a homology level of about at least 80% to a gamma6 subunit amino acid sequence from a mouse source.

In an embodiment, a peptide of the invention comprises a GxxxG-like structural motif (SEQ ID NO:1). In a particular embodiment, the GxxxG-like motif has a GxxxA sequence (SEQ ID NO:2) of amino acids. In an embodiment, a peptide comprises a structural motif of X1-X2-X3-X4-X5, wherein X1 and X5 independently are an amino acid with a relatively small side chains. In a particular embodiment, X1 and X5 are independently glycine, alanine, or serine. In a particular embodiment, X2, X3, and X4 independently are each any amino acid. In a particular embodiment, X2, X3, and X4 are independently selected from the group consisting of leucine, valine, phenylalanine, glycine, threonine, isoleucine, alanine, and serine (one-letter code: L, V, F, G, T, I, A, S). In an embodiment, X1 is G or A. In a preferred embodiment, X1 is G.

In an embodiment, a peptide of the invention comprises a structural groove along at least a portion of a three-dimensional projection of the peptide, wherein said groove is capable of facilitating an interaction with at least one other calcium channel subunit protein.

In an embodiment, the invention provides a nucleic acid encoding a peptide as described herein.

In an embodiment, the invention provides a method of modifying an ability of a calcium channel to regulate calcium in a cell, comprising exposing said cell to a purified calcium channel gamma6 subunit peptide. In an embodiment, the invention provides a method of decreasing calcium current in a cell, comprising exposing said cell to a purified calcium channel gamma6 subunit peptide. In a preferred embodiment, the subunit peptide is an N-terminal transmembrane domain or fragment thereof. In an embodiment, the peptide is a peptide as described herein. In an embodiment, the peptide is a peptide having about at least 80% homology to peptides described herein.

In an embodiment, the invention provides a method of decreasing calcium current in a cell, comprising recombinantly expressing within said cell a calcium channel gamma6 subunit peptide, wherein the subunit peptide is an N-terminal transmembrane domain or fragment thereof.

In an embodiment, the invention provides a method of treating a disorder of calcium regulation comprising administering to a patient in need a therapeutically effective amount of a pharmaceutical composition of a peptide of the invention.

In an embodiment, the invention provides a calcium channel gamma peptide other than a gamma6 peptide, comprising a segment from a calcium channel gamma6 subunit peptide wherein the segment comprises an N-terminal transmembrane domain or fragment thereof. In a particular embodiment, the gamma peptide which is normally not capable of decreasing calcium current is conferred with an ability to decrease calcium current. For example, such conferred ability is achieved by introducing a calcium channel regulatory motif as described herein. The introducing of the motif can occur, e.g., by mutation of even a single native residue whereby the mutation generates the motif. In a particular embodiment, an ability of the gamma peptide to decrease calcium current is increased relative to its pre-modification ability level. In a particular embodiment, the calcium channel gamma peptide is gamma1. In an embodiment, the fragment comprises at least 5 continuous amino acids. In an embodiment, the segment comprises a GxxxG-like structural motif.

In an embodiment, the calcium channel gamma peptide further comprises at least a second segment from a calcium channel gamma6 subunit peptide wherein the second segment comprises an N-terminal transmembrane domain or fragment thereof.

In an embodiment, the invention provides a method of selectively regulating a high voltage activated calcium channel comprising introducing a GxxxG-like motif in a calcium channel gamma subunit peptide, wherein the motif is positioned towards an extracellular side of a transmembrane region of the calcium channel gamma subunit peptide.

In an embodiment, the invention provides a method of selectively regulating a low voltage activated calcium channel comprising introducing a GxxxG-like motif in a calcium channel gamma subunit peptide, wherein the motif is positioned towards a cytoplasmic side of a transmembrane region of the calcium channel gamma subunit peptide.

In an embodiment, the invention provides a method of selectively regulating a high voltage activated calcium channel and a low voltage activated calcium channel comprising introducing first and second GxxxG-like motifs in a calcium channel gamma subunit peptide, wherein the first motif is positioned towards an extracellular side of a transmembrane region and the second motif is positioned towards a cytoplasmic side of the transmembrane region of the calcium channel gamma subunit peptide.

Figure 9:
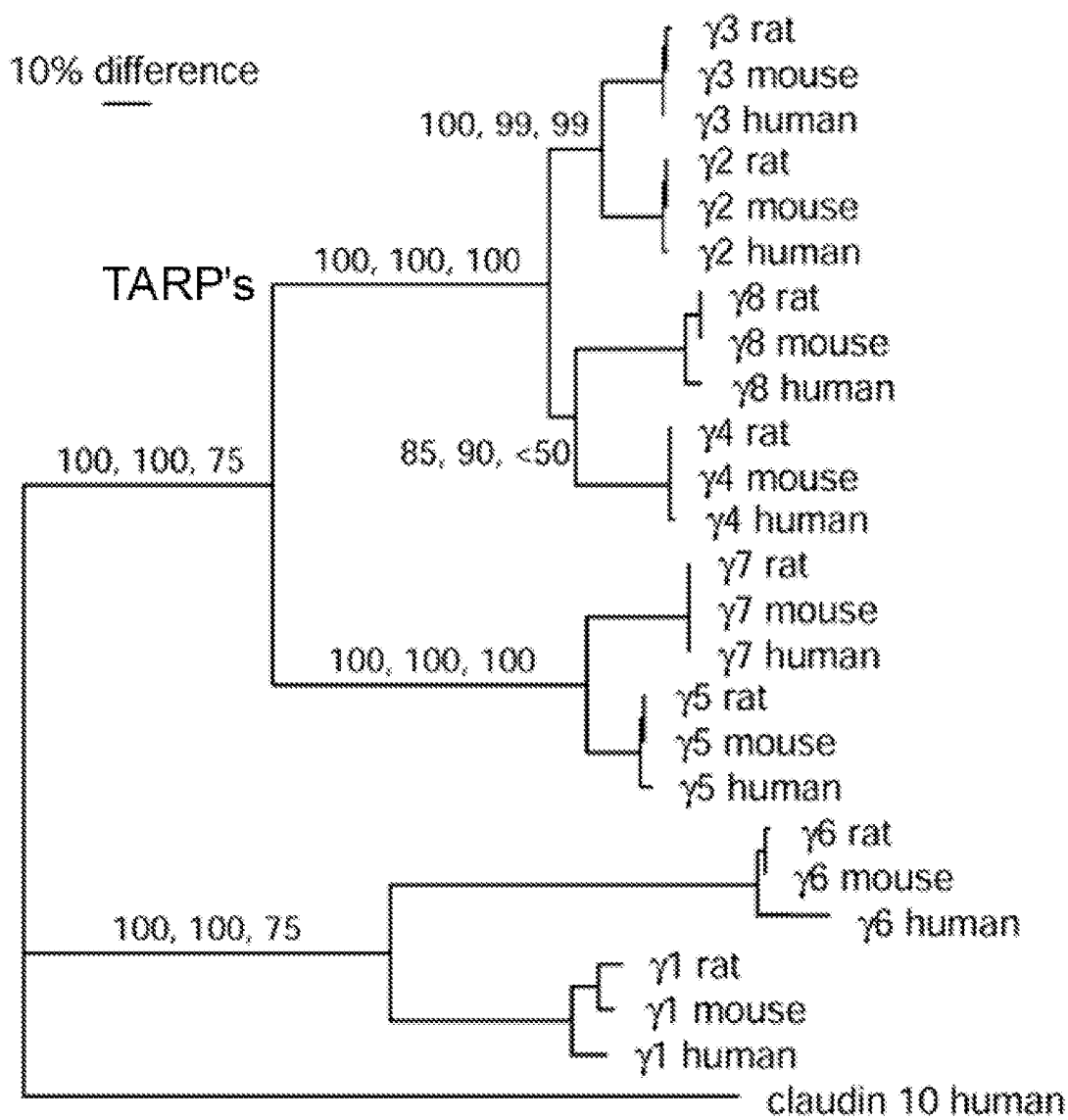

FIG. 9 illustrates the phylogeny of calcium channel γ subunits. The γ subunits can generally be divided into 3 groupings based on their phylogeny; $γ_2$, $γ_3$, $γ_4$, and $γ_8$ comprise the transmembrane AMPA receptor regulator (TARP) subgroup. Most closely related to the TARPs are $γ_5$ and $γ_7$. More distantly related to the TARPs are $γ_1$, a component of the dihydropyridine receptor complex and $γ_6$. Courtesy of Po-Ju (Chu, Robertson et al. 2001).

Figure 10:
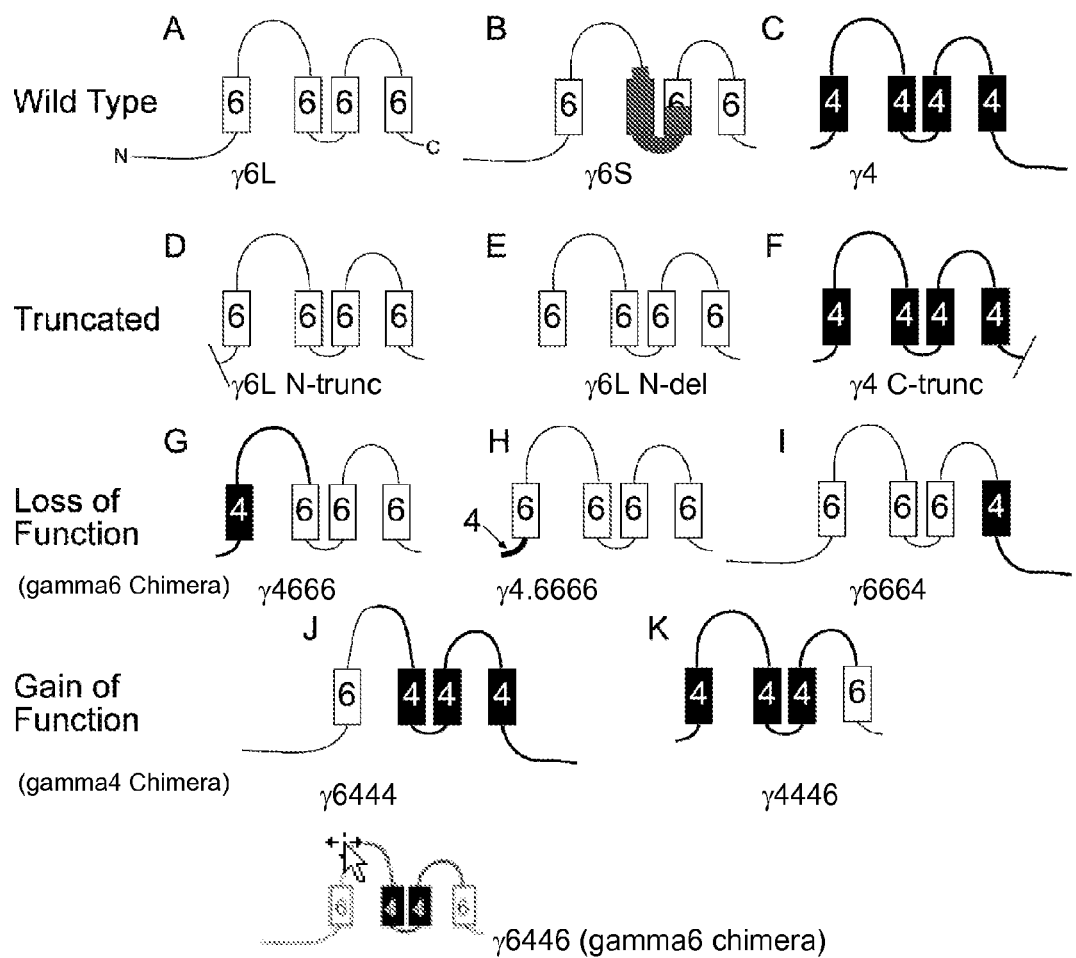

FIG. 10 is a schematic diagram of various constructs including chimeras.

FIG. 11 illustrates chimera gene sequences.

Figure 12:
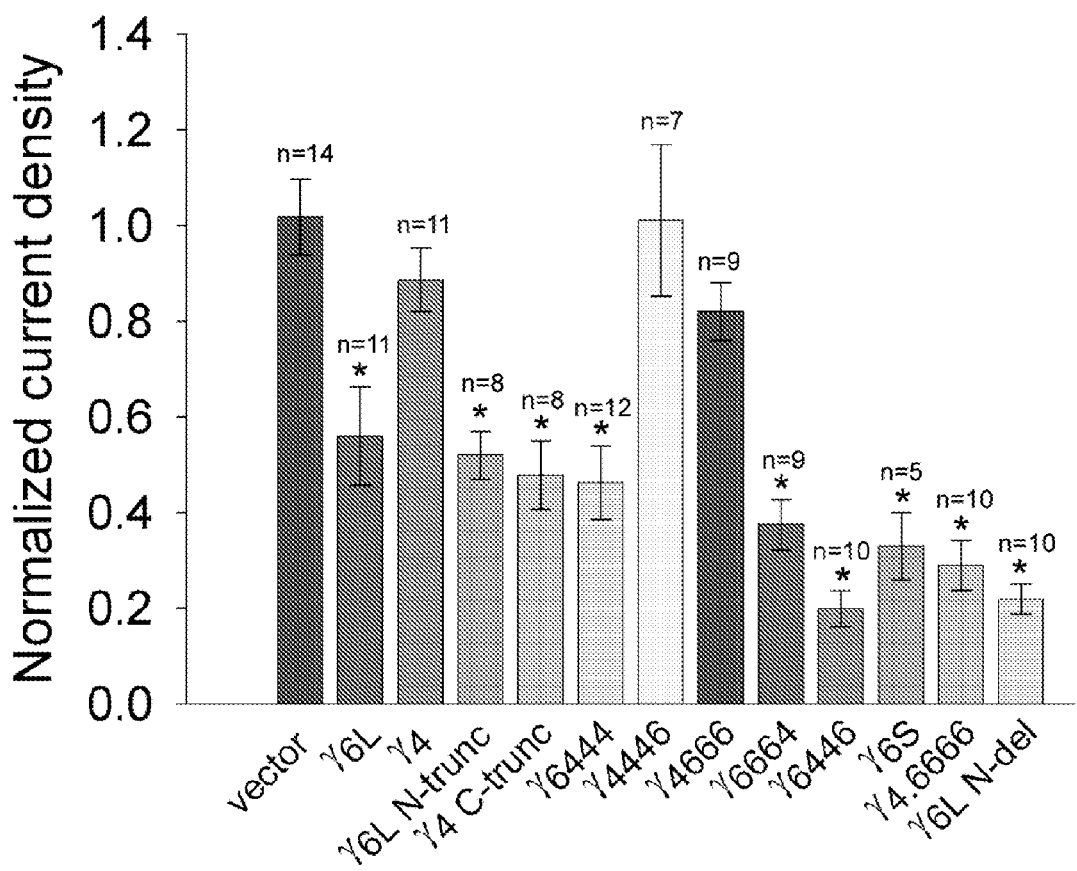

FIG. 12 illustrates results of averaged normalized current densities of low voltage-activated current from HEK/Cav3.1 transfected with chimeric constructs.

Figure 13A:
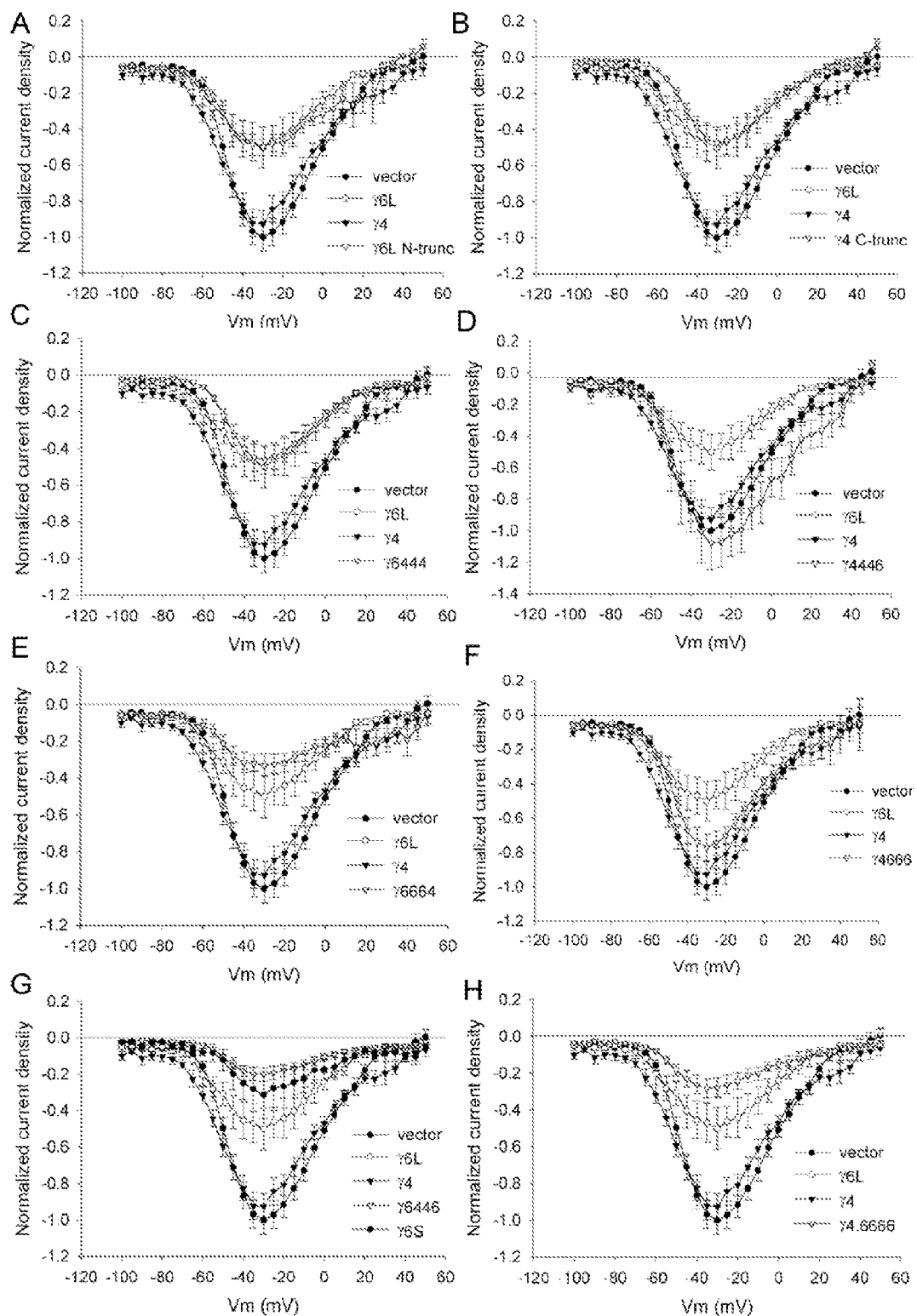
Figure 13B:
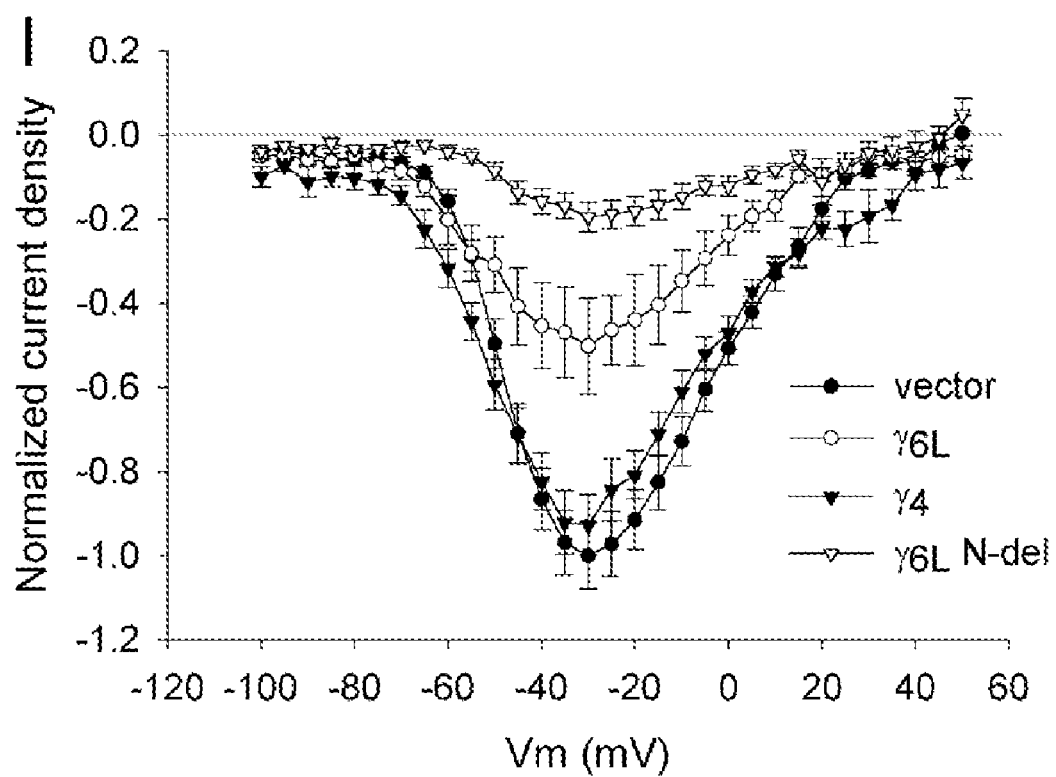

FIG. 13 (panels A-I) illustrates results of normalized current-voltage relationships of LVA current from HEK/Cav3.1 cells transfected with chimeric constructs. Each panel shows I-V curves from vector control, native $γ_{6L}$, native $γ_4$, and a specific chimera. For the $γ_{6446}$ chimera, the I-V curve for the native $γ_{6S}$ protein is also shown as it has structural and functional similarities to $γ_{6446}$.

Figure 14:
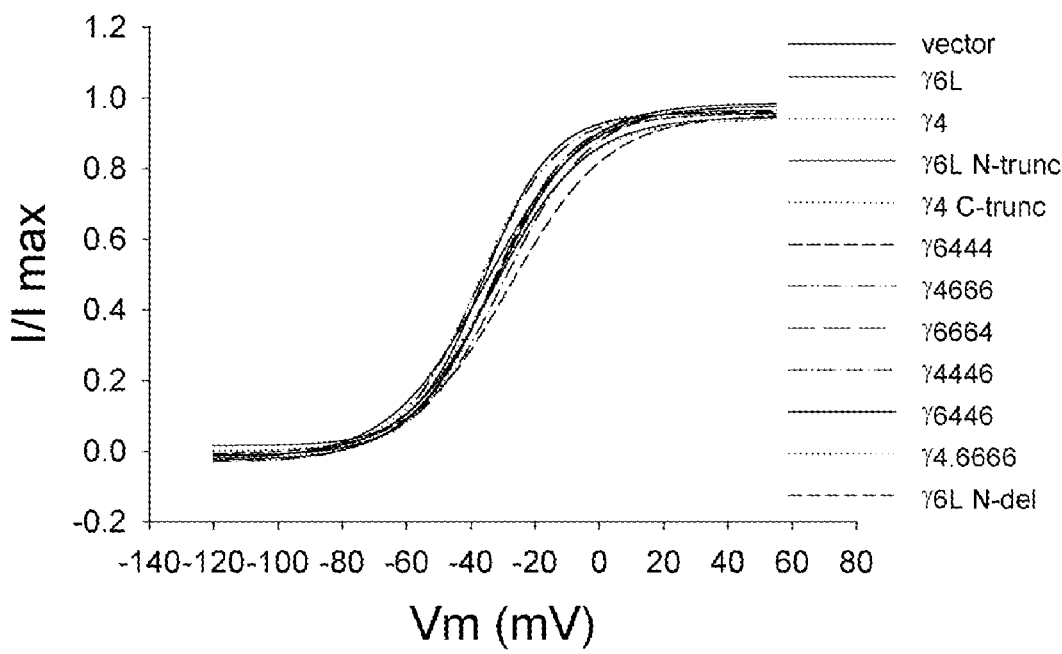

FIG. 14 illustrates results of voltage dependency of activation of low voltage-activated current from HEK/Cav3.1 cells expressing chimeric constructs. Boltzman fits to voltage dependency of non-isochronic activation curves only are shown. The V0.5 and k values of activation curves are reported in Table 1.

Figure 15:
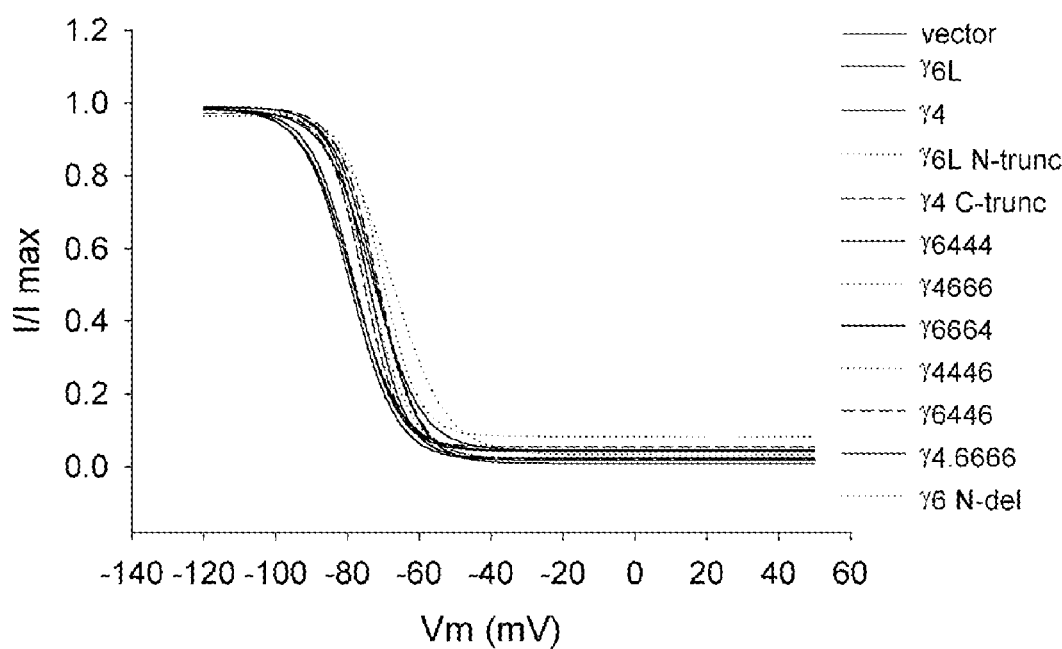

FIG. 15 illustrates voltage dependency of inactivation of low voltage-activated current from HEK/Cav3.1 cells expressing chimeric constructs. Boltzman fits to voltage dependency of inactivation curves only are shown. The V0.5 and k values of inactivation curves are reported in Table 1.

Figure 16:
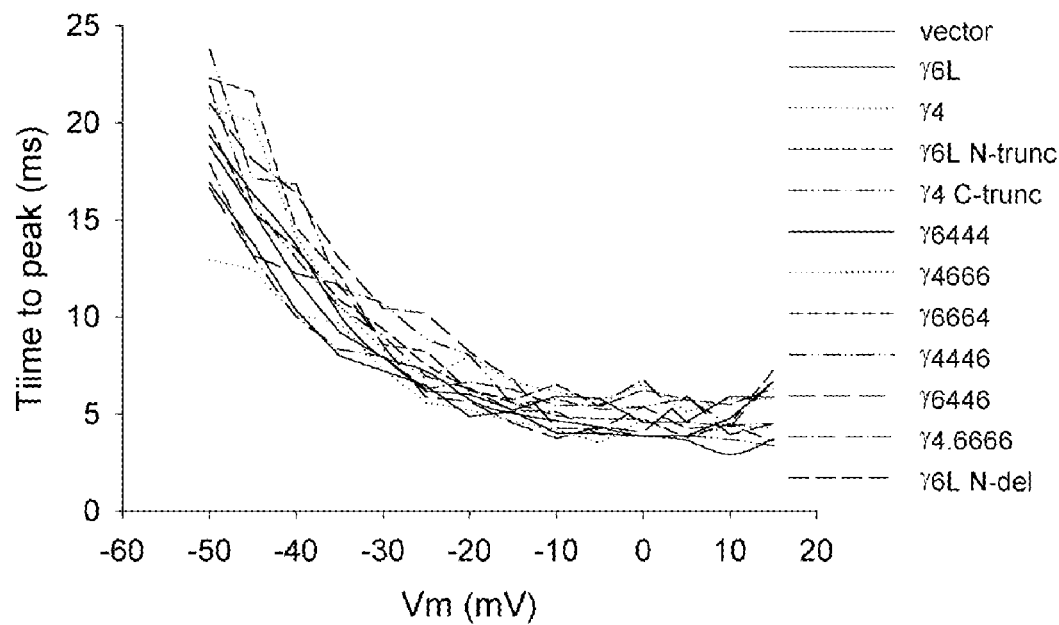

FIG. 16 illustrates voltage dependency of time to peak current of low voltage-activated current from HEK/Cav3.1 cells expressing chimeric constructs. Spline curves connecting data points only are shown. The times to peak current values at −20 mV, approximately where peak current occurred, are reported in Table 1.

Figure 17:
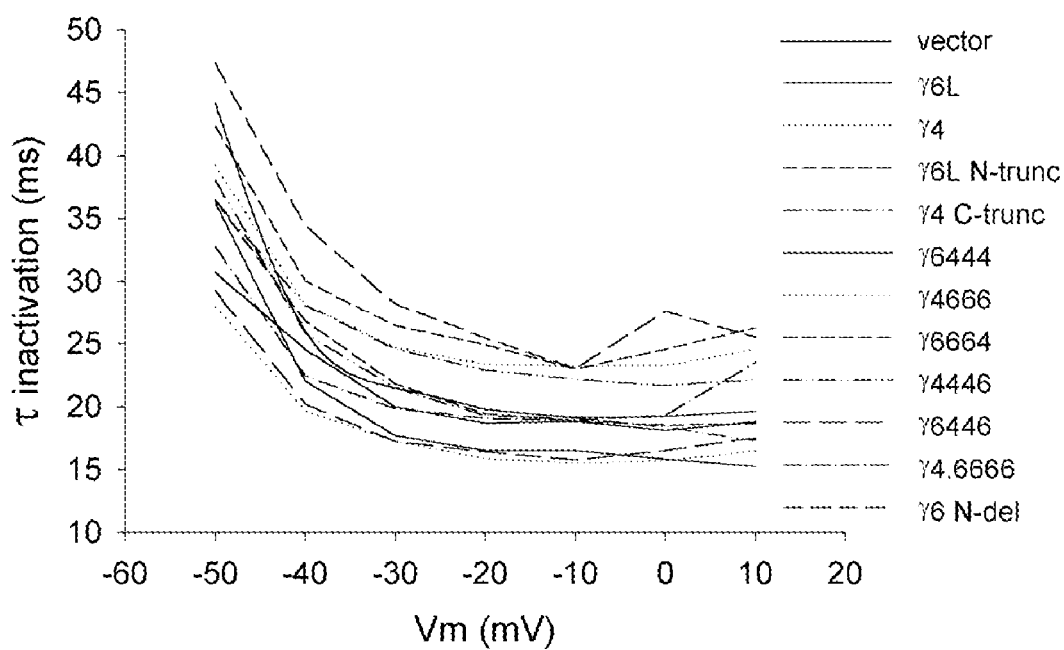

FIG. 17 illustrates results of voltage dependency of the time constant, τ (tau), of inactivation of low voltage-activated current from HEK/Cav3.1 cells expressing chimeric constructs. Spline curves connecting data points only are shown. The time constant of inactivation values at −20 mV, approximately where peak current occurred, are reported in Table 1.

Figure 18:
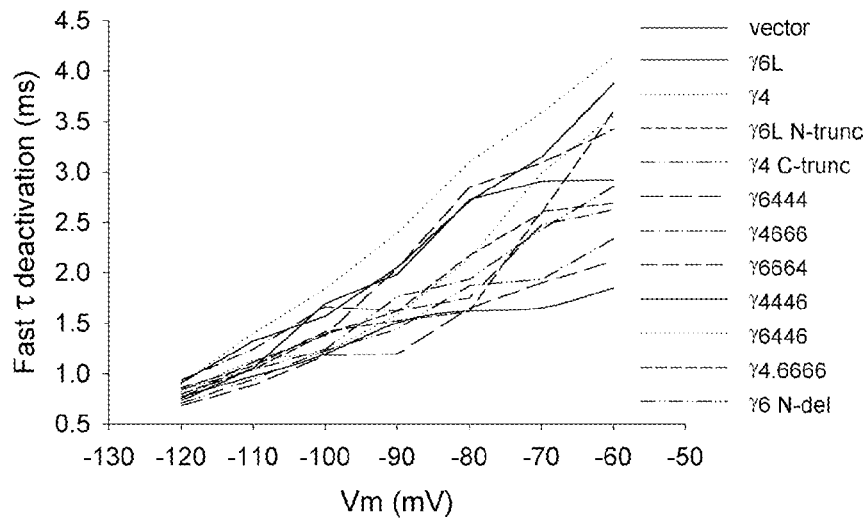

FIG. 18 illustrates results of voltage dependency of the fast component of the time constant (τ) of deactivation for low voltage-activated current from HEK/Cav3.1 cells expressing chimeric constructs. Spline curves connecting data points only are shown. The time constant of deactivation values at −100 mV are reported in Table 1.

Figure 19:
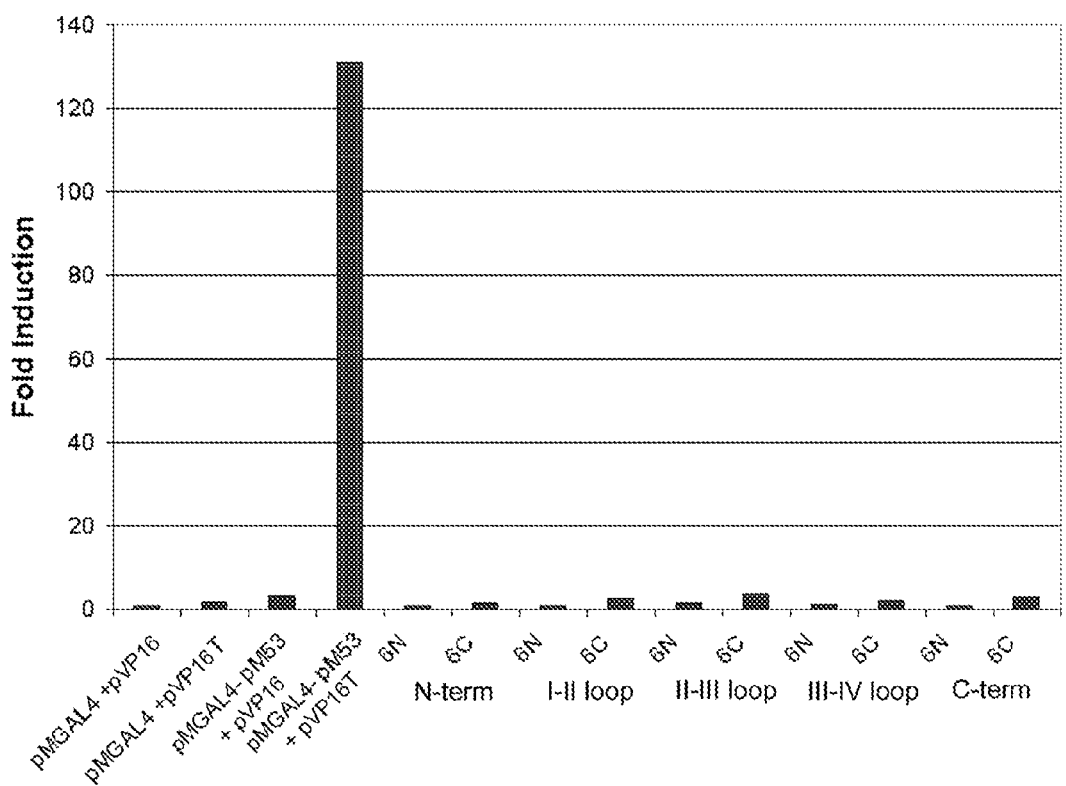

FIG. 19 illustrates results of a mammalian 2-hybrid assay for interaction of Cav3.1 and $γ_{6L}$. Fold induction in chloramphenicol-acetyl-transferase (CAT) in transfected HEK-293 parental cells (not expressing Cav3.1) is shown.

FIG. 20 illustrates an amino acid sequence alignment of transmembrane domain 1 (TM1) from γ subunits. Sequence alignment of all γ subunits is grouped by homology.

FIG. 21 illustrates a γ subunit transmembrane 1 sequence alignment by amino acid group.

Figure 22:
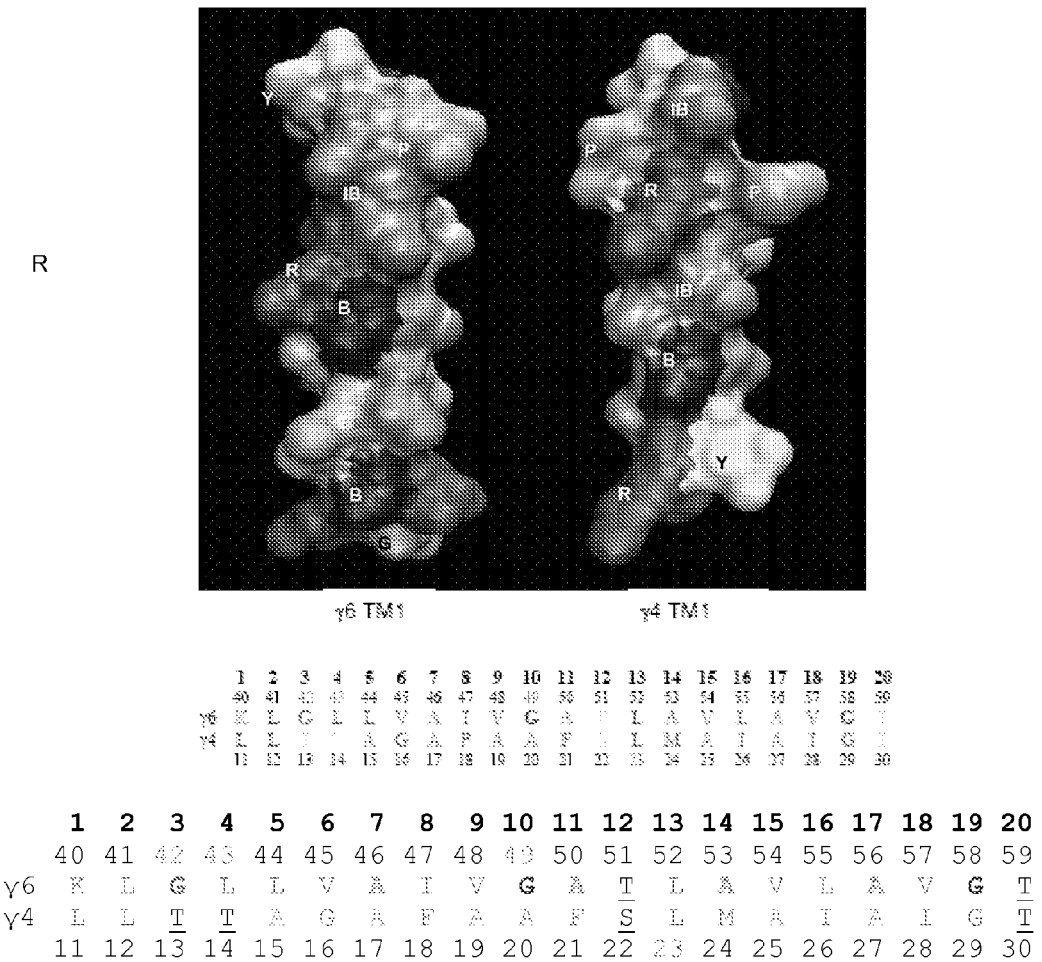

FIG. 22 illustrates a comparison of the three-dimensional structure of the first transmembrane domain of γ6 and γ4. Glycine, alanine, leucine, polar residue, charged residue and others are shown in blue, ice blue, red, yellow, green and pink, respectively. The glycine and alanine residues on γ6 subunit produce a long groove on one side of the helix (colored blue and ice blue, respectively). This figure was made using VMD. Instead of correspondingly yellow text, the sequence alignment lists one letter amino acids in black and underlined.

Figure 23:
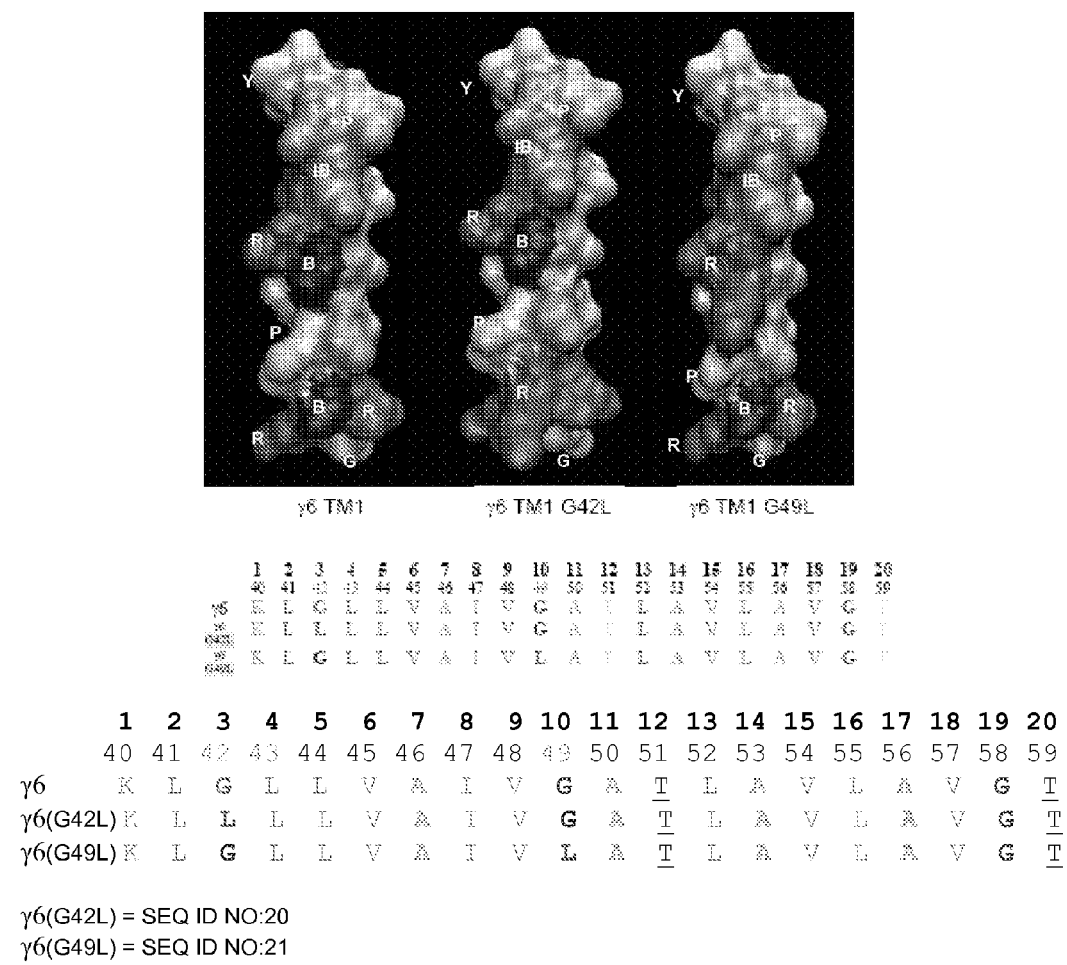

FIG. 23 illustrates a comparison of three-dimensional structures of wild type of the first transmembrane domain of γ6 subunits with mutants with mutants G42L (SEQ ID NO:20) and G49L (SEQ ID NO:21). Glycine, alanine, leucine, polar residue, charged residue and others are shown in blue, ice blue, red, yellow, green and pink, respectively. The mutant G42L can effectively remove the first GxxxA motif, and the mutant G49L can effectively remove the second GxxxA motif. This figure was made using VMD. Instead of correspondingly yellow text, the sequence alignment lists one letter amino acids in black and underlined.

Figure 24:
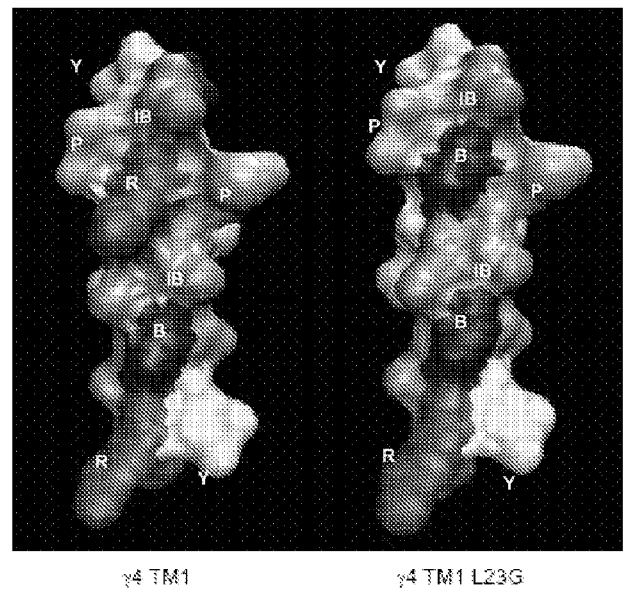

FIG. 24 illustrates a comparison of three-dimensional structures of wild type of the first transmembrane domain of γ4 subunits with mutants L23G (SEQ ID NO:22). Glycine, alanine, leucine, polar residue, and others are shown in blue, ice blue, red, yellow, and pink, respectively. The replacement of leucine with glycine produces a long groove on one face of helix (colored blue and ice blue). This figure was made using VMD. Instead of correspondingly yellow text, the sequence alignment lists one letter amino acids in black and underlined.

FIG. 25 illustrates results of electrophysiology experiments. The γ6 subunit and its first transmembrane domain decreases Cav3.1 dependent calcium currents in Cav3.1-HEK cells. A, representative whole-cell current traces for an individual Cav3.1-HEK cell stably transfected with Cav3.1 in response to voltage steps from holding potential from −100 mV to +55 mV in 5 mV interval. B, averages of normalized current voltage relationship from Cav3.1-HEK cells transiently transfected with a bicistronic vector (adCGI) expressing either GFP, GFP plus γ6, and GFP plus γ6 first transmembrane domain only. C, averages of normalized peak current density of Cav3.1-HEK cell transiently transfected with empty vector (adcGI), GFP plus γ6, GFP plus γ4, GFP plus γ6 first transmembrane domain, and GFP plus γ4 first transmembrane domain. Only γ6 and its transmembrane domain significantly decreased Cav3.1 calcium current density. The γ6 significantly decreased the current density by 42%, and its first transmembrane domain was 20%.

Figure 26:
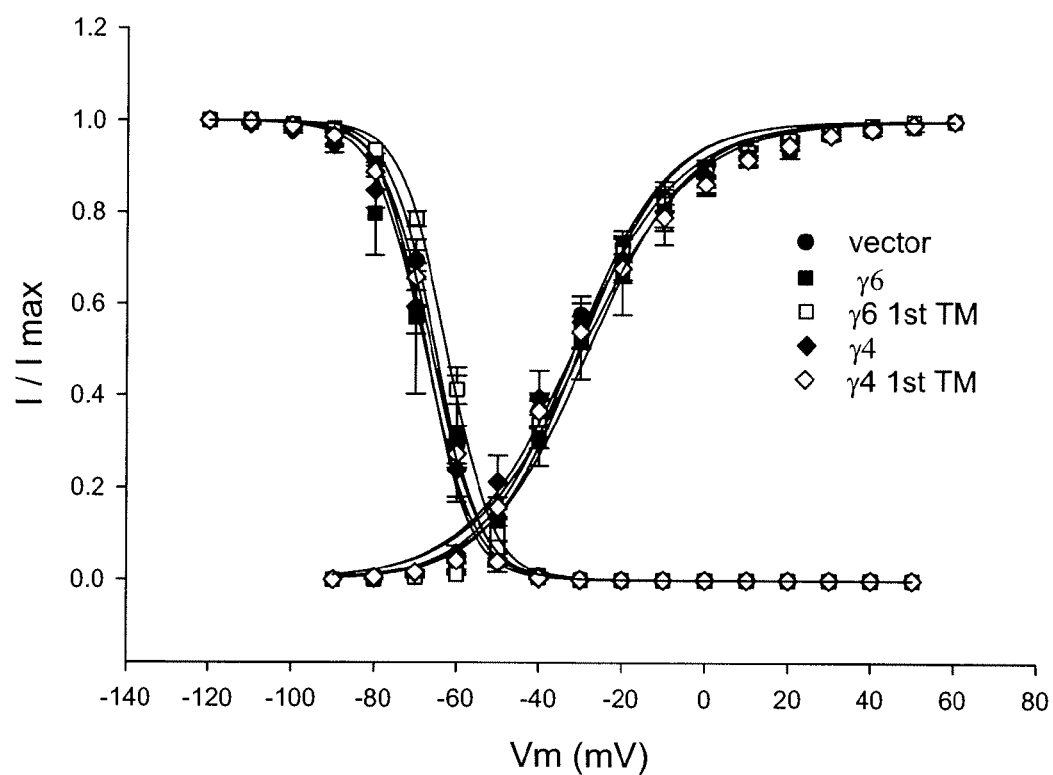

FIG. 26 illustrates results for voltage dependency of activation and inactivation of Cav3.1 coexpressed with γ subunits and chimeras. Activation and inactivation curves for currents recorded in Cav3.1-HEK cells co-expressing with one γ subunits, γ4 or γ6, or their first transmembrane domain only. No significant differences were seen for all these co-expression for either the $V_{1/2}$ or K value of both activation and inactivation when compared to control vector.

Figure 27:
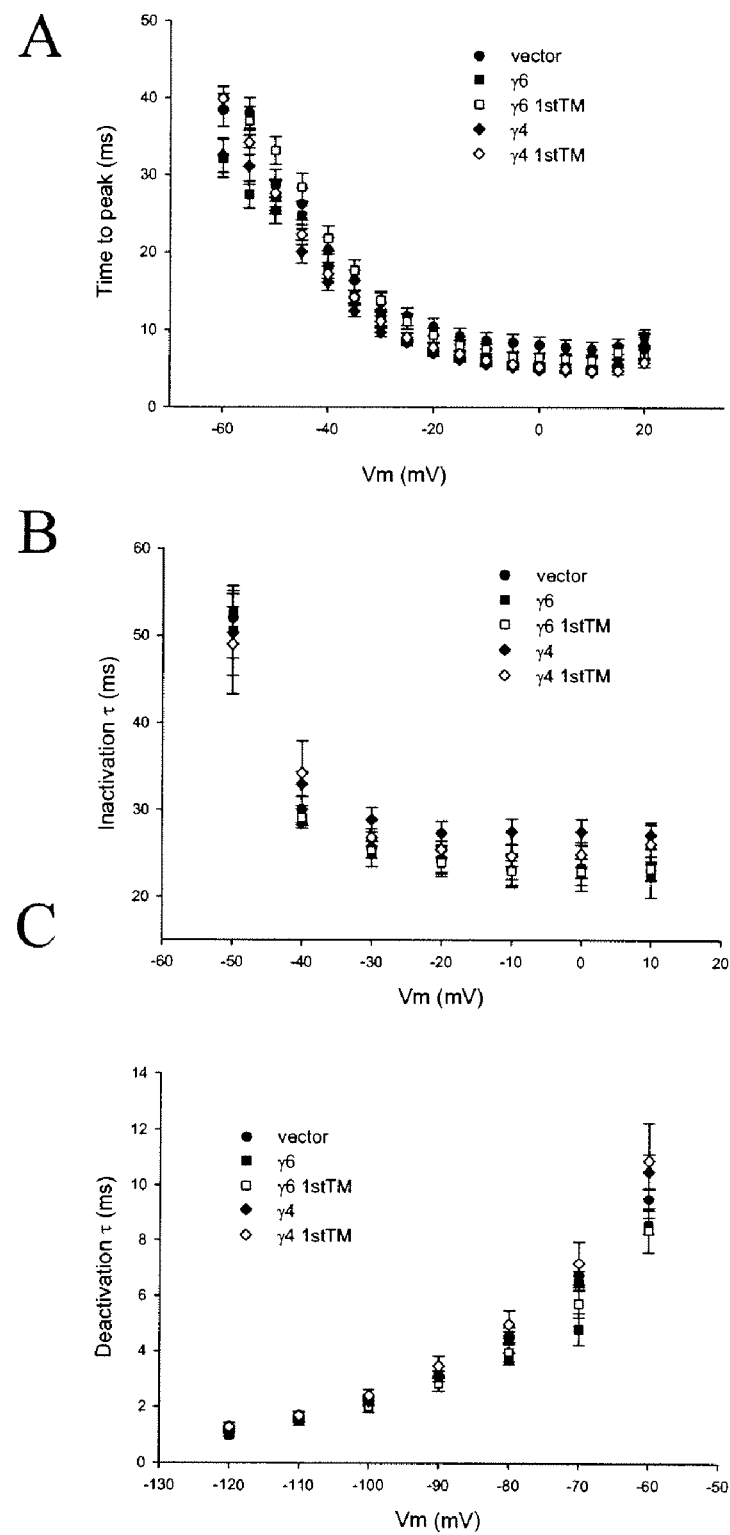

FIG. 27 illustrates results for kinetics properties of Cav3.1 co-expressed with γ4, γ6 or their first transmembrane domain. A, Time to peak, B, Time constant for inactivation, C, Time constant for deactivation. No significant differences were found among these γ subunits and chimeras.

Figure 28:
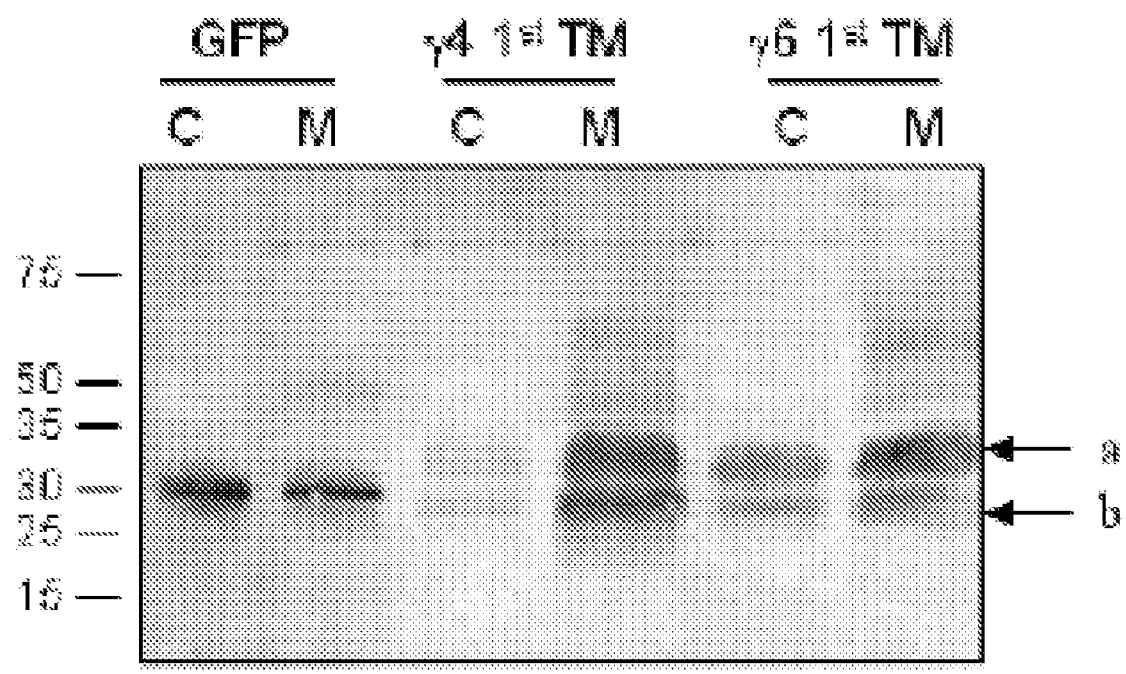

FIG. 28 illustrates a Western blot experiment. The results indicated that these GFP tagged first transmembrane domains were located in cell membrane. GFP fusion proteins contain GFP and the first transmembrane domain from γ6 and γ4. The band "a" is GFP fusion protein, and band "b" is GFP protein (courtesy of Janice Jones).

Figure 29:
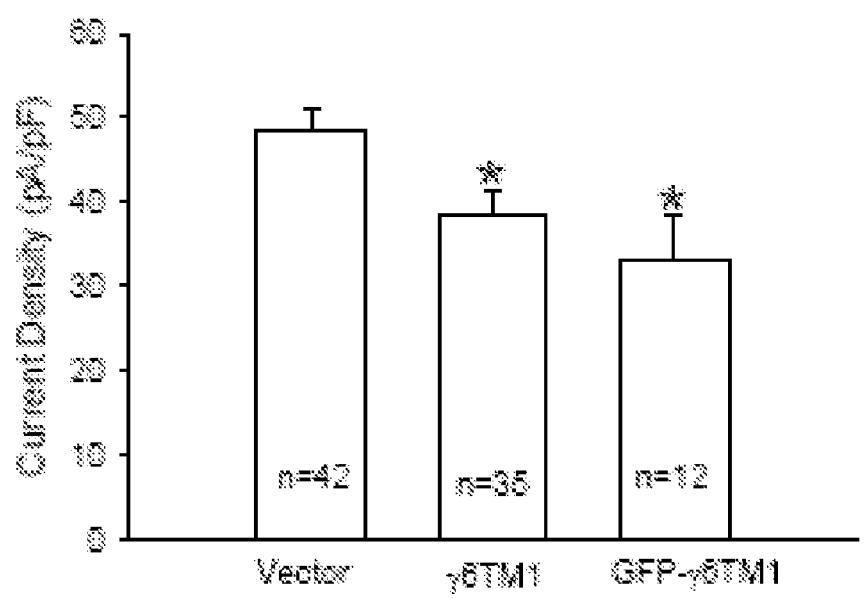

FIG. 29 illustrates averages of current density of Cav3.1-HEK cell transiently transfected with either empty vector (adcGI), γ6 TM1 and fusion GFP-γ6 TM1. The γ6 TM1 and fusion GFP-γ6 TM1 decreased Cav3.1 calcium current density.

Figure 30:
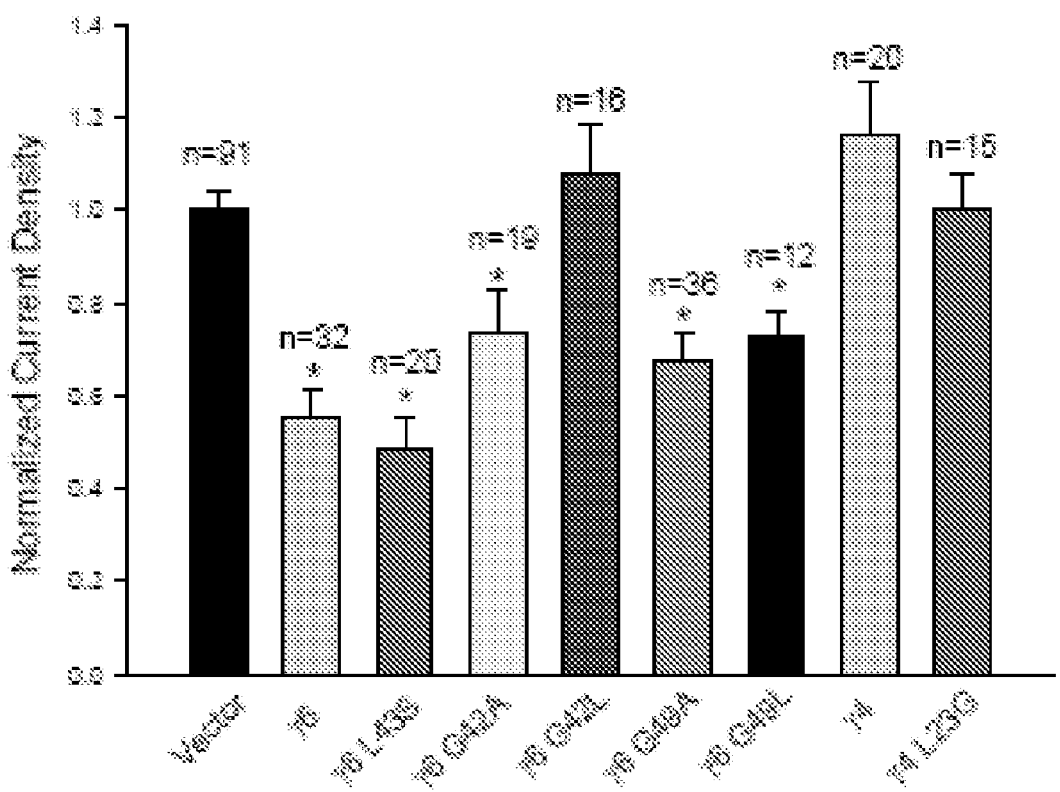

FIG. 30 illustrates averages of normalized peak current density of Cav3.1-HEK cell transiently transfected with either empty vector (adcgi), GFP plus γ6, GFP plus γ4, GFP plus γ6 and γ4 mutants. Only the G42L mutant of γ6 removes its inhibitory function.

Figure 31:
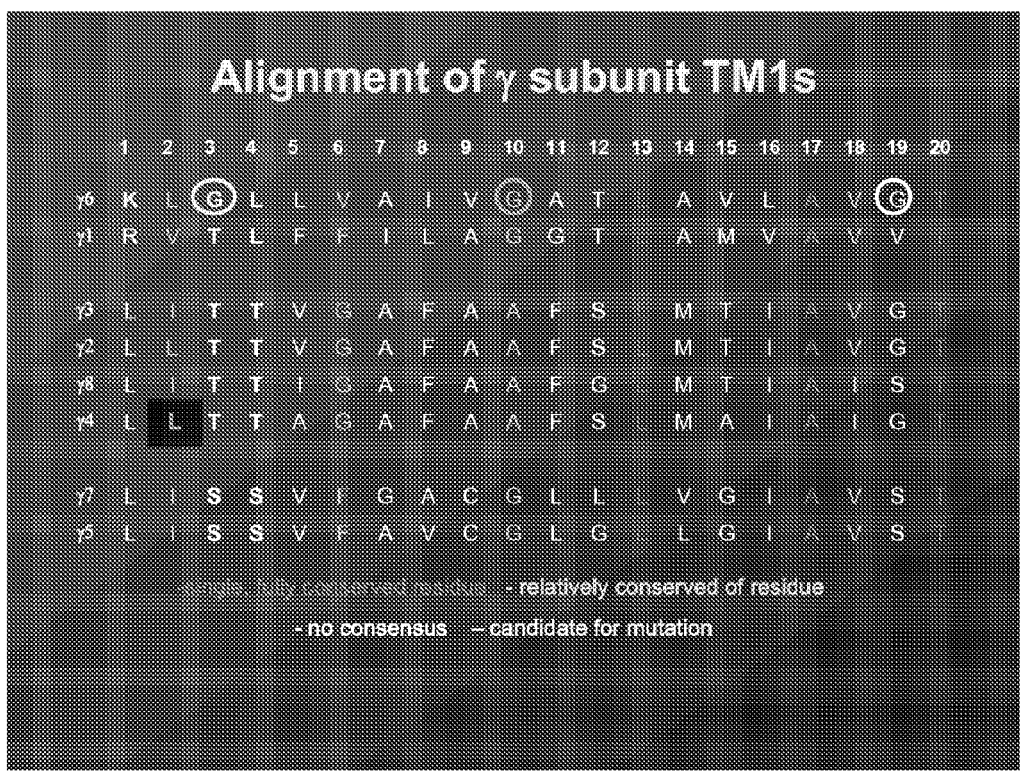

FIG. 31 illustrates an alignment of amino acid sequences of gamma subunit TM1 domains.

Figure 32:
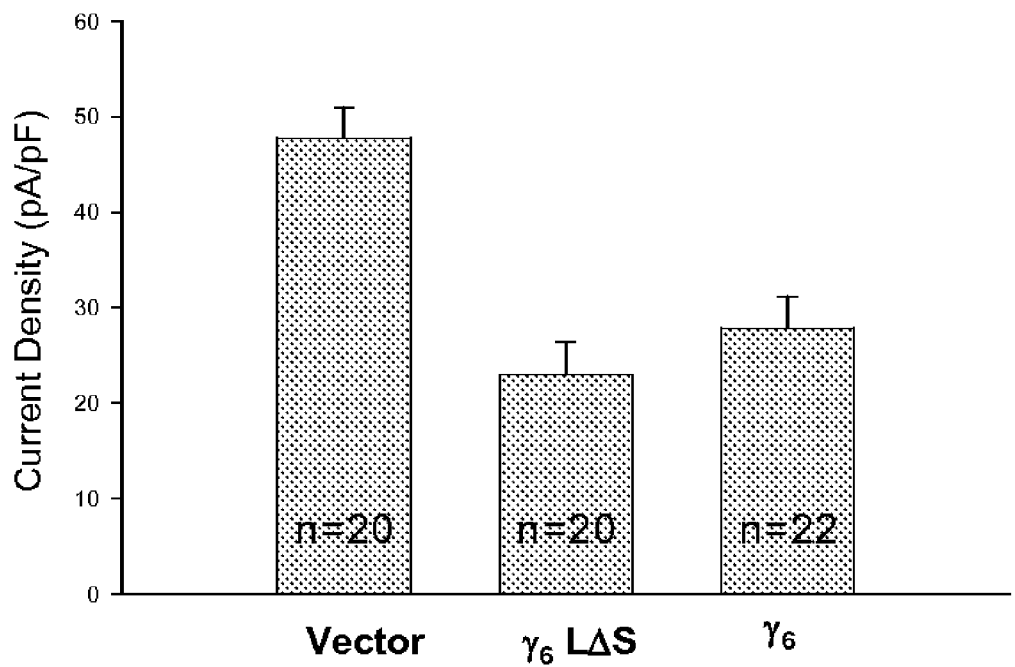

FIG. 32 illustrates results of functional analysis of a gamma6 mutant, leucine-delta-serine.

Figure 33:
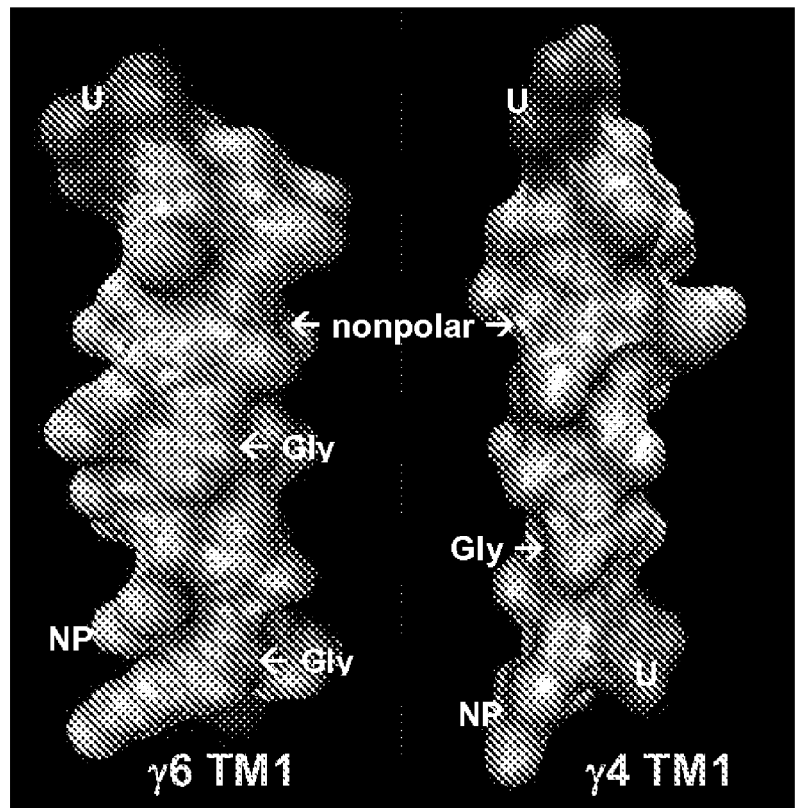

FIG. 33 illustrates structural features of gamma6 and gamma4 TM1 domains.

Figure 34:
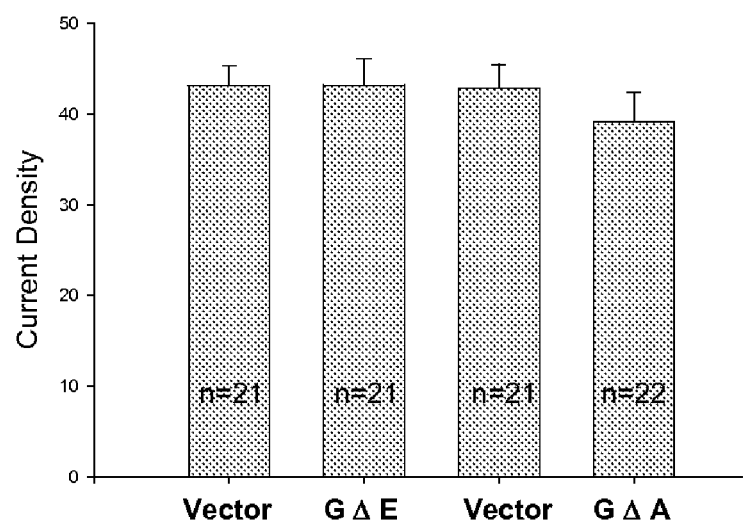

FIG. 34 illustrates results of functional analysis of gamma6 TM1 mutants, glycine-delta-glutamate and glycine-delta-alanine.

Figure 35:
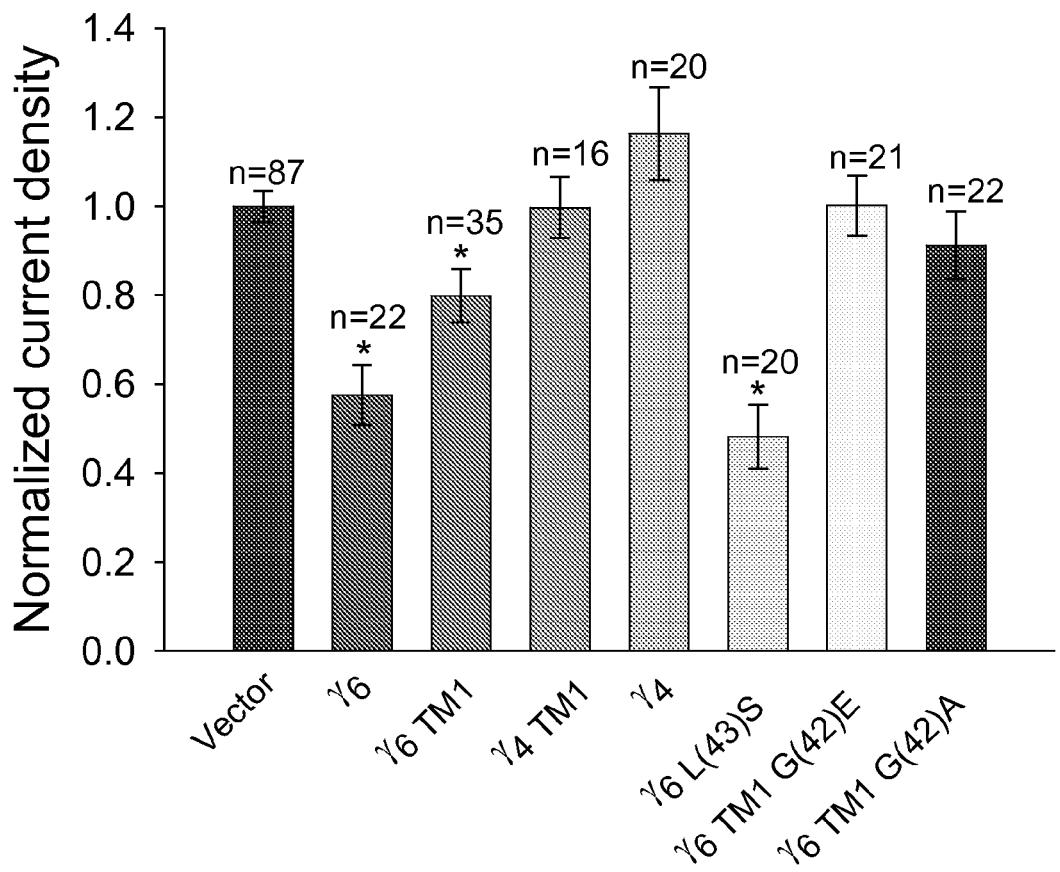

FIG. 35 illustrates results of testing calcium current density for various gamma subunits and variants.

Figure 36:
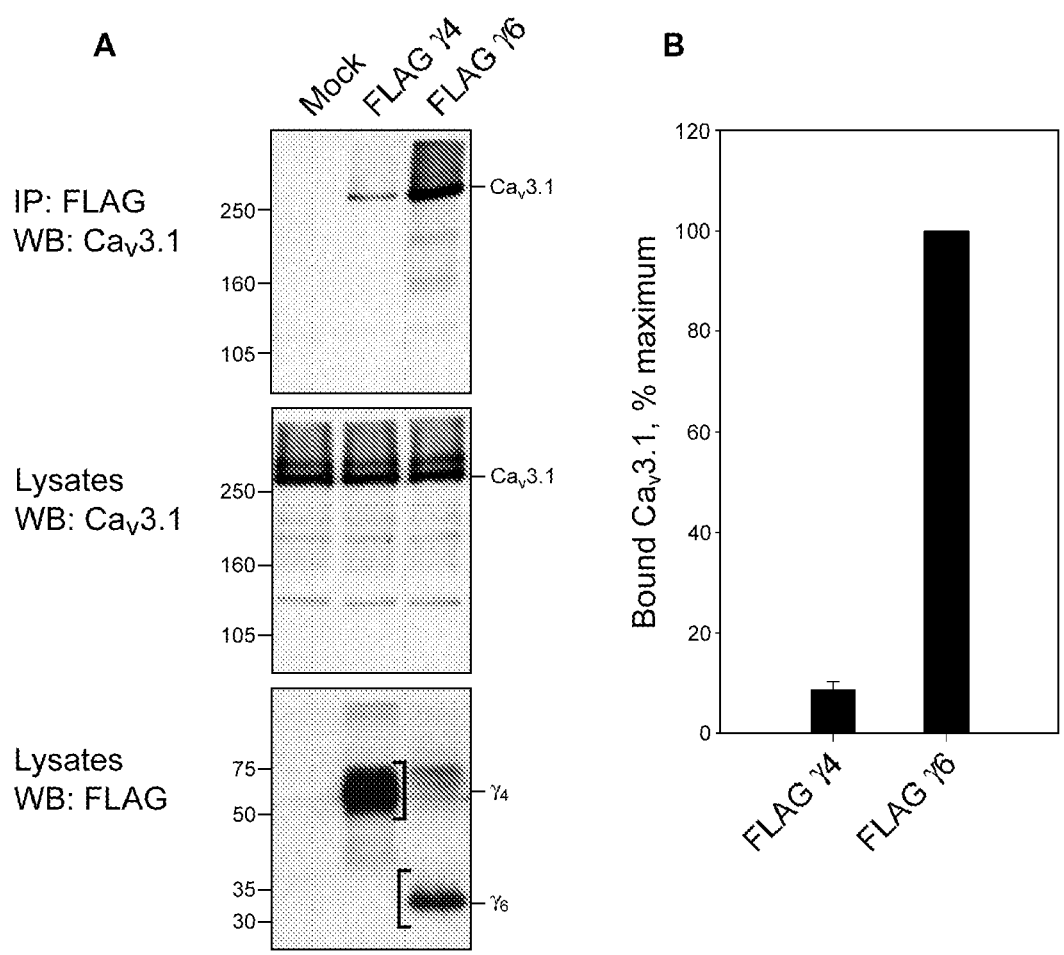

FIG. 36 illustrates results of co-immunoprecipitation experiments with $Ca_v3.1$ and gamma6 or gamma4.

Figure 37:
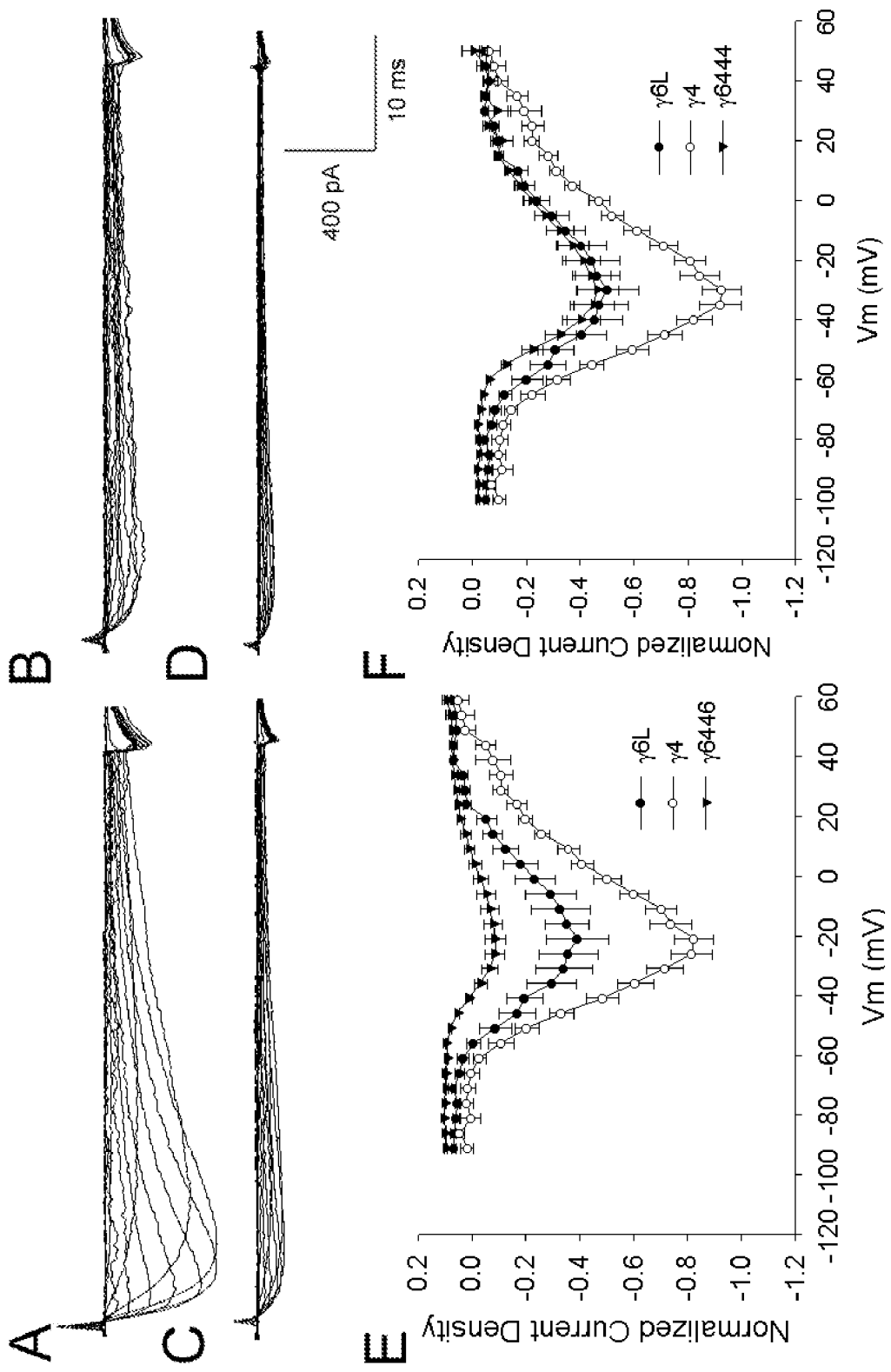

FIG. 37 illustrates representational Cav3.1 current traces and I/V curves demonstrating the effects of transiently transfecting Cav3.1/HEK cells with plasmids expressing: (A) $\gamma_4$ (B) $\gamma_{6L}$ (C) $\gamma_{6446}$ and (D) $\gamma_{6444}$. (E) and (F) show normalized current voltage curves.

Figure 38:
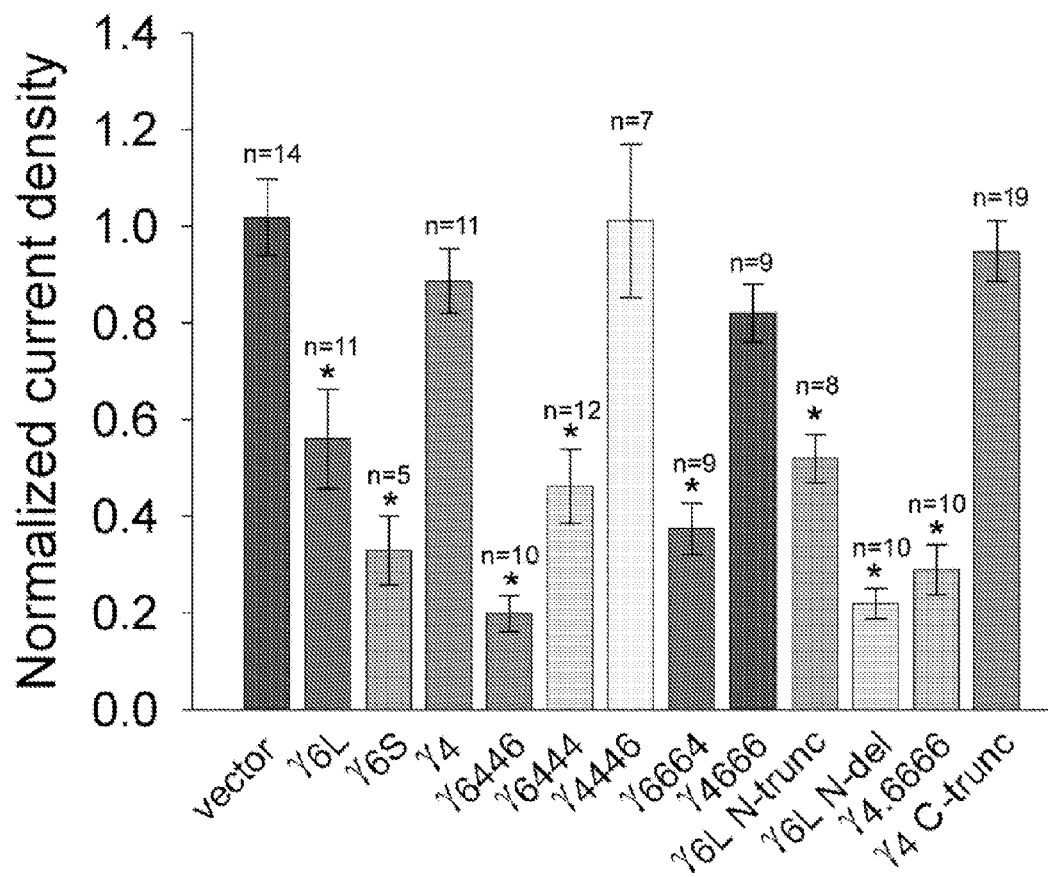

FIG. 38 illustrates the ability of gamma subunit constructs to mediate changes in calcium current (average effects on Cav3.1 calcium current density of the wild type γ subunits ($\gamma_{6L}$, $\gamma_{6S}$, $\gamma_4$) compared to various chimeras and truncated peptides).

Figure 39:
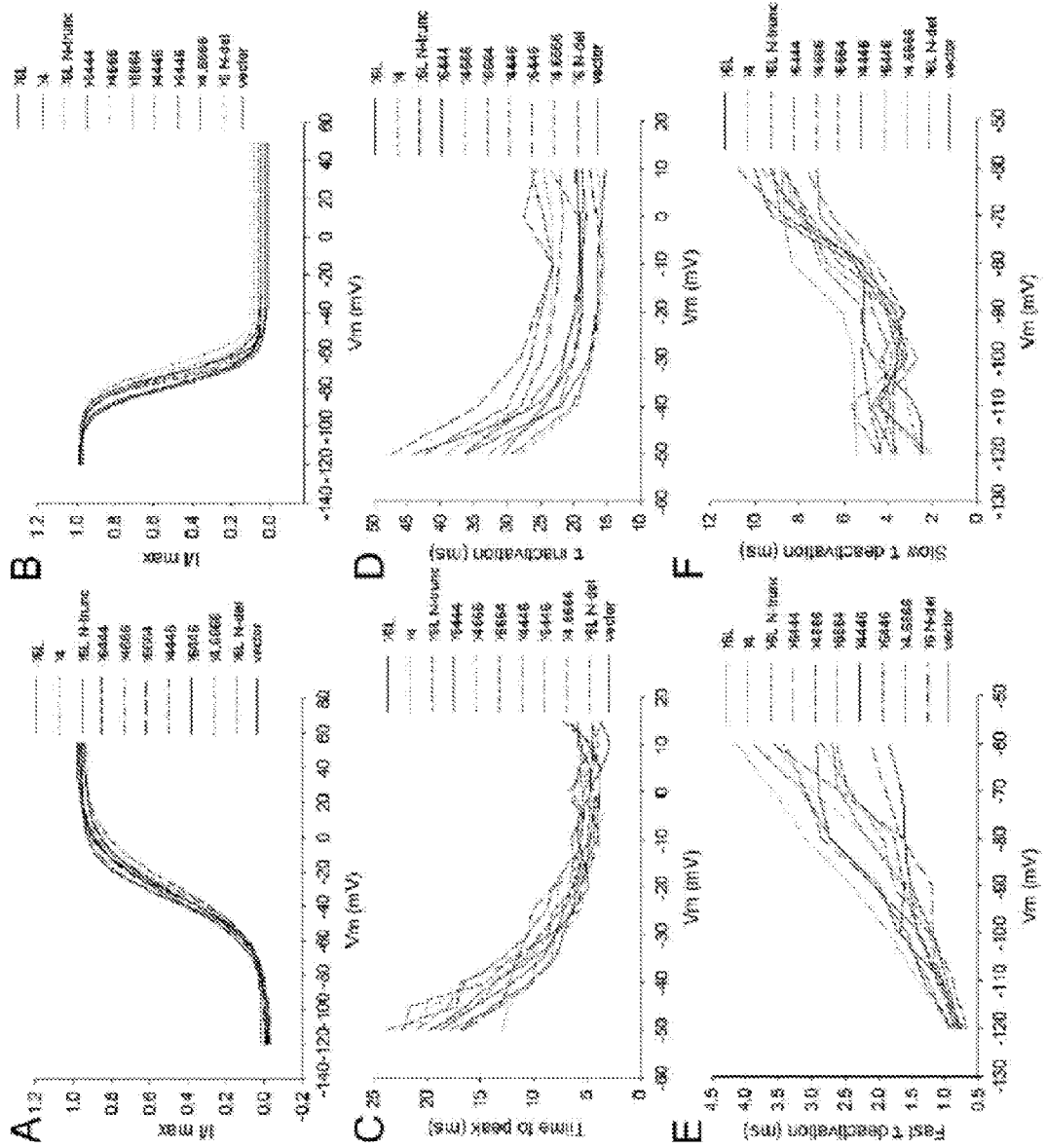

FIG. 39 illustrates the effects of wild-type and chimeric gamma subunits on voltage dependency and kinetics of Cav3.1 current. (A) Voltage dependency of activation; (B) Voltage dependency of inactivation; (C) Time to peak current; (D) τ of inactivation; (E) τ fast of deactivation; (F) τ slow of deactivation.

Figure 40:
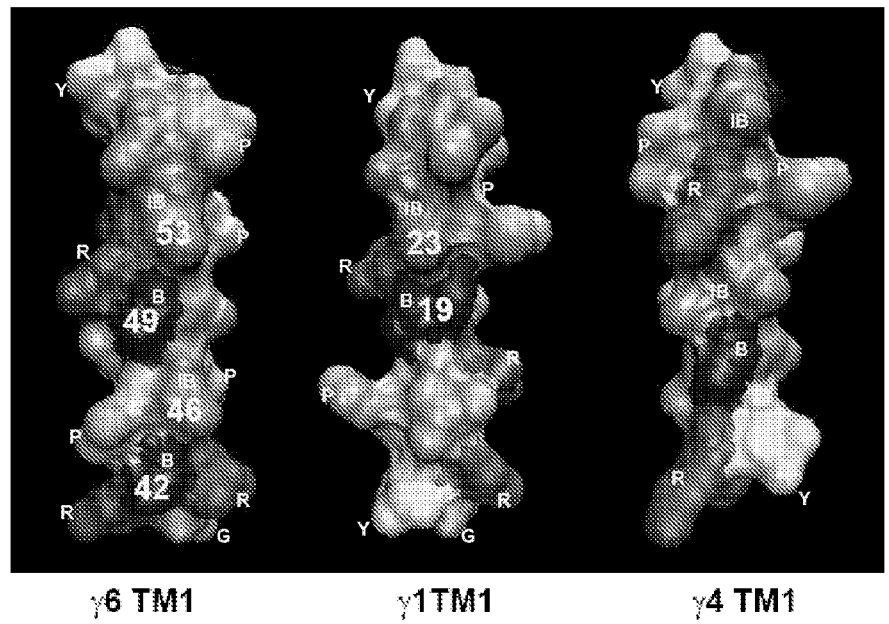

FIG. 40 illustrates (top) sequence alignments of TM1 of $\gamma_6$, $\gamma_4$ and $\gamma_1$. and (bottom) space filling models of the corresponding sequences.

FIG. 41 illustrates effects of certain mutations in gamma peptides on the ability to mediate changes in calcium current: (A) Normalized, averaged data showing the effects of various point mutations on the ability of $\gamma_6$ to decrease Cav3.1 current. (B) Introduction of a GXXXA motif into TM1 of $\gamma_1$ confers the ability to decrease Cav3.1 calcium current.

DETAILED DESCRIPTION OF THE INVENTION

When used herein, the term peptide refers to a protein fragment generally. A peptide can be made of natural amino acids or non-natural variations thereof as understood in the art. A peptide can be made by a variety of methods as understood in the art, for example using synthetic or recombinant techniques.

When used herein, the term isolated or purified can encompass meanings such as at least partially isolated and at least partially purified.

The invention may be further understood by the following non-limiting examples.

EXAMPLE 1

Calcium Channel γ6 Subunits are Unique Modulators of Low Voltage-Activated (Cav3.1) Calcium Current Using chimeric $\gamma_6$ constructs in which portions of the parent molecule are replaced by equivalent regions from other γ subunits we have demonstrated that only the first transmembrane domain (TM1) is required for the inhibition of current. Expression of just TM1 of the $\gamma_6$ protein (approximately 20 amino acids) in cells is sufficient to reduce calcium current. By selectively mutating single amino acids in TM1 we have identified a critical GxxxA motif that is required for ion current inhibition by the $\gamma_6$ protein.

Brief Description of Figures for Example 1

Figure 1:
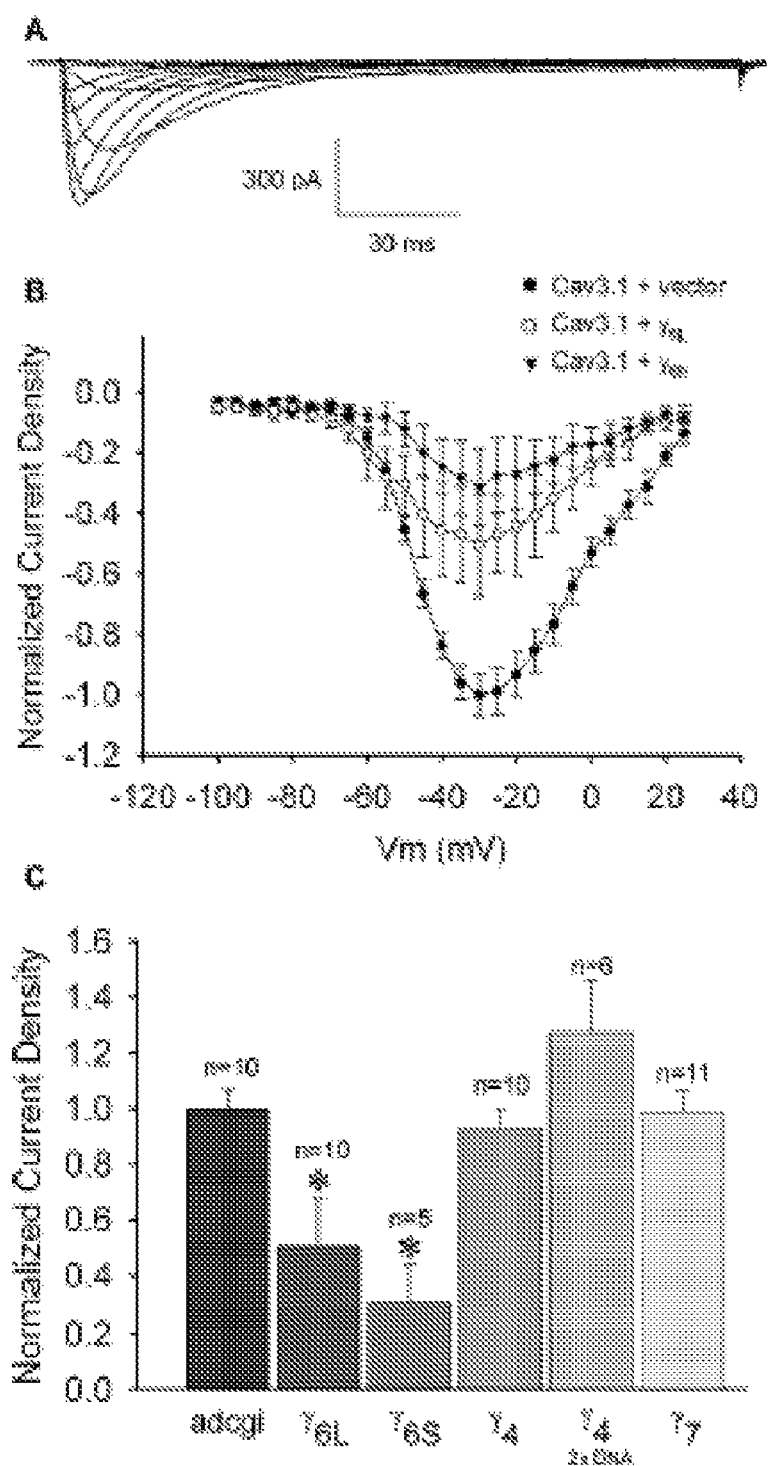
FIG. 1. Only the γ6 subunit decreases Cav3.1 dependent LVA currents in HEK-293 cells. A: Representative whole-cell current traces from an individual HEK-293 cell stably transfected with Cav3.1. Traces were elicited by stepping membrane voltage from a holding potential of −100 to +10 mV, in 10 mV increments, for 250 ms. B: Average normalized current-voltage relationships from HEK-293/Cav3.1 transiently transfected with a bicistronic vector (adCGI) expressing either GFP, GFP plus γ6L, or GFP plus γ6S. C: Average normalized peak current density of HEK-293/Cav3.1 transiently transfected with either GFP, GFP plus γ6L, GFP plus γ6S, GFP plus γ4, GFP plus γ4 using a twofold increase in DNA concentration or GFP plus γ7. Only the γ6 isoforms significantly decrease LVA current density in these cells.

FIG. 1. Only the γ6 subunit decreases Cav3.1 dependent LVA currents in HEK-293 cells. A: Representative whole-cell current traces from an individual HEK-293 cell stably transfected with Cav3.1. Traces were elicited by stepping membrane voltage from a holding potential of −100 to +10 mV, in 10 mV increments, for 250 ms. B: Average normalized current-voltage relationships from HEK-293/Cav3.1 transiently transfected with a bicistronic vector (adCGI) expressing either GFP, GFP plus γ6L, or GFP plus γ6S. C: Average normalized peak current density of HEK-293/Cav3.1 transiently transfected with either GFP, GFP plus γ6L, GFP plus γ6S, GFP plus γ4, GFP plus γ4 using a twofold increase in DNA concentration or GFP plus γ7. Only the γ6 isoforms significantly decrease LVA current density in these cells.

Table 2. Effects of γ subunits on the biophysical properties of Cav3.1 dependent currents in HEK-293 cells. There are no significant differences in the voltage at peak current, voltage dependency, or kinetic parameters between cells transiently transfected with vector as compared to cells transfected with any of the γ subunits studied.

Figure 2:
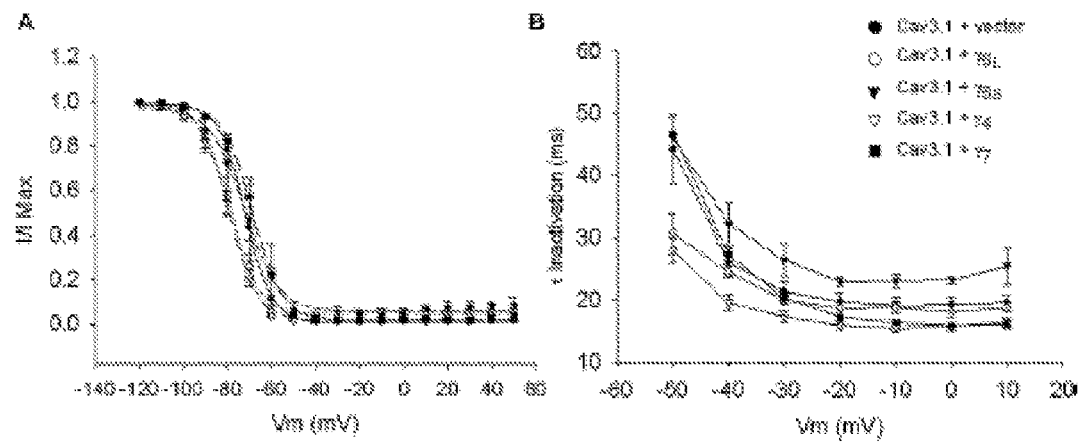
FIG. 2. Effects of γ subunits on inactivation properties of Cav3.1 expressed in HEK-293 cells. A and B: Average inactivation curves and average voltage dependence of the time constant of inactivation, respectively, from HEK-293/Cav3.1 and transiently transfected with GFP only, GFP plus γ6L, GFP plus γ6S, GFP plus γ4, and GFP plus γ7. None of the γ subunits significantly affected the inactivation properties of Cav3.1 dependent LVA current in HEK-293 cells.

FIG. 2. Effects of γ subunits on inactivation properties of Cav3.1 expressed in HEK-293 cells. A and B: Average inactivation curves and average voltage dependence of the time constant of inactivation, respectively, from HEK-293/Cav3.1 and transiently transfected with GFP only, GFP plus γ6L, GFP plus γ6S, GFP plus γ4, and GFP plus γ7. None of the γ subunits significantly affected the inactivation properties of Cav3.1 dependent LVA current in HEK-293 cells.

Figure 3:
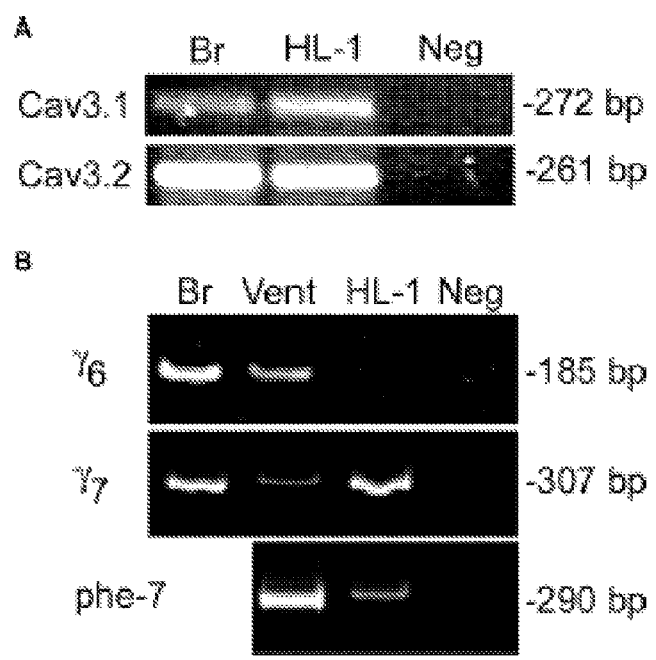
FIG. 3. Detection of α1 and γ subunits mRNAs in HL-1 cells by RT-PCR. A: Cav3.1 (α1G) and Cav3.2 (α1H) are both expressed in HL-1 cells. B: HL-1 cells express only the γ7 subunit and not the γ6 subunit. Additionally, no expression of γ4 was detected in HL-1 cells (data not shown). Whole rat brain, which is known to express Cav3.1 and Cav3.2 as well as γ6 and γ7, was used as a positive control, and a ribosomal RNA gene, PHE-7, was used as a housekeeping gene. No RT was used as a negative control.

FIG. 3. Detection of α1 and γ subunits mRNAs in HL-1 cells by RT-PCR. A: Cav3.1 (α1G) and Cav3.2 (α1H) are both expressed in HL-1 cells. B: HL-1 cells express only the γ7 subunit and not the γ6 subunit. Additionally, no expression of γ4 was detected in HL-1 cells (data not shown). Whole rat brain, which is known to express Cav3.1 and Cav3.2 as well as γ6 and γ7, was used as a positive control, and a ribosomal RNA gene, PHE-7, was used as a housekeeping gene. No RT was used as a negative control.

Figure 4:
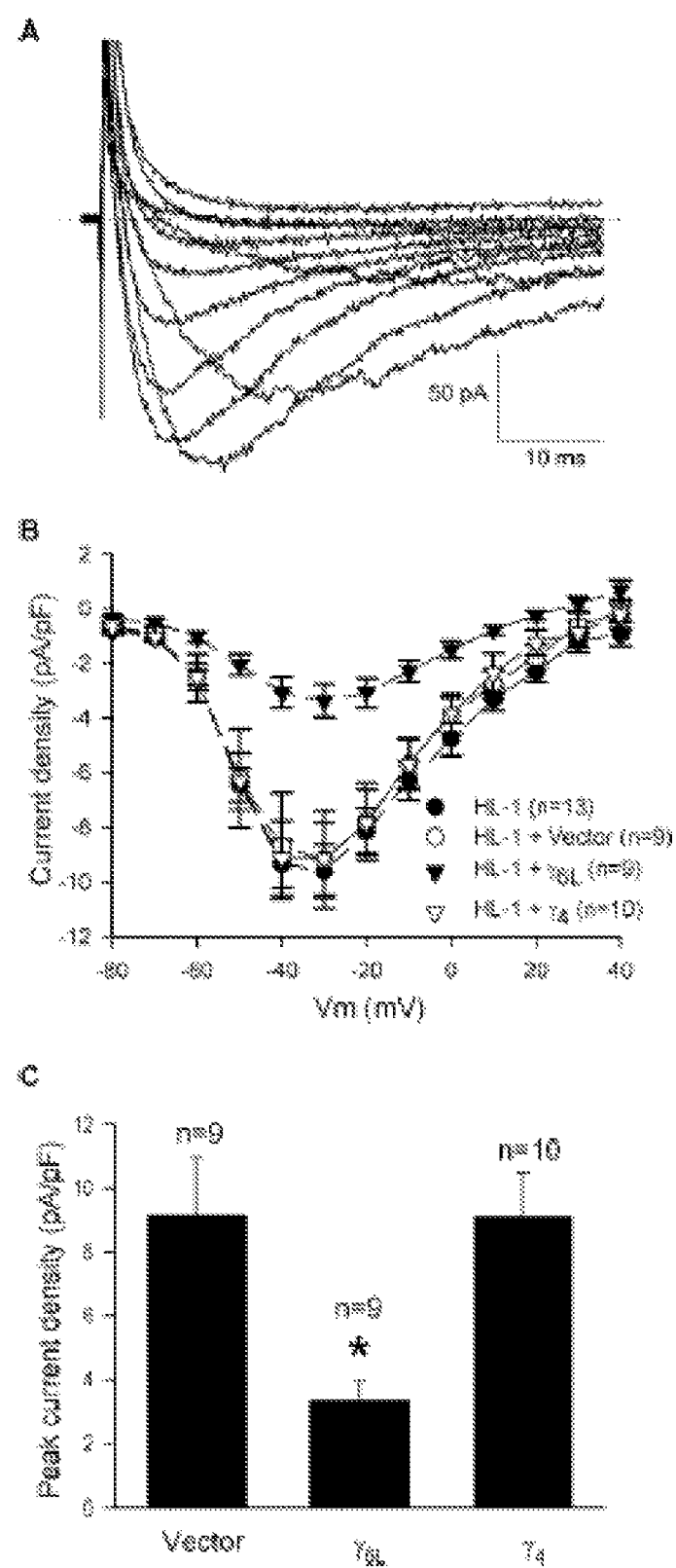
FIG. 4. γ6L decreases endogenous LVA calcium current density in HL-1 cells. A: Sample whole-cell current traces from an untransfected HL-1 cell. Traces were elicited by stepping membrane potential from a holding potential of −90 to +10 mV in 10 mV increments. B and C: Average current-voltage relationships and peak current density, respectively, from untransfected HL-1 cells, from cells transfected with GFP only, and from cells transfected with GFP plus γ6L. γ6L significantly reduced endogenous LVA current as compared to vector control, without altering the voltage at which current peaks.

FIG. 4. γ6L decreases endogenous LVA calcium current density in HL-1 cells. A: Sample whole-cell current traces from an untransfected HL-1 cell. Traces were elicited by stepping membrane potential from a holding potential of −90 to +10 mV in 10 mV increments. B and C: Average current-voltage relationships and peak current density, respectively, from untransfected HL-1 cells, from cells transfected with GFP only, and from cells transfected with GFP plus γ6L. γ6L significantly reduced endogenous LVA current as compared to vector control, without altering the voltage at which current peaks.

Figure 5:
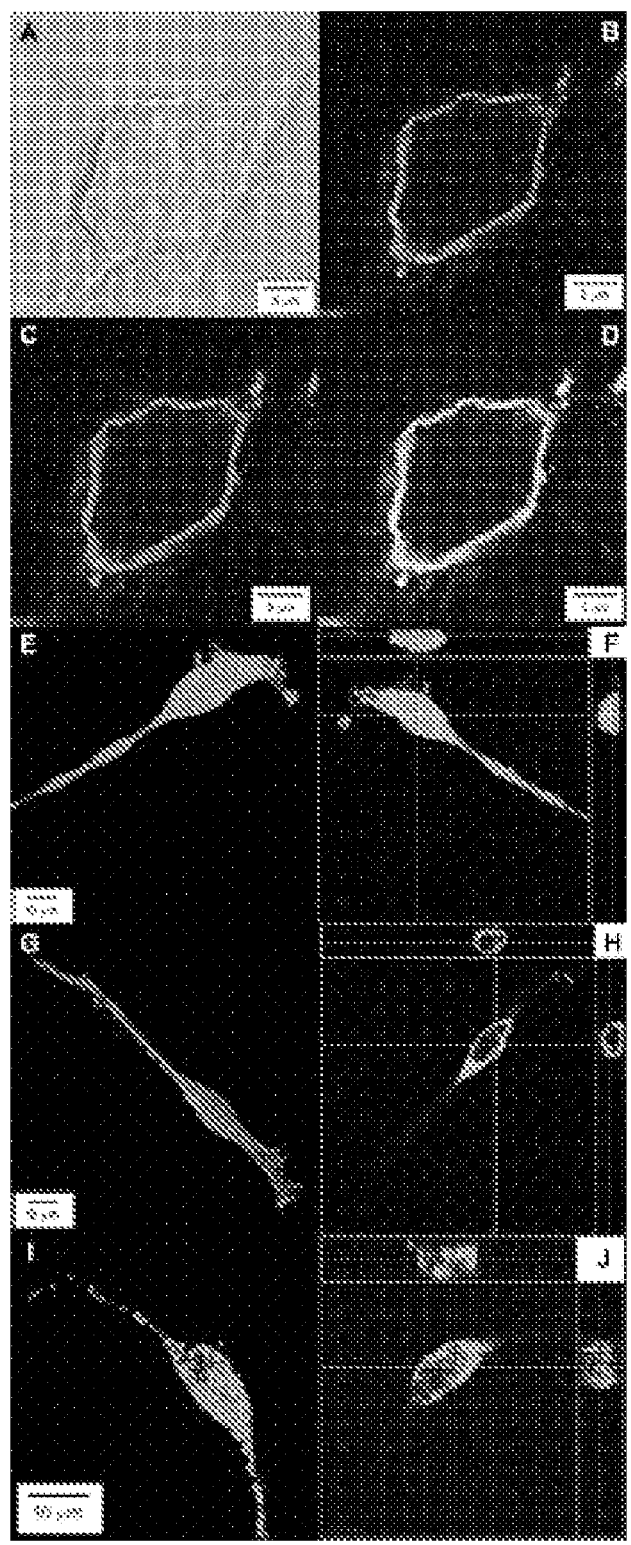
FIG. 5. γ6L is localized in or near the plasma membrane. A: Bright field image of individual HEK-293/Cav3.1 cells transfected with a vector encoding a GFP-γ6L fusion protein and a vector encoding a CFP protein that is targeted to cell membranes by a neuromodulin fragment. B: Same cell seen in panel A showing the distribution of the GFP-γ6L fusion protein. C: Same cell seen in panel A showing the distribution of CFP-neuromodulin. D: Composite image of panels B and C showing the co-localization of GFP-γ6L and CFP. Composite confocal microscopic images of representative HEK-293 cells transiently transfected with either GFP only, a GFP-γ6L fusion construct, or a GFP-γ7 fusion construct (E-J). E: Cell transfected with GFP only. G: Cell transfected with GFP-γ6L. I: Cell transfected with GFP-γ7. F, H, and J: Single horizontal cross-sectional images of cells seen in E, G, and I, respectively. GFP expressed alone was evenly distributed throughout the cell. GFP-γ6L appears to be localized to the plasma membrane, where it is evenly distributed. However, GFP-γ7 is distributed in small distinct regions throughout the cell. The localization of GFP, GFP-γ6L, and GFP-γ7 was the same in HEK-293 parental cells as in HEK-293/Cav3.1 cells (not shown).

FIG. 5. γ6L is localized in or near the plasma membrane. A: Bright field image of individual HEK-293/Cav3.1 cells transfected with a vector encoding a GFP-γ6L fusion protein and a vector encoding a CFP protein that is targeted to cell membranes by a neuromodulin fragment. B: Same cell seen in panel A showing the distribution of the GFP-γ6L fusion protein. C: Same cell seen in panel A showing the distribution of CFP-neuromodulin. D: Composite image of panels B and C showing the co-localization of GFP-γ6L and CFP. Composite confocal microscopic images of representative HEK-293 cells transiently transfected with either GFP only, a GFP-γ6L fusion construct, or a GFP-γ7 fusion construct (E-J). E: Cell transfected with GFP only. G: Cell transfected with GFP-γ6L. I: Cell transfected with GFP-γ7. F, H, and J: Single horizontal cross-sectional images of cells seen in E, G, and I, respectively. GFP expressed alone was evenly distributed throughout the cell. GFP-γ6L appears to be localized to the plasma membrane, where it is evenly distributed. However, GFP-γ7 is distributed in small distinct regions throughout the cell. The localization of GFP, GFP-γ6L, and GFP-γ7 was the same in HEK-293 parental cells as in HEK-293/Cav3.1 cells (not shown).

Figure 6:
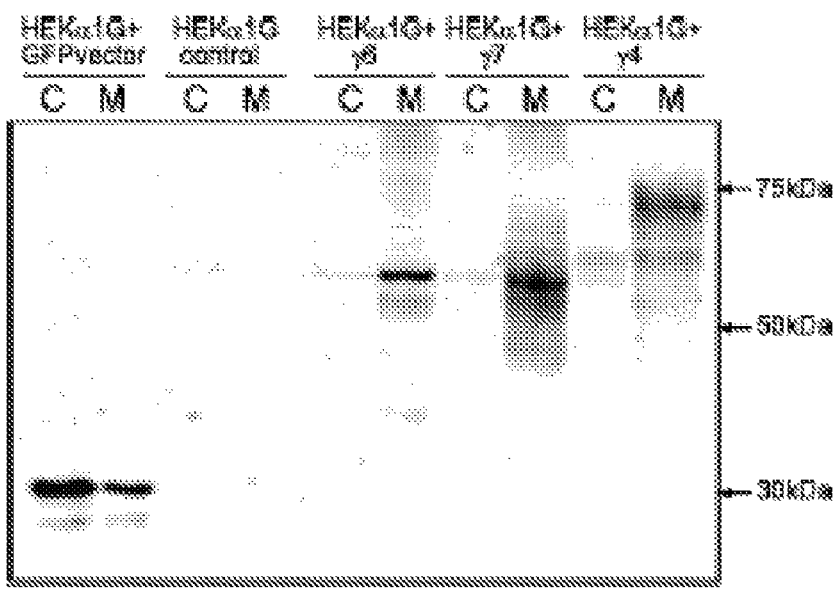
FIG. 6. Membrane localization of GFP-γ6L, GFP-γ7, and GPF-γ4 in HEK-293/Cav3.1. Western blot of cytosolic (C) and total membrane (M) fractions of HEK-293/Cav3.1 cells transfected with GFP and cells transfected with GFP fusion constructs for either γ6L, γ7, or γ4. Proteins were visualized using a monoclonal antibody to GFP. The GFP antibody detects appropriately sized fusion proteins for GFP-γ6L, GFP-γ7, and GFP-γ4 almost exclusively in the total membrane fraction of the cell lysate. When expressed alone, GFP protein is predominately expressed in the cytosolic fraction. No significant bands are seen in protein extracts from control cells (blank vector). Similar results were seen in HEK-293 parental cells, which were not stably transfected with Cav3.1 (data not shown).

FIG. 6. Membrane localization of GFP-γ6L, GFP-γ7, and GPF-γ4 in HEK-293/Cav3.1.Western blot of cytosolic (C) and total membrane (M) fractions of HEK-293/Cav3.1 cells transfected with GFP and cells transfected with GFP fusion constructs for either γ6L, γ7, or γ4. Proteins were visualized using a monoclonal antibody to GFP. The GFP antibody detects appropriately sized fusion proteins for GFP-γ6L, GFP-γ7, and GFP-γ4 almost exclusively in the total membrane fraction of the cell lysate. When expressed alone, GFP protein is predominately expressed in the cytosolic fraction. No significant bands are seen in protein extracts from control cells (blank vector). Similar results were seen in HEK-293 parental cells, which were not stably transfected with Cav3.1 (data not shown).

Figure 7:
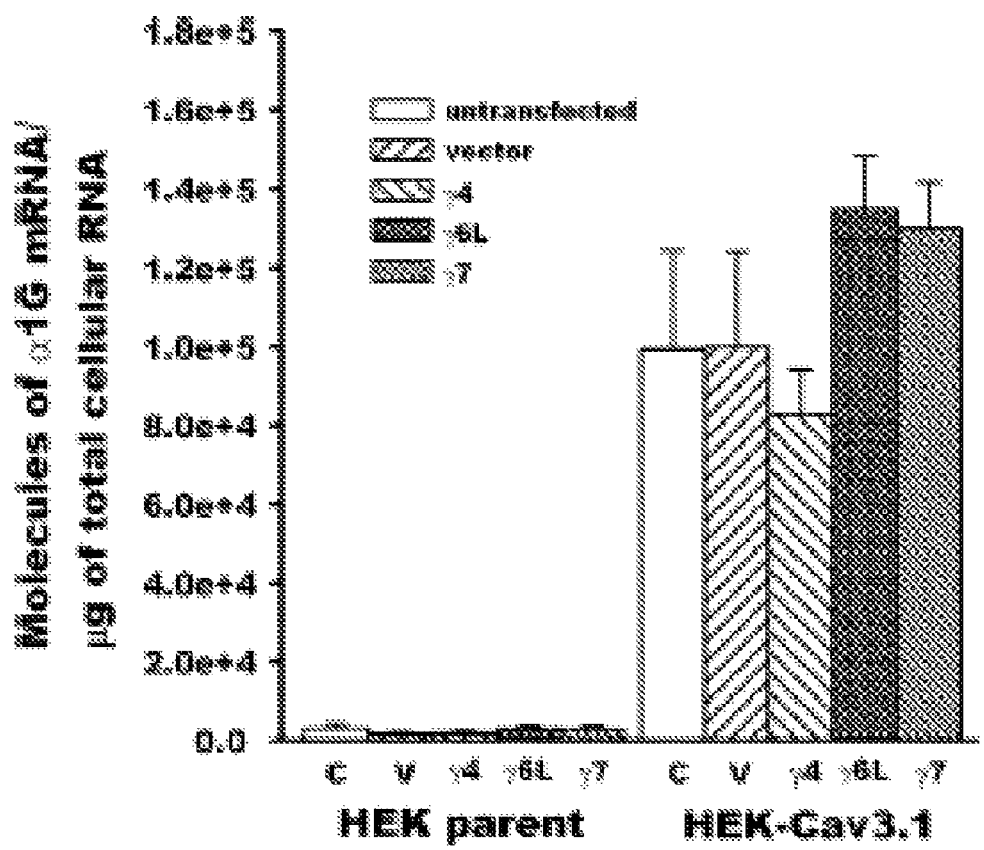
FIG. 7. Expression of γ subunits does not alter Cav3.1 mRNA levels. Equal amounts of either γ4, γ6L or γ7 DNA were transiently transfected into parental HEK-293 cells or HEK-293/Cav3.1. Control cells were transfected with the adCGI vector (V) or underwent a mock transfection (C, no DNA). Quantitative RT-PCR was performed to monitor the amount of Cav3.1 mRNA expressed in each of these groups. Transient transfection of γ4, γ6L or γ7 had no significant effect on Cav3.1 mRNA levels in either HEK-293 parental cells, or HEK-293/Cav3.1 when compared to vector control (V).

FIG. 7. Expression of γ subunits does not alter Cav3.1 mRNA levels. Equal amounts of either γ4, γ6L or γ7 DNA were transiently transfected into parental HEK-293 cells or HEK-293/Cav3.1. Control cells were transfected with the adCGI vector (V) or underwent a mock transfection (C, no DNA). Quantitative RT-PCR was performed to monitor the amount of Cav3.1 mRNA expressed in each of these groups. Transient transfection of γ4, γ6L or γ7 had no significant effect on Cav3.1 mRNA levels in either HEK-293 parental cells, or HEK-293/Cav3.1 when compared to vector control (V).

Figure 8:
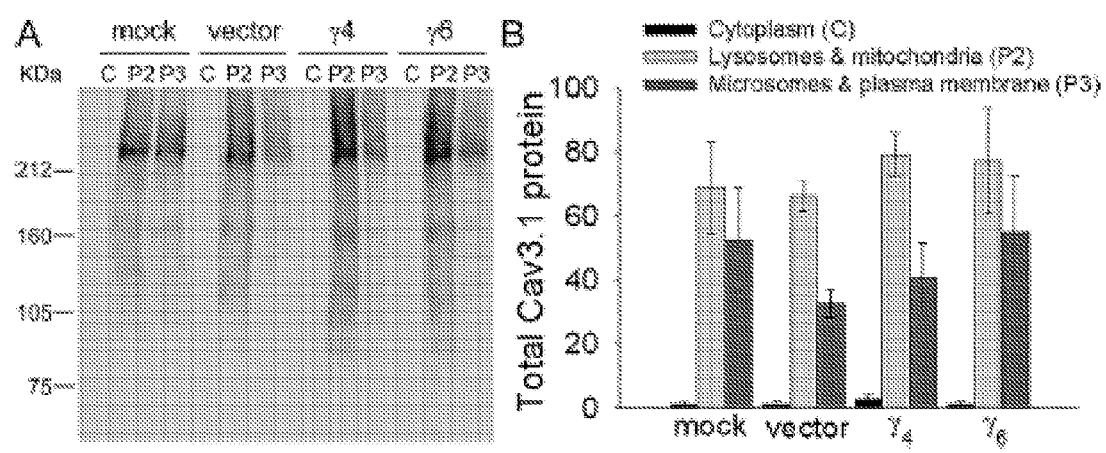
FIG. 8. Expression of γ subunits does not alter the amount of Cav3.1 protein. A: Representative Western blot showing expression of Cav3.1 protein in HEK-293/Cav3.1 cells and HEK-293/Cav3.1 cells transiently transfected with either blank vector, γ4 or with γ6L. Cell lysates were separated into cytoplasmic (C), lysosomal and mitochondrial (P2), and microsomal and plasma membrane (P3) fractions. Proteins were visualized using a polyclonal antibody for Cav3.1. The Cav3.1 protein was detected as a major band at approximately 260 kDa with the majority of protein in the membrane fractions. No Cav3.1 protein was detected in HEK-293 parental control cells not stably transfected with Cav3.1 (data not shown). B: The bar graph shows the relative amount of Cav3.1 protein expressed in each fraction normalized to percent of vector control (V) in HEK-293/Cav3.1 cells. The data represent three separate experiments. No statistically significant effect of either vector, or the γ4 or γ6 subunits on Cav3.1 protein expression was detected in any of the cell fractions individually, or in total cell Cav3.1 protein.

FIG. 8. Expression of γ subunits does not alter the amount of Cav3.1 protein. A: Representative Western blot showing expression of Cav3.1 protein in HEK-293/Cav3.1 cells and HEK-293/Cav3.1 cells transiently transfected with either blank vector, γ4 or with γ6L. Cell lysates were separated into cytoplasmic (C), lysosomal and mitochondrial (P2), and microsomal and plasma membrane (P3) fractions. Proteins were visualized using a polyclonal antibody for Cav3.1. The Cav3.1 protein was detected as a major band at approximately 260 kDa with the majority of protein in the membrane fractions. No Cav3.1 protein was detected in HEK-293 parental control cells not stably transfected with Cav3.1 (data not shown). B: The bar graph shows the relative amount of Cav3.1 protein expressed in each fraction normalized to percent of vector control (V) in HEK-293/Cav3.1 cells. The data represent three separate experiments. No statistically significant effect of either vector, or the γ4 or γ6 subunits on Cav3.1 protein expression was detected in any of the cell fractions individually, or in total cell Cav3.1 protein.

Abstract

The calcium channel gamma (γ) subunit family consists of eight members whose functions include modulation of high voltage-activated (HVA) calcium currents in skeletal muscle and neurons, and regulation of alpha-amino-3-hydroxy-5-methylisoxazole-4-propanoic acid (AMPA) receptor targeting. Cardiac myocytes express at least three γ subunits, γ4, γ6 and γ7, whose function(s) in the heart are unknown. Here we compare the effects of the previously uncharacterized γ6 subunit with that of γ4 and γ7 on a low voltage-activated calcium channel (Cav3.1) that is expressed in cardiac myocytes. Co-expression of both the long and short γ6 subunit isoforms, γ6L and γ6S, with Cav3.1 in HEK-293 cells significantly decreases current density by 49% and 69%, respectively. Two other γ subunits expressed in cardiac myocytes, γ4 and γ7, have no significant effect on Cav3.1 current. Neither γ6L, γ6S, γ4 nor γ7 significantly affect the voltage dependency of activation or inactivation or the kinetics of Cav3.1 current. Transient expression of γ6L in an immortalized atrial cell line (HL-1) significantly reduces the endogenous low voltage-activated current in these cells by 63%. Green fluorescent protein tagged γ6L is localized primarily in HEK-293 cell surface membranes where it is evenly distributed. Expression of γ6L does not affect the level of Cav3.1 mRNA or the amount of total Cav3.1 protein in transfected HEK-293 cells. These results demonstrate that the γ6 subunit has a unique ability to inhibit Cav3.1 dependent calcium current that is not shared with the γ4 and γ7 isoforms and is thus a potential regulator of cardiac low voltage-activated calcium current.

1. Introduction.

Calcium channels are multimeric proteins consisting of a pore forming α1 subunit and some combination of auxiliary β, α2δ and γ subunits [1]. Multiple genes and gene splice variants encode members of each subunit family. The extensive biophysical and pharmacological diversity of native calcium channels can be attributed to variation in their molecular identities [1-5]. While the main characteristics of calcium channels are determined by the identity of the α1 subunit, the auxiliary β and α2δ subunits are thought to regulate channel insertion into the surface membrane and to modify α1 subunit gating particularly for members of the Cav1 and Cav2 α1 subunit gene families [6-8]. The role of the γ subunits in modifying calcium channel function is still controversial. A number of studies indicate that γ subunits modulate calcium current in skeletal muscle and neurons [9]. However, other evidence demonstrates that some, but not all, γ subunits act as regulators of neuronal alpha-amino-3-hydroxy-5-methyl-isoxazole-4-propanoic acid (AMPA) receptor trafficking and may not regulate calcium current in those cells [10,11].

The calcium channel γ subunit family consists of eight genes that are predicted to produce proteins with four transmembrane segments and intracellular N- and C-terminals (reviewed in [12], see also [13-21]). Only three of these genes (γ4, γ6 and γ7) are robustly expressed in the rat heart [19].

Interestingly, these three isoforms have distinct structural features suggesting that they may have different functional roles in cardiac cells. The γ4 subunit contains a unique consensus PSD-95/DLG/ZO-1 (PDZ)-binding domain sequence (T-T-P-V) as the last four amino acids at the C-terminus. The γ4 isoform has been shown to regulate surface membrane localization of AMPA receptors in neurons [11]. The γ6 subunit does not contain this motif and has a C-terminal region that is significantly shorter than that of γ4. Moreover, the γ6 subunit is uniquely expressed in the heart as two isoforms and has an elongated N-terminus that is highly conserved across species [19]. The long isoform of γ6 contains four transmembrane segments while the short isoforms is missing a 46 amino acid sequence that includes the second and third transmembrane domains. Finally, the γ7 subunit lacks both the PDZ-binding motif of γ4 and the extensive N-terminal cytoplasmic region seen in γ6. The significance of the sequence differences seen in γ4, γ6 and γ7, if any, are unknown as is the potential role of these subunits in regulating cardiac myocyte function.

The first identified γ subunit, γ1, was purified from rat skeletal muscle and found to form a complex with the calcium channel α1 S (Cav1.1), $β_{1a}$, and $α_2δ_1$ subunits ([13, 22-25], see also review in [26]). This combination of subunits produces the high voltage-activated (HVA) L-type calcium current that is the dominant calcium current in adult skeletal muscle. This biochemical interaction was recently shown to be isoform specific since the γ2 subunit does not incorporate into the skeletal muscle HVA channel . Two groups have successfully silenced the γ1 subunit gene in mice and both describe similar effects on the HVA calcium current in skeletal muscle cells [28, 29]. The most notable phenotype in the γ1 knockout animals is a significant increase in the density of the HVA calcium current in skeletal muscle and a shift in its steady-state inactivation curve to positive potentials. These observations indicate that the γ1 subunit has an inhibitory effect on the Cav1.1 calcium current.

Interactions of γ subunits with low voltage-activated (Cav3) channels have not been studied extensively. However, the limited functional studies do indicate that γ subunits have inhibitory effects on the Cav3 channels similar to those described for Cav1 and Cav2 [20]. Extensive investigation of γ subunit interactions with Cav3 channels is needed to provide a complete understanding of the functional significance of the γ subunits in relation to the low voltage-activated calcium current. Regardless of the level of mechanistic understanding, the present invention provides a significant advance in defining discrete structural components that can usefully regulate calcium.

As an initial step in understanding the functions of calcium channel γ subunits expressed in cardiac myocytes, we have compared the effects of γ4, γ6L, γ6S and γ7 on low voltage-activated calcium currents produced by the expression of the α1 subunit Cav3.1 (α1G). Cav3.1 is expressed in rat cardiac myocytes and presumably contributes to the generation of the native cardiac LVA calcium current [30]. Our analysis indicates that the γ6 isoforms have a unique negative effect on Cav3.1 LVA current density that is not seen with either γ4 or γ7.

2. Materials and Methods 2.1 Cell Culture. HEK-293 cells were maintained in Dulbecco's minimum essential medium (DMEM) containing 4 mM L-glutamine, 4.5 g/l glucose and 1.5 g/l Na-bicarbonate (ATCC) supplemented with 10% fetal bovine serum (ATCC) and 100 U/ml:100 µg/ml:250 ng/ml of penicillin/streptomycin/amphotericin B (Life Technologies). HEK-293 cells stably transfected with Cav3.1 were a gift of Dr. L. Cribbs and Dr. E. Perez-Reyes and were maintained in media as above with the addition of 400 µg/ml G418 (Sigma). Cells were stored in a 5% CO2 incubator at 37° C. and passed every 7 days at a 1:5 dilution. Medium was changed every 3 days.

HL-1 cells were a gift from Dr. William C. Claycomb and were maintained as previously reported [31]. Briefly, HL-1 cells were grown in HL-1 medium containing Claycomb medium (JRH Biosciences) supplemented with 10% fetal bovine serum (JRH Biosciences), 0.1 mM norepinephrine (Sigma), 2 mM L-glutamine (Sigma), and 100 U/ml:100 µg/ml:250 ng/ml of penicillin/streptomycin/ amphotericin B (Life Technologies) in a humidified 5% CO2 incubator at 37° C. Cells were passed when confluent at a 1:3 dilution into flasks or plates pre-coated with a 1:80 dilution of fibronectin and 0.02% gelatin (Sigma). Cells from passages 86-108 were used for this study.

2.2. Sub-cloning of vectors for transfection in functional and localization studies. For studies on the electrophysiological effects of independently transcribed γ subunits in fluorescence-labeled cells, the coding regions of rat γ4, γ6L, γ6S, and γ7 subunit cDNAs [19] were subcloned into pCR II vectors (InVitrogen) by TA cloning. The accession numbers of these previously described genes are as follows: rat γ4 (AF361341), SEQ ID NO:47; rat γ6L (AF361343), SEQ ID NO:48; rat γ6S (AF361344), SEQ ID NO:49; and rat γ7 (AF361345), SEQ ID NO:50.

From pCR II vectors, rat γ4, γ6L, γ6S and γ7 subunit cDNAs were then transferred to an expression vector (adCGI, or "adenovirus-CMV-GFP-IRES"), a gift of Dr. Jeffrey R. Holt containing a CMV-driven promoter, the coding region of green fluorescent protein (GFP) and an internal ribosomal entry site (IRES). Each target γ subunit cDNA was linked at an EcoRI site immediately after the IRES for independent expression of GFP and specific γ subunit proteins, insuring that cells expressing GFP also expressed γ subunits and that the secondary and/or tertiary structure of the γ subunits was not affected as might be the case with the creation of a GFP-γ fusion protein. For analyzing the sub-cellular localization of γ subunit proteins, expression vectors encoding fusion proteins of GFP and specific γ subunits were made. The coding regions of all γ subunit cDNAs were linked in frame downstream of the GFP cDNA in a pEGFP-C1 vector (BD Clontech). A commercially available vector (pECFP-Mem, Clontech) encoding a modified cyan fluorescent protein (CFP) protein fused to the N-terminal 20 amino acids of the neuromodulin (GAP-43) protein was used as a membrane marker.

2.3. Transfection. Untransfected HEK-293 cells, HEK-293 cell lines stably transfected with Cav3.1, and HL-1 cells were transiently transfected with vectors containing γ subunit, GFP, and modified CFP cDNAs using Lipofectamine 2000 reagent (InVitrogen) as per the manufacturer's recommendations. HEK-293 cells were grown to 70-80% confluence before transfection. HL-1 cells were grown to 50-75% confluence before transfection.

2.4. Electrophysiology. Whole-cell calcium currents were recorded using an Axopatch-1 D patch clamp system and Clampex 8.0 software. Pipettes were fabricated from borosilicate glass and had typical resistances of 2-4 MΩ. The pipette solution contained (in mM): 130 NaCl, 10 EGTA, 2 MgCl2, 1 CaCl2, 10 HEPES, 3 Tris-ATP, and either 0.3 Li2GTP or 0.3 Tris-GTP, adjusted to pH 7.4 with NaOH and 280 mOsm with sucrose. The bath solution contained (in mM): 137 NaCl (for HEK-293 experiments) or 120 TEACl (for HL-1 experiments), 1 KCl, 1 MgCl2, 0.33 NaH2PO4, 2 CaCl2 (for HEK-293 experiments) or 5 CaCl2 (for HL-1 experiments), 10 glucose (for HL-1 experiments only), 10 HEPES, and 30 µM TTX (for HEK-293 experiments only), adjusted to pH 7.4 with NaOH (for HEK-293 experiments) or TEAOH (for HL-1 experiments) and 280 mOsm with sucrose. NaCl was used as the major salt in the pipette solution in order to eliminate any outward K+ currents. TTX was added to the bath solution to block Na+ currents, as a small inward current with kinetics resembling those of previously described Na+ currents was observed in untransfected parental HEK-293 control cells.

Recordings from HEK-293 cells were made 48-96 h post-transfection, at which time expression, as measured by GFP fluorescence, peaked. HL-1 cells were used for recording 24-36 h post-transfection. Current densities in HEK-293/Cav3.1 cell experiments were normalized to control for variation in current expression in the different frozen stocks of stable cell lines used. The current densities of different frozen stocks used for HEK-239/Cav3.1 experiments ranged from 49.1 to 58.5 pA/pF and were not significantly different from each other. HL-1 experiments were performed using a single stock of cells. All HEK-293 data are from current records in which pipette and whole-cell capacitance were about 100% compensated and series resistance was compensated to >80%. Whole-cell capacitance and series resistance were not compensated for HL-1 recordings as currents were typically <100 pA. Series resistance values were typically <10 MΧ, and no records were used in which the voltage error (as defined by Ver=Imax×Ra) was greater than 5 mV. The holding potential of all protocols used for HEK-293 cells was −100 mV except for steady-state inactivation protocols where the holding potential was −120 mV. The holding potential for protocols used for HL-1 cells was −90 mV. Current-voltage relationships for all HEK-293 and HL-1 cells were measured using 50 ms test depolarizations. Peak current amplitudes for activation curves were determined by fitting tail currents, elicited by stepping membrane voltage from varying test potentials to −60 mV, with the Boltzman equation. Test potential steps for activation protocols were of varied durations, corresponding to the time to peak of the elicited current. Inactivation curves were determined by fitting peak amplitudes of currents, observed in a test pulse to −20 mV, following 500 ms steps to varying potentials, with the Boltzman equation. Time to peak was determined using the current-voltage protocol described above. Inactivation time constants were determined by fitting the decay phase of currents to an exponential equation and deactivation time constants were determined by fitting the decay phase of tail currents to an exponential equation. Tail currents for Cav3.1 were found to be best fit by a double exponential. Currents were recorded at 40 kHz and on-line filtered at either 5 or 10 kHz. In some cases currents were off-line filtered at 1 kHz to further reduce noise. Current/voltage relationships and tail currents were recorded from HEK cells using an on-line P/−4 subtraction procedure. Calcium currents recorded from HL-1 cells were off-line leak subtracted. The average membrane capacitance of untransfected HEK-293 cells in pilot experiments was 12.5±1.4 pF (n=8). The capacitance of HL-1 cells ranged from 5.6 to 14.1 pF, with averages of 9.9±0.9 and 8.8±1.4 pF (mean±S.E.M.) for GFP-transfected and GFP-γ6 transfected cells (n=9 for each).

2.5. Statistical analysis. All data are reported as mean±S.E.M. and tested for significance by one-way ANOVA. A value of $P<0.05$ was considered significant and when significant P-values were encountered groups were compared using the Tukey posthoc test.

2.6. RT-PCR. Total RNA from cultured HL-1 cells and ventricular tissue of adult C57B2 mice was used for first strand cDNA synthesis using Superscript II reverse transcriptase (InVitrogen) in the presence of gene-specific primers or oligo-dT. PCR was carried out by cycling 35-39 times at 94° C. (1 min), 56 or 60° C. (30-60 s), and 72°C. (1 min), followed by a 10-min extension step at 72° C. A ribosomal RNA gene, PHE-7, was used as a housekeeping gene. All PCR products were subcloned and their identities confirmed by sequencing or restriction enzyme digest. For quantitative RT-PCR, the absolute abundance of Cav3.1 mRNA in HEK-293 cells was measured as described [30]. For all RT-PCR experiments a negative RT reaction was used as a control. See Table 1 for primer sets employed in RT-PCR (primers used for RT-PCR to detect α1 and γ subunits present in HL-1 cells and for quantitation of Cav3.1 mRNA in HEK-293 cells).

TABLE 1

RT-PCR primers.

| Item | SEQ ID NO: | | Sequence |
|---|---|---|---|
| Cav3.1 (HL-1) | 23 Fwd: | 5' | AAATGGTGGTGAAGATGG 3' |
|  | 24 Rev: | 5' | GACGAAGAAACAGAGCAG 3' |
| Cav3.1 (Quant.) | 25 Fwd: | 5' | GAGGACTGATGACCCCAAC 3' |
|  | 26 Rev: | 5' | ATGATCCGGTGACACAGG 3' |
| Cav3.2 | 27 Fwd: | 5' | TCCCCCGTCTACTTCGTCACCTTC 3' |
|  | 28 Rev: | 5' | GCGAGAGCATCCTGGACACAGATAC 3' |
| Cav1.2 | 29 Fwd: | 5' | GACCATCGGGAACATCGTAAT 3' |
|  | 30 Rev: | 5' | GGAAGAGGCGGAAGAAAGTGA 3' |
| γ2 | 31 Fwd: | 5' | ACC AGC AAG AAG AAC GAG 3' |
|  | 32 Rev: | 5' | AGA CAC GAA GAA GAT GCC 3' |
| γ3 | 33 Fwd: | 5' | CAA GTG ACA ATG AAA CCA G 3' |
|  | 34 Rev: | 5' | AGA GAC GAA GAA GAT GCC 3' |
| γ4 | 35 Fwd: | 5' | TGA CGA AGA CAA AAA GAA C 3' |
|  | 36 Rev: | 5' | TAA GGA GAG GAG GAA GAG G 3' |
| γ5 | 37 Fwd: | 5' | CAT AAT CCT CCC ACA GAA C 3' |
|  | 38 Rev: | 5' | TAC ACA GAC ATC ACC CC 3' |
| γ6 | 39 Fwd: | 5' | AGC TGC CAG GAG AAG CAA AC 3' |
|  | 40 Rev: | 5' | CTC TGC ACC TTT ACT GAG CAC 3' |
| γ7 | 41 Fwd: | 5' | TGG TGA CGG AAA ACA CGG AG 3' |
|  | 42 Rev: | 5' | AGA AAA GAG GAA GCA GCG AAG 3' |
| γ8 | 43 Fwd: | 5' | GGA GTC ATT GAA ACG CTG 3' |
|  | 44 Rev: | 5' | TCA TCA CCT GCT GTG AG 3' |
| PHE-7 | 45 Fwd: | 5' | CTG CGA AAG GCA AGG AGG AA 3' |
|  | 46 Rev: | 5' | TGG CTC CAC GAT CCT CAG CA 3' |

2.7. Fluorescent image detection. Expression vectors encoding GFP, GFP-γ6L fusion protein, or modified CFP were transfected using Lipofectamine 2000 reagent (InVitrogen) into HEK-293 cells plated on glass coverslips according to the manufacturer's instructions. The modified CFP contained the N-terminal 20 amino acids of neuromodulin (GAP 43, a post-translational membrane localization signal). Following transfection, cells were maintained in a 5% CO2 incubator at 37° C. for 48-72 h. Cells were then immersed in 4% paraformaldehyde, and washed three times with PBS before being mounted onto microscope slides using a ProLong Antifade kit (Molecular Probes). Cell were viewed on a Zeiss laser scanning confocal microscope with an oil-immersed 63×objective. GFP were visualized using excitation wavelengths of 488 and 418 nm, respectively. Images were obtained by z-sections with a step size of about 0.5 pm and analyzed using LSM 510 software (Carl Zeiss).

2.8. Western blot. Untransfected HEK-293 or HEK-293/Cav3.1 stably transfected cells were grown in 10-cm tissue culture dishes and transiently transfected when approximately 70% confluent. Twenty micrograms of each plasmid expression vector was transfected per 10-cm dish using Lipofectamine 2000 reagent (InVitrogen) as per the manufacturer's recommendations. Cells were harvested 72 h post-transfection and processed for immunoblot analysis according to Costagliola et al. [32] with some modification. Briefly, the cells were scraped from the plates in HBSS and centrifuged for 5 min at 60×g. All subsequent manipulations were done at 4° C. The cell pellets were resuspended in 1.0 ml of homogenization buffer (100 mM (NH4)2SO4, 20 mM Tris pH 7.5, 10% glycerol) supplemented with protease inhibitors (50 μg/ml leupeptin, 50 μg/ml aprotinin, 2.5 μg/ml pepstatin, 0.4 μM PMSF, 5 mM NaF and 8 μg/ml calpeptin). Samples were processed for 3 min using a motor driven homogenizer with a Teflon pestle. Cell lysates were centrifuged for 10 min at 600×g to remove nuclei and debris. The resulting supernatant was centrifuged again for 5 min at 15,000×g to obtain the P2 fraction (mitochondrial and lysosomal fraction). The remaining supernatant was centrifuged for 45 min at 125,000×g to obtain the P3 fraction (microsomal/plasmalemmal). Membrane fractions were resuspended in 400 µl of solubilization buffer (100 mM (NH4)2SO4, 20 mMTris pH 7.5, 10% glycerol, 1% N-dodecyl-maltoside and protease inhibitors listed above). Protein concentration of cell extracts was determined using BCA (Pierce, Rockford, Ill.). Protein samples (25 µg) were separated by SDS-PAGE on a 6% or 10% acrylamide gel containing 0.4% SDS to enhance resolution of membrane proteins. Samples were electrophoretically transferred to with γ6S, where mean peak current density decreased 69% (to 31%±13% of control value, n=5, P<0.01). In contrast, neither γ4 nor γ7 had a statistically significant effect on mean peak current density (mean percentages of control value were 93%±7%, n=10, P>0.05, and 99%±8%, n=11, P>0.05, for γ4 and γ7, respectively). Doubling the amount of γ4 DNA transfected into HEK-293/Cav3.1 cells resulted in neither a significant reduction nor enhancement of peak current (128%±19% of control value, FIG. 1C) suggesting that the failure of γ4 to reduce peak calcium current was not due to limited availability of this subunit. While there appears to be a slight hyperpolarizing shift in V-peak with γ6L co-expression it is within the limits of voltage error and is not statistically significant (see Table 2).

TABLE 2

Effects of γ subunits on the biophysical properties of Cav3.1 dependent currents in HEK-293 cells.

|  | Cav3.1 + adcgi | Cav3.1 + g6l | Cav3.1 + g6s | Cav3.1 + g4 | Cav3.1 + g7 |
|---|---|---|---|---|---|
| V peak (mV) | −29.5 ± 0.9 (n = 10) | −31.1 ± 3.1 (n = 9) | −27.0 ± 2.5 (n = 5) | −30.6 ± 1.5 (n = 9) | −24.1 ± 0.9 (n = 11) |
| Activation | | | | | |
| V 0.5 (mV) | −32.3 ± 1.5 (n = 9) | −36.3 ± 6.2 (n = 4) | −36.3 ± 6.2 (n = 4) | −37.3 ± 0.9 (n = 8) | −28.1 ± 1.2 (n = 11) |
| k | 13.3 ± 0.3 (n = 9) | 12.7 ± 1.5 (n = 4) | 12.7 ± 1.5 (n = 4) | 11.8 ± 0.5 (n = 8) | 11.1 ± 0.3 (n = 11) |
| Time to peak @ −20 mV (ms) | 5.7 ± 0.4 (n = 10) | 6.0 ± 0.8 (n = 5) | 6.4 ± 0.5 (n = 3) | 5.2 ± 0.5 (n = 9) | 7.0 ± 0.4 (n = 11) |
| Inactivation | | | | | |
| V 0.5 (mV) | −71.9 ± 1.4 (n = 8) | −78.5 ± 2.6 (n = 6) | −72.0 ± 5.9 (n = 3) | −79.2 ± 1.5 (n = 7) | −68.6 ± 1.4 (n = 10) |
| k | 5.4 ± 0.1 (n = 8) | 5.4 ± 0.3 (n = 6) | 5.9 ± 0.7 (n = 3) | 6.1 ± 0.2 (n = 7) | 6.0 ± 0.1 (n = 10) |
| Tau @ −20 mV (ms) | 19.8 ± 1.3 (n = 8) | 18.6 ± 1.1 (n = 6) | 22.9 ± 0.7 (n = 2) | 15.8 ± 0.7 (n = 7) | 17.2 ± 0.5 (n = 10) |
| Deactivation tau @ −100 mV (ms) | | | | | |
| Fast | 1.19 ± 0.19 (n = 9) | 1.54 ± 0.48 (n = 4) | 1.20 ± 0.06 (n = 3) | 1.84 ± 0.28 (n = 8) | 1.30 ± 0.10 (n = 11) |

PVDF membrane and subjected to immunoblot analysis according to standard protocols. Primary antibody for Cav3.1 was obtained from Alomone Laboratories (Jerusalem, Israel) and used at a concentration of 0.4 µg/ml. Monoclonal antibody GFP b2, which cross-reacts with CFP (Santa Cruz Biotechnology, Santa Cruz, Calif.) was used at 0.2 µg/ml. All incubations were done at room temperature in 1% milk/0.2% Tween 20 in TBS. The secondary antibodies, HRP conjugated goat anti-rabbit IgG and HRP conjugated goat anti-mouse IgG, for Cav3.1 and GFPb2 antibodies, respectively (Zymed, South San Francisco, Calif.), were diluted 1:20,000 in incubation solution. Protein products were visualized by ECL-Plus (Amersham/Pharmacia Biotech, Piscataway, N.J.) according to the manufacturer's directions and analyzed by phosphorimager detection.

3. Results.

3.1. Effects of γ subunits on current through heterologously expressed LVA calcium channels. Representative current traces elicited from a HEK-293/Cav3.1 cell show the typical voltage dependency and kinetics of Cav3.1 calcium current (FIG. 1A, Table 2). Averaged, normalized current-voltage relationships for the HEK-293/Cav3.1 cell line transiently transfected with either the blank adCGI vector, adCGI-γ6L or adCGI-γ6S show that co-expression of the γ6 subunits causes a significant decrease in peak calcium current. Co-expression of both γ6L and γ6S significantly reduced peak current density through Cav3.1 without significantly affecting the voltage at which peak current occurred. Peak current density decreased to 51%±17% of control value (n=10) in γ6L transfected cells (P<0.05, FIGS. 1B, C). A similar effect was seen In addition to decreasing peak current density it has been reported that γ subunits alter the voltage dependency of inactivation and the time course of inactivation of HVA currents [28, 33, 34]. However, analysis of the LVA currents recorded from HEK-293/Cav3.1 cells demonstrate that coexpression of the γ4, γ6L, γ6S, and γ7 subunits did not alter current kinetics or voltage dependency (FIG. 2, Table 2). Averaged data for Vmax, the voltage at which peak current occurred, the V0.5 and k for the voltage dependencies of activation and inactivation, the time to peak current at −20 mV, the time constant of inactivation at −20 mV, and the fast time constant of deactivation at −100 mV show no statistically significant differences (Table 2). The slow component of the time constant for deactivation accounted for less than 10% of the deactivation curve, did not show a consistent voltage dependency, and is not reported. Similarly there are no significant differences in the voltage dependency of inactivation or the voltage dependency of the time constant of deactivation for HEK293/Cav3.1 cells expressing either adCGI vector only, γ4, γ6L, γ6S, or γ7.

Thus the γ6 subunit isoforms have a unique ability, as compared to γ4 and γ7, to decrease Cav3.1 dependent LVA current density in stably transfected HEK-293 cells without modifying the biophysical properties of the remaining current.

3.2. Effects of γ6L on endogenous LVA current in a cardiac cell line. To study the effects of γ subunits on an endogenous LVA current we used HL-1 cells, a cell line derived from immortalized mouse atrial myocytes. Analysis of the α1 subunit mRNAs in HL-1 cells by RT-PCR (FIG. 3A) shows that HL-1 cells express both Cav3.1 and Cav3.2. Consistent with the observation that this sub-line of HL-1 cells did not express measurable HVA current, no Cav1.2 mRNA was detected (data not shown). We also used RT-PCR to determine whether murine HL-1 cells express endogenous γ subunits. Only the γ7 subunit mRNA was detected in HL-1 cells (FIG. 3B). Results were normalized to the expression of PHE-7, a constitutively active ribosomal housekeeping gene. As a positive control we used mRNA from mouse brain and ventricle, tissues known to express Cav3.1 and Cav3.2 as well as γ2-γ8. No products were amplified from HL-1 cells using primer sets for murine γ2, γ3, γ4, γ5 or γ8 (data not shown).

As with the HEK-293/Cav3.1 cells, HL-1 cells transfected with γ6 but not γ4 showed a significant decrease in LVA calcium current. Representative LVA current traces, averaged I-V relationships and averaged peak current densities for untransfected HL-1 cells and HL-1 cells transfected either with adCGI vector only, γ6L, or γ4 are shown in FIG. 4. The inhibitory effects of γ6L on average LVA current density was even more pronounced in HL-1 cells than in HEK-293/Cav3.1 cells. LVA current density in HL-1 cells was reduced by 63% from control value ($P<0.01$) following transfection with γ6L. Current density of untransfected HL-1 cells was 9.59±0.98 pA/pF, n=13, HL-1+vector was 9.18±1.79 pA/pF, n=9, HL-1+γ6L was 3.37±0.62 pA/pF, n=9, and HL-1+γ4 was 9.14±1.34 pA/pF, n=10. Current levels in HL-1 cells transiently transfected with γ subunit mRNA were too low to allow detailed analysis of voltage dependency and current kinetics.

3.3. Cellular localization of γ6L in single HEK/Cav3.1 cells. Both GFP tagged γ6L and plasma membrane specific CFPneuromodulin were transiently transfected into HEK-293/Cav3.1 cells and visualized for cellular location by confocal microscopy (FIG. 5). Panel 5A is a bright field image of a HEK-293 cell expressing both GFP-γ6L and CFPneuromodulin. Using separate filter sets, the expression of GFP-γ6L and CFP-neuromodulin was imaged independently (5B, C) showing that both the γ fusion protein and the plasma membrane marker are closely associated with the cell surface. This observation is supported by the overlay of panels 5B and C, which shows co-localization of the two proteins (5D). Thus, GFP-γ6L and the CFP-neuromodulin exhibited similar distributions in transfected cells confirming that γ6L is localized predominantly in or near the plasma membrane. Panels 5E and F show composite and cross-sectional images, respectively, of an individual HEK-293 cell expressing GFP alone demonstrating that GFP is uniformly expressed throughout the cell. Panels 5G and H show composite and cross-sectional images, respectively, of an individual HEK-293 cell expressing GFP-γ6L, demonstrating its localization at or near the plasma membrane. Panels 5I and J show composite and cross-sectional images, respectively, of an individual HEK-293 cell expressing GFP-γ7. Subunit γ7 is distributed throughout the cell in small distinct regions in contrast to GFP-γ6L which is evenly distributed at the plasma membrane. The localization of GFP, GFP-γ6L and GFP-γ7 was also observed in HEK-293 cells not stably transfected with Cav3.1 and found to be the same as for HEK-293/Cav3.1 cells (data not shown).

3.4. Western blot analysis of GFP-tagged γ subunits in cytosolic and membrane fractions. To confirm that γ subunits are membrane associated, GFPfusion constructs encoding either GFP-γ6L, GFP-γ7 or GFP-γ4 were transfected into HEK-293/Cav3.1 cells. Proteins were detected using a monoclonal antibody to GFP. The anti-GFP antibody detected appropriately sized fusion proteins for GFP-γ6L, GFP-γ7 and GFP-γ4 predominantly in cell membrane fractions (FIG. 6). The adCGI vector itself produces only the 30 kDa vectorial GFP protein that is detected mostly in the cytosolic fraction. No products were visualized in the extracts from HEK-293/Cav3.1 untransfected parent cells. Similar results were also seen when these constructs were transfected in HEK-293 parental cells not stably transfected with Cav3.1 (data not shown).

3.5. Effects of γ subunit co-expression on Cav3.1 mRNA and protein. We investigated whether changes in either Cav3.1 mRNA or protein levels can explain the decrease in Cav3.1 current when co-expressed with γ6. Quantitative RT-PCR was performed to monitor the amount of Cav3.1 mRNA expressed in untransfected HEK-293 cells and HEK-293/Cav3.1 cells transfected either γ4, γ6L or γ7 (FIG. 7). Overexpression of γ4, γ6L and γ7 had no significant effect ($P>0.05$) on the level of Cav3.1 message as compared to transfection with adCGI vector alone in HEK-293/Cav3.1 cells. Amounts of Cav3.1 transcript ranged from $1.0\pm0.24\times10^5$ molecules of Cav3.1 mRNA per µg of total cellular RNA (vector only) to $0.83\pm0.11\times10+5$ (γ4 over-expression), $1.3\pm0.14\times10+5$ (γ6L over-expression) and $1.3\pm0.12\times10+5$ (γ7 overexpression). No appreciable amount of Cav3.1 mRNA was detected in parental HEK-293 cells. These results demonstrate that transient transfection with γ6 does not affect Cav3.1 gene transcription in HEK-293 cells.

To determine whether the γ subunits modulate Cav3.1 protein levels, protein samples from HEK 293/Cav3.1 cells expressing γ4, γ6L and γ7 were analyzed using western blot analysis with an anti-Cav3.1 antibody. An exemplar blot (FIG. 8A) indicates that Cav3.1 protein is highly expressed in membrane fraction of the cell lysate and runs predominantly as a band of about 260 kDa. No Cav3.1 protein was detected in parental HEK-293 control cells (data not shown). Similar results were obtained for the other γ subunits as shown in the averaged data from three independent experiments by quantifying the 260 kDa band (FIG. 8B). The relative amounts of Cav3.1 protein expressed in cytosolic and membrane fractions for mock transfection, vector, γ6L, and γ4 were normalized to cell extracts from cells transfected with adCGI vector alone. The co-expression of the γ subunits does not significantly alter Cav3.1 protein levels in either the cytoplasm; lysosomal and mitochondrial membrane fraction; or microsomal and plasma membrane fraction ($P>0.05$). Additionally, there is no significant effect of γ subunit expression on the total amount of Cav3.1 protein expressed in all fractions combined from HEK-293/Cav3.1 cell lysates ($P>0.05$). Most importantly, γ6L causes no down-regulation of Cav3.1 protein expression when transfected in Cav3.1/HEK-293 cells.

4. Discussion

In this study, we describe the functional effects of the three γ subunits that are robustly expressed in rat cardiac myocytes on current produced by a heterologously expressed LVA calcium current and on endogenous LVA current in an atrial derived cell line. Our results provide the first functional analysis of the γ6 subunit and show that this subunit has unique inhibitory effects on the density of Cav3.1 dependent LVA currents not seen with the other γ isoforms expressed in the heart.

Our finding that γ6 co-expression reduces LVA calcium current density is consistent with previous reports that γ subunit co-expression generally reduces current density through HVA channels [35, 36]. In contrast to the effect of γ6, neither γ4 nor γ7 had statistically significant effects on Cav3.1 dependent calcium current. These findings are in agreement with a previous report showing that γ4 had no effect on current density through an LVA channel, Cav3.3 (α1I), expressed in HEK-293 cells [20]. However, a profound effect of human γ7 on the expression of Cav2.2 dependent HVA current has been previously reported [36]. Thus, it is possible that the functional effects of specific γ subunits are dependent on the α1 subunit with which they interact. Our data clearly show that both of the γ6 isoforms have a much more robust effect on LVA current density than either γ4 or γ7 under the same experimental conditions supporting the conclusion that the effects of γ6 are distinct from those of other cardiac γ subunits with regards to current arising from Cav3.1 α1 subunits. This difference suggests that there may be unique interactions between specific α1 and γ subunits or other associated proteins.

In addition to altering calcium channel function, γ subunits containing C-terminal PDZ-binding domains have been shown to be important regulators of ligand gated ion channel trafficking [11, 37]. The γ2, γ3, γ4, and γ8 subunits mediate surface membrane localization of AMPA receptors in neurons and make up a family of transmembrane AMPA receptor regulatory proteins, TARPs [11]. Neither the kγ1 nor the γ5 subunit regulated AMPA receptor localization demonstrating that these subunits are likely to have different cellular functions. Although not specifically tested in that study, the γ6 and γ7 subunits, which are expressed in cardiac muscle, may not be members of the TARP family. They lack the consensus PDZ-binding motif of the TARP proteins and are closely related to γ1 and γ5 phylogenetically [19]. It is interesting that several of the γ subunits found to be involved in AMPA receptor trafficking have previously been shown to modulate calcium current suggesting that individual γ subunits may have pleiotropic effects in the same cells [10, 21, 36].

Our results show that over-expression of γ6L significantly reduces endogenous LVA current in the HL-1 cell line. The similarity of the γ6 effects on current in both HEK-293 and HL-1 cells, an atrial cell line, suggests that γ6 effects are independent of cell type and that our HEK-293 studies are physiologically relevant to native cardiac tissue. Cardiac LVA current density changes dramatically during postnatal growth and in response to hormonal changes and pathophysiological insults [38-40] although the mechanisms by which LVA current expression in the heart is regulated are not well understood. Our results suggest that repression of LVA calcium current density by the γ6 subunit could play a role in the regulation of this current.

A number of different mechanisms that might explain the effect of the γ6 subunits on LVA calcium current can be ruled out by our data. Since robust effects of γ6 are seen in HEK-293/Cav3.1 cells where non-coding (regulatory) genomic sequence does not flank the heterologously expressed gene it is unlikely that the γ subunits act as regulators of transcription. We have confirmed this idea by showing that γ6 caused no change in the levels of Cav3.1 mRNA in Cav3.1/HEK293 cells. This result is consistent with the demonstration that native LVA current in thalamocortical relay neurons of γ2−/− mice is significantly increased without concurrent changes in the mRNA levels of any Cav3 α1 subunits [41]. Western analysis indicates that there is no change in the amount of Cav3.1 protein in either the lysosomal/mitochondria or the microsomal/plasmalemmal fractions of homogenized cells transiently transfected with γ6L even though LVA calcium current is decreased significantly. Thus, it appears that in HEK/Cav3.1 cells the γ6L dependent decrease in LVA calcium current density is not the result of a decrease in total Cav3.1 protein.

What mechanisms might then account for the decrease in Cav3.1 current that results from co-expression with γ6? It is also possible that the γ6 subunit uniformly alters the biophysical properties of all channels thus decreasing current density. Freise et al. [28] suggested that γ subunits decrease the open probability of channels to account for the increase in Cav1.1 (α1S) dependent calcium current in skeletal muscle cells from γ1 knock out mice, where the amount of Cav1.1 protein was biochemically shown to be unchanged. More recently Lacinova and Klugbauer [42] have shown that the a2d2a and γ5 subunits modestly alter the gating currents of Cav3.1 channels thus altering current kinetics. Since we did not see any changes in the activation and kinetic properties of the LVA current our data do not provide any experimental evidence to support this mechanism although we cannot rule it out completely without more detailed biophysical analysis. Thus, it remains to be determined if an alteration of channel gating can explain the decrease in Cav3.1 current by γ6. Another possibility is that the γ6 subunit causes a decrease in the number of channels normally available for activation. In this case the remaining current would have a smaller peak amplitude but unaltered kinetics consistent with our data. A decrease in channel availability could entail a change in trafficking of channels to the surface membrane [43]. It also could be produced if a subgroup of channels in the membrane were to become electrically silent under the influence of γ6. These possible mechanisms are currently being investigated.

The region(s) of the γ6 subunit involved in the interaction with α1 subunits are unclear. Arikkath et al. [27] used a chimeric strategy to show that the N-terminal half of γ1, including transmembrane segments 1 and 2, is necessary for its interaction with Cav1.1. Since γ1 is highly homologous to γ6 and we have shown that both γ6L and γ6S have the same functional effects on Cav3.1, it is likely that transmembrane regions 2 and 3 as well as the sequence linking these two regions is not responsible for the interaction of either γ1 or γ6 with α1 subunits. These results suggest that an important α1 interaction site for γ1 and γ6 may lie within the N-terminal region up to and including the first transmembrane segment. However, these results do not preclude the existence of other α1-γ interaction sites.

In summary, these studies provide the first comparative functional analysis of the calcium channel γ subunits that are expressed in cardiac muscle and show that the γ6 subunit is unique in its ability to decrease LVA calcium current density. This functional specificity makes the γ6 subunit a useful target for interventions seeking to modify LVA calcium current in the heart. Modification of other types of calcium regulation in the heart and elsewhere can also be achieved.

References Cited in Example 1

[1] Catterall W A. Structure and regulation of voltage-gated Ca2+ channels. Annu Rev Cell Dev Biol 2000;16:521-55.

[2] De Waard M, Gurnett C A, Campbell K P. Structural and functional diversity of voltage-activated calcium channels. Ion Channels 1996;4:41-87.

[3] Moreno H, Rudy B, Llinas R. Beta subunits influence the biophysical and pharmacological differences between P- and Q-type calcium
 currents expressed in a mammalian cell line. Proc Natl Acad Sci USA 1997;94(25):14042-7.

[4] Fletcher C F, Copeland N G, Jenkins N A. Genetic analysis of voltagedependent calcium channels. J Bioenerg Biomembr 1998;30(4):387-98.

[5] Hofmann F, Lacinova L, Klugbauer N. Voltage-dependent calcium channels: from structure to function. Rev Physiol Biochem Pharmacol 1999;139(2):33-87.

[6] Wei X Y, Perez-Reyes E, Lacerda A E, Schuster G, Brown A M, Birnbaumer L. Heterologous regulation of the cardiac Ca2+ channel alpha 1 subunit by skeletal muscle beta and gamma subunits. Implications for the structure of cardiac L-type Ca2+ channels. J Biol Chem 1991; 266(32):21943-7.

[7] Williams M E, Feldman D H, McCue A F, Brenner R, Velicelebi G, Ellis S B. Structure and functional expression of alpha 1, alpha 2, and beta subunits of a novel human neuronal calcium channel subtype. Neuron 1992;8(1):71-84.

[8] Klugbauer N, Lacinova L, Marais E, Hobom M, Hofmann F. Molecular diversity of the calcium channel alpha2delta subunit. J Neurosci 1999;19(2):684-91.

[9] Arikkath J, Campbell K P. Auxiliary subunits: essential components of the voltage-gated calcium channel complex. Curr Opin Neurobiol 2003;1 3(3):298-307.

[10] Sharp A H, Black 3rd J L, Dubel S J, Sundarraj S, Shen J P, Yunker A M. Biochemical and anatomical evidence for specialized voltagedependent calcium channel gamma isoform expression in the epileptic and ataxic mouse, stargazer. Neuroscience 2001 ;105(3):599-617.

[11] Tomita S, Chen L, Kawasaki Y, Petralia R S, Wenthold R J, Nicoll A. Functional studies and distribution define a family of transmembrane AMPA receptor regulatory proteins. J Cell Biol 2003;161(4):805-16.

[12] Kang M G, Campbell K P. Gamma subunit of voltage-activated calcium channels. J Biol Chem 2003;278(24):21315-8.

[13] Jay S D, Ellis S B, McCue A F, Williams M E, Vedvick T S, Harpold M M . Primary structure of the gamma subunit of the DHPsensitive calcium channel from skeletal muscle. Science 1990;248(4954):490-2.

[14] Letts V A, Felix R, Biddlecome G H, Arikkath J, Mahaffey C L, Valenzuela A. The mouse stargazer gene encodes a neuronal Ca2+-channel gamma subunit. Nat Genet 1998;19(4):340-7.

[15] Black 3rd J L, Lennon V A. Identification and cloning of putative human neuronal voltage-gated calcium channel gamma-2 and gamma-3 subunits: neurologic implications. Mayo Clin Proc 1999; 74(4):357-61.

[16] Burgess D L, Davis C F, Gefrides L A, Noebels J L. Identification of three novel Ca(2+) channel gamma subunit genes reveals molecular diversification by tandem and chromosome duplication. Genome Res 1999;9(12):1204-13 [in Process Citation].

[17] Klugbauer N, Dai S, Specht V, Lacinova L, Marais E, Bohn G. A family of gamma-like calcium channel subunits. FEBS 2000;470(2): 189-97.

[18] Burgess D L, Gefrides L A, Foreman P J, Noebels J L. A cluster of three novel Ca2+ channel gamma subunit genes on chromosome 19q13.4: evolution and expression profile of the gamma subunit gene family. Genomics 2001 ;71 (3):339-50.

[19] Chu P J, Robertson H M, Best P M. Calcium channel gamma subunits provide insights into the evolution of this gene family. Gene 2001; 280(1-2):37-48.

[20] Green P. Kinetic modification of the alpha1I subunit-mediated T-type Ca2+ channel by a human neuronal Ca2+ channel gamma subunit. J Physiol 2001 ;533(2):467-78.

[21] Rousset M, Cens T, Restituito S, Barrere C, Black 3rd J L, McEnery M W, et al. Functional roles of gamma2, gamma3 and gamma4, three new Ca2+ channel subunits, in P/Q-type Ca2+ channel expressed in Xenopus oocytes. J Physiol 2001 ;532(Pt 3):583-93.

[22] Curtis B M, Catterall W A. Purification of the calcium antagonist receptor of the voltage-sensitive calcium channel from skeletal muscle transverse tubules. Biochemistry 1984; 23(10):2113-8.

[23] Flockerzi V, Oeken H J, Hofmann F, Pelzer D, Cavalie A, Trautwein W. Purified dihydropyridine-binding site from skeletal muscle t-tubules is a functional calcium channel. Nature 1986;323(6083):66-8.

[24] Leung D W, Spencer S A, Cachianes G, Hammonds R G, Collins C, Henzel W J. Growth hormone receptor and serum binding protein: purification, cloning and expression. Nature 1987;330(6148):537-43.

[25] Campbell K P, Leung A T, Imagawa T. Structural characterization of the nitrendipine receptor of the voltage-dependent Ca2+ channel: evidence for a 52,000 Da subunit. J Cardiovasc Pharmacol 1988; 12(Suppl 4):S86-S90.

[26] Catterall W A. Molecular properties of voltage-sensitive sodium and calcium channels. Braz J Med Biol Res 1988;21(6):1129-44.

[27] Arikkath J, Chen C C, Ahern C, Allamand V, Flanagan J D, Coronado R. Gamma 1 subunit interactions within the skeletal muscle L-type voltage-gated calcium channels. J Biol Chem 2003;278(2): 1212-9.

[28] Freise D, Held B, Wissenbach U, Pfeifer A, Trost C, Himmerkus N. Absence of the gamma subunit of the skeletal muscle dihydropyridine receptor increases L-type Ca2+ currents and alters channel inactivation properties. J Biol Chem 2000;275(19):14476-81.

[29] Ahern C A, Powers P A, Biddlecome G H, Roethe L, Vallejo P, Mortenson L. Modulation of L-type Ca2+ current but not activation of Ca2+ release by the gamma1 subunit of the dihydropyridine receptor of skeletal muscle. BMC Physiol 2001;1 (1):8.

[30] Larsen J K, Mitchell J W, Best P M. Quantitative analysis of the expression and distribution of calcium channel alpha 1 subunit mRNA in the atria and ventricles of the rat heart. J Mol Cell Cardiol 2002;34(5): 519-32.

[31] Claycomb W C, Lanson Jr. N A, Stallworth B S, Egeland D B, Delcarpio J B, Bahinski A. HL-1 cells: a cardiac muscle cell line that contracts and retains phenotypic characteristics of the adult cardiomyocyte. Proc Natl Acad Sci USA 1998;95(6):2979-84.

[32] Costagliola S, Panneels V, Bonomi M, Koch J, Many M C, Smits G. Tyrosine sulfation is required for agonist recognition by glycoprotein hormone receptors. EMBO J 2002;21(4):504-13.

[33] Held B, Freise D, Freichel M, Hoth M, Flockerzi V. Skeletal muscle L-type Ca(2+) current modulation in gamma1-deficient and wildtype murine myotubes by the gamma1 subunit and cAMP. J Physiol 2002; 539(Pt 2):459-68.

[34] Eberst R, Dai S, Klugbauer N, Hofmann F. Identification and functional characterization of a calcium channel gamma subunit. Pflug Arch 1997;433(5):633-7.

[35] Kang M G, Chen CC, Felix R, Letts V A, Frankel W N, Mori Y. Biochemical and biophysical evidence for gamma 2 subunit association with neuronal voltage-activated Ca2+ channels. J Biol Chem 2001; 276(35):32917-24.

[36] Moss F J, Viard P, Davies A, Bertaso F, Page K M, Graham A. The novel product of a five-exon stargazin-related gene abolishes Ca(V) 2.2 calcium channel expression. EMBO J 2002;21 (7):1514-23.

[37] Chen L, Chetkovich D M, Petralia R S, Sweeney N T, Kawasaki Y, Wenthold R J. Stargazin regulates synaptic targeting of AMPA receptors by two distinct mechanisms. Nature 2000;408(6815):936-43.

[38] Nuss H B, Houser S R. T-type Ca2+ current is expressed in hypertrophied adult feline left ventricular myocytes. Circ Res 1993;73(4): 777-82.

[39] Xu X, Best P M. Increase in T-type calcium current in atrial myocytes from adult rats with growth hormone-secreting tumors. Proc Natl Acad Sci USA 1990;87:4655-9.

[40] Xu X, Best P M. Postnatal changes in T-type calcium current density in rat atrial myocytes. J Physiol 1992;454: 657-72.

[41] Zhang Y, Mori M, Burgess D L, Noebels J L. Mutations in high voltage activate calcium genes stimulate low voltage activated currents in mouse thalamic relay neurons. J Neurosc 2002;22:6362-71.

[42] Lacinova L, Klugbauer N. Modulation of gating currents of the Ca(v) 3.1 calcium channel by alpha 2 delta 2 and gamma 5 subunits. Arch Biochem Biophys 2004;425(2):207-13.

[43] Dubel S J, Altier C, Chaumont S, Lory P, Bourinet E, Nargeot J. Plasma membrane expression of T-type calcium channel alpha 1 subunits is modulated by HVA auxiliary subunits. J Biol Chem 2004;279:29263-9.

EXAMPLE 2

The N-Terminal Transmembrane Domain of the Calcium Channel gamma$_6$ Subunit Mediates its Functional Effect on Low-Voltage Activated Calcium Current (Cav3.1)

Abstract

Specific calcium channel γ (gamma) subunit isoforms have been shown to associate with and modulate the function of the channel complex. Other isoforms from this gene family assist in the membrane localization and synaptic trafficking of AMPA receptors. We have shown that the gamma$_6$ subunit inhibits the expression of low voltage-activated current in both a heterologous expression system and a cardiac myocyte cell line. However, the γ$_4$ and γ$_7$ subunits, which are expressed concurrently in cardiac myocytes along with γ$_6$, have no effect on low voltage-activated current. The γ$_6$, γ$_4$, and γ$_7$ subunits are phylogenetically divergent from one another. The γ$_6$ subunit is most closely related to the γ$_1$ subunit from the skeletal muscle calcium channel complex and γ$_4$ is a transmembrane AMPA receptor regulatory protein (TARP). Using a chimeric strategy we show here that the functional distinction between γ$_6$ and γ$_4$ is mediated by a region within the first transmembrane domain (TM) of these proteins. The insertion of only TM1 from γ$_6$ into γ$_4$ can confer the regulatory function of γ$_6$ onto γ$_4$. Conversely, by substituting only the TM1 from γ$_4$ into γ$_6$ the calcium channel regulatory function of γ$_6$ can be removed. Electrophysiological analysis of a series of γ$_6$/γ$_4$ chimeras and the use of a mammalian 2-hybrid assay confirm the functional significance of the TM1 region of γ subunits.

Introduction

Voltage dependent calcium ion channels are essential for excitation contraction coupling, electrical impulse transmission and hormone release and may play significant roles in the expression of some genes and in cellular proliferation. Structurally, calcium channels are heteromultimers thought to be composed of four subunits: α$_1$, β, α$_2$δ, and γ (alpha$_1$, beta, alpha$_2$delta, and gamma). The α$_1$ (alpha$_1$) subunit is the pore forming subunit of the channel, while the accessory subunits modulate channel expression and functional properties.

The dihydropyridine receptor from skeletal muscle, which was the first calcium channel described, contains all three of these accessory subunits (Curtis and Catterall 1984; Flockerzi, Oeken et al. 1986). However, it is not clear if all of these subunits are components of the channel complex in tissues other than skeletal muscle. The majority of high voltage-activated (HVA) channels are thought to contain β (beta) and α$_2$δ (alpha$_2$delta) subunits, as these subunits are often required for the functional expression of HVA channels with normal functional properties (see Arikkath and Campbell 2003 for review) (Arikkath and Campbell 2003). There is recent evidence that low voltage-activated (LVA) channel complexes may also be modulated by β (beta) and α$_2$δ (alpha$_2$delta) subunits (Lacinova and Klugbauer 2004).

The γ (gamma) subunits are the least well studied of the accessory subunits. In some cases γ subunits have been shown to modulate channels when heterologously co-expressed. However, whether γ subunits are functional components of channels outside of skeletal muscle is not definitively known.

Members of the calcium channel γ subunit family may play several distinct roles in the cell with some γ subunits having multiple functions. Some members of this family appear to be regulatory components of calcium channels, and some members are essential for regulating the trafficking of AMPA (alpha-amino-3-hydroxy-5-methyl-4-isoxazoleproprionate) receptors to the synapse (Curtis and Catterall 1984; Flockerzi, Oeken et al. 1986; Arikkath, Chen et al. 2003; Tomita, Chen et al. 2003). The γ subunits which regulate AMPA receptor trafficking are known as transmembrane AMPA receptor regulatory proteins (TARP's). Several of the TARP's are also known to have inhibitory effects on high voltage-activated calcium channel function when co-expressed with these channels (Klugbauer, Dai et al. 2000; Moss, Viard et al. 2002). Whether the members of the TARP subgroup represent a functionally distinct sub-family that is homologous in structure to the remainder of γ subgroups, or whether the TARP's serve multiple roles has yet to be determined.

The γ subunit family can be divided phylogenetically into three general groups as seen in FIG. 9 which have the relationship ((γ$_1$, γ$_6$)((γ$_2$, γ$_3$, γ$_4$, γ$_8$)(γ$_5$, γ$_7$))) (Chu, Robertson et al. 2001). The γ$_2$, γ$_3$, γ$_4$, and γ$_8$ subunits are all members of the TARP subgroup (Tomita, Chen et al. 2003). The subunits γ$_1$, γ$_2$, γ$_3$, γ$_4$, and γ$_7$ have all been previously shown to have generally inhibitory affects on calcium channel function, with the most commonly reported effects being a hyperpolarizing shift in the inactivation curve, an acceleration of inactivation, and a reduction in current density (Held, Freise et al. 2002) (Arikkath, Chen et al. 2003) (Freise, Held et al. Biol Chem 2000 May 12) (Singer, Biel et al. 1991; Eberst, Dai et al. 1997) (Letts, Felix et al. 1998; Kang, Chen et al. 2001) (Green 2001) (Klugbauer, Dai et al. 2000) (Moss, Viard et al. 2002).

We have previously shown that the novel γ$_6$ subunit decreases expression of low voltage-activated calcium current when co-expressed with Cav3.1 and Cav3.2 in a heterologous expression system without altering the voltage-dependency or kinetics of the remaining current (Hansen, Chien et al. 2004). Neither γ$_4$ nor γ$_7$ had any effect on currents through the Cav3 channels. This inhibitory effect of γ$_6$ was also demonstrated in an atrial myocyte derived cell line, HL-1, where γ$_4$ again showed no effect. In this previous study we demonstrated, using quantitative RT-PCR, fluorescence confocal microscopy, and western blotting that the effect of the γ$_6$ subunit was not due to an effect of γ$_6$ on either transcription or translation. The results of this study also suggested that γ$_6$ did not affect Cav3 trafficking, although this was not proven definitively.

Phylogenetically, the γ$_4$, γ$_6$, and γ$_7$ subunits are distinct from one another, with γ$_4$ and γ$_7$ being the most closely related and γ$_6$ having a somewhat more distant relation (see FIG. 9) (Chu, Robertson et al. 2001). However, the γ$_4$ subunit is a member of the TARP subgroup were γ$_7$ is not (Tomita, Chen et al. 2003). All three of these γ subunits are expressed concurrently in atrial myocytes.

It is unknown why multiple γ subunits are concurrently expressed in the same tissue, as this occurs not only in the heart but in the brain and other tissues as well. This co-expression in atrial myocytes is especially curious because there are no AMPA receptors expressed in myocytes. $\gamma_4$ and $\gamma_7$ may modulate other calcium channels expressed in atria besides Cav3.1 and Cav3.2. Both Cav1.2 and Cav2.3 are also expressed in atria. However, co-expression studies of $\gamma_4$ and $\gamma_7$ with these channels have not been done.

Here we characterize the structural differences between $\gamma_6$ and $\gamma_4$, which are responsible for their differential effects on Cav3 mediated calcium currents. We show through the use of a series of $\gamma_6/\gamma_4$ chimeras that the first of the four transmembrane spanning regions of $\gamma_6$ is both necessary and sufficient to confer Cav3 regulatory ability on the $\gamma_4$ subunit. Conversely, we also show that the insertion of the first transmembrane domain from $\gamma_4$ into $\gamma_6$ is sufficient to remove the Cav3 regulatory ability of this subunit. Using a mammalian 2-hybrid assay, we also show that the intracellular regions of the $\gamma_6$ subunit do not directly interact with the intracellular regions of the Cav3.1 channel, a result that is consistent with a transmembrane domain mediated regulatory function of $\gamma_6$ on Cav3.1.

Methods

Cell Culture—HEK-293 cells were maintained in Dulbecco's Minimum Essential Medium (DMEM) containing 4 mM L-glutamine, 4.5 g/L glucose and 1.5 g/L Na-bicarbonate (ATCC) supplemented with 10% fetal bovine serum (ATCC) and 100 U/mL:100 µg/mL:250 ng/mL of penicillin/streptomycin/amphotericin B (Life Technologies). HEK-293 cells stably transfected with Cav3.1 were a gift of Dr. L. Cribbs and Dr. E. Perez-Reyes and were maintained in media as above with the addition of 400 µg/mL G418 (Sigma). Cells were stored in a 5% CO2 incubator at 37° C. and passed every 7 days at a 1:5 dilution. Medium was changed every 3 days. For HEK-293/Cav3.1 experiments in which multiple aliquots of frozen cell stock were used, relevant results (in which variation between aliquots may have occurred) were normalized to controls from each aliquot.

Sub-Cloning of Vectors for Transfection in Functional and Localization Studies. For studies on the electrophysiological effects of independently transcribed γ subunits and chimeras in fluorescence-labeled cells, the coding regions of rat $\gamma_4$, $\gamma_{6L}$, and $\gamma_{6S}$, as well as those of all chimeric cDNAs (Chu, Robertson et al. 2001) were subcloned into pCR II vectors (InVitrogen) by TA cloning. The accession numbers of these previously described genes are as follows: rat $\gamma_4$ (AF361341), rat $\gamma_{6L}$ (AF361343), and rat $\gamma_{6S}$ (AF361344). The sequences of all chimeras created are shown schematically in FIG. 10 and in full length in FIG. 11.

From pCR II vectors, rat $\gamma_4$, $\gamma_{6L}$, $\gamma_{6S}$, and chimeric subunit cDNAs were then transferred to an expression vector (adCGI, or "adenovirus-CMV-GFP-IRES"), a gift of Dr. Jeffrey R. Holt containing a CMV-driven promoter, the coding region of GFP and an internal ribosomal entry site (IRES). Each target γ subunit cDNA was linked at an EcoRI site immediately after the IRES for independent expression of GFP and specific γ subunit proteins, insuring that cells expressing GFP also expressed γ subunits and that the secondary and/or tertiary structure of the γ subunits was not affected as might be the case with the creation of a GFP-γ fusion protein.

Transfection—HEK-293 cell lines stably transfected with Cav3.1 were transiently transfected with vectors containing γ subunit cDNAs using Lipofectamine 2000 reagent (Invitrogen) as per the manufacturer's recommendations. HEK-293 cells were grown to 70-80% confluence before transfection.

Electrophysiology—Whole-cell calcium currents were recorded using an Axopatch-1D patch clamp system and Clampex 8.0 software. Pipettes were fabricated from borosilicate glass and had typical resistances of 2-4 MΩ. The pipette solution contained (in mM): 130 NaCl, 10 EGTA, 2 MgCl$_2$, 1 CaCl$_2$, 10 HEPES, 3 Tris-ATP, and 0.3 Tris-GTP, adjusted to pH 7.4 with NaOH and 280 mOsm with sucrose. The bath solution contained (in mM): 137 NaCl, 1 KCl, 1 MgCl$_2$, 0.33 NaH$_2$PO$_4$, 2 CaCl$_2$, 10 HEPES, and 30 µM TTX, adjusted to pH 7.4 with NaOH and 280 mOsm with sucrose.

Recordings from HEK-293 cells were made 48-96 hours post-transfection, at which time expression, as measured by GFP fluorescence, peaked. All HEK-293 data is from current records in which pipette and whole-cell capacitance were about 100% compensated and series resistance was compensated to >80%. Series resistance values were typically <10 MΩ (megaohms), and no records were used in which the voltage error (as defined by $V_{er}=I_{max} \times R_a$) was greater than 5 mV. The holding potential of all protocols used for HEK-293 cells was −100 mV except for steady-state inactivation protocols where the holding potential was −120 mV. Current-voltage relationships for all HEK-293 cells were measured using 50 ms test depolarizations. Peak current amplitudes for activation curves were determined by fitting tail currents, elicited by stepping membrane voltage from varying test potentials to −60 mV, with the Boltzman equation. Test potential steps for activation protocols were of varied durations, corresponding to the time to peak of the elicited current. Inactivation curves were determined by fitting peak amplitudes of currents, observed in a test pulse to −20 mV, following 500 ms steps to varying potentials, with the Boltzman equation. Time to peak was determined using the current-voltage protocol described above. Inactivation time constants were determined by fitting the decay phase of currents to an exponential equation and deactivation time constants were determined by fitting the decay phase of tail currents to an exponential equation. Tail currents for Cav3.1 were found to be best fit by a double exponential equation. When a double exponential equation was used to fit Cav3.1 tail currents, the magnitude of the fast component was about 10 fold that of the slow component. Currents were recorded at 40 kHz and on-line filtered at 5. In some cases currents were off-line filtered at 1 kHz to further reduce noise. Current-voltage relationships and tail currents were recorded from HEK cells using an on-line P/−4 subtraction procedure. The average membrane capacitance of untransfected HEK-293 cells in pilot experiments was 12.5+/−0.4 pF (n=8).

Statistical Analysis—All data are reported as mean±SEM and tested for significance by one-way ANOVA. A value of P<0.05 was considered significant and when significant p-values were encountered groups were compared using the Tukey post-hoc test.

Mammalian 2-Hybrid Assay—The mammalian 2-hybrid assay utilizes elements from native transcription factors consisting of a DNA binding domain (DNA-BD), and a transcriptional activation domain (AD), which modulate expression of a target gene. Specifically, this system uses the GAL4 DNA-DB and VP-16 AD from yeast. Typically the DNA-BD and AD are part of a single protein which binds via the DNA-BD to specific regulatory sequences in a gene promoter and activates transcription. The mammalian 2-hybrid assay exploits the fact the DNA-BD and the AD can activate transcription as separate proteins so long as they are brought into close contact. To achieve this tethering of the DNA-BD and the AD, each domain is engineered to form a fusion protein with one of two target peptide sequences. If the resulting fusion proteins can physically interact when transfected into mammalian cells, the DNA-BD and AD will activate transcription of a reporter gene. The reporter in this instance is a plasmid that contains consensus GAL4 binding sites in its upstream promoter to modulate expression of chloramphenicol acetyl transferase (CAT). CAT is a readily quantifiable protein that can be measured to determine the strength of a resulting protein—protein interaction.

Because of the sensitivity of the reporter gene system, the mammalian 2-hybrid assay system is ideal for measuring weak or transient protein interactions. Moreover, fusion plasmids and the CAT reporter are transfected into mammalian cells, so the resulting proteins are perhaps more likely to adopt endogenous conformations and mimic interactions in vivo. Once interacting protein sequences are identified the mammalian 2-hybrid system can be used map out specific binding sites by mutational or deletional analyses.

To assess protein-protein interactions between cytoplasmic loop regions of Cav3.1 ($\alpha_{1G}$) and $\gamma_6$ we employed the Matchmaker mammalian 2-hybrid assay kit from Clontech (Palo Alto, Calif.) according to the manufacturer's protocol. Segments of Cav3.1 cDNA were subcloned into pVP16AD, which correspond to the following intracellular loops: N-terminus (nucleotides 1-240), 1-2 linker (nucleotides 1195-2229), 2-3 linker (nucleotides 2905-3762), 3-4 linker (nucleotides 4558-4734), and C-terminus (nucleotides 5467-6762). PCR primers were designed to amplify the loop regions and create restriction enzyme sites allowing the cDNA to be subcloned in frame with the VP16AD, thus generating a VP16-Cav3.1 fusion protein. Likewise, segments of $\gamma_6$ were ligated into pMGAL4 to create GAL4(DBD)-$\gamma_6$ fusion proteins of the following loop regions: N-terminus (nucleotides 1-120), 1-2 linker (nucleotides 178-423), 3-4 linker (nucleotides 568-659), and C-terminus (nucleotides 724-783). Since the 2-3 and 3-4 linkers comprise extra-cellular loops they were generated as negative controls. All plasmid constructs were confirmed by sequence analysis.

The 2-hybrid constructs were transfected into HEK-293 cells using $CaPO_4$ co-precipitation according to standard protocols. Cells were cultured in 10 cm dishes to a confluency of approx 70% prior to transfection. Ten micrograms of each pM-$\gamma_6$ and 10 ug of each pVP16-Cav3.1 were added to each plate along with 2 ug of pG5CAT reporter plasmid and 0.5 ug of the transfection efficiency control plasmid pCMV-beta-gal (Clontech). PMGAL4(DBD) and pVP16(AD) empty plasmids were transfected as negative controls for protein interaction. Moreover, the Clontech 2-hybrid control vectors pM53 and pVP16T were transfected separately and in combination as a positive control for protein interaction. Cells were harvested 48 hrs post transfection and assayed for beta-galactosidase activity and Chloramphenicol-acetyl-transferase (CAT) protein expression via the CAT ELISA assay (Roche). CAT expression was normalized to beta-gal activity and plotted as fold induction over the negative control sample.

Results

We identify specific regions of the $\gamma_6$ subunit that are necessary and sufficient for its inhibitory effect on LVA (Cav3.1) calcium current density. To accomplish this we have created a series of engineered $\gamma$ subunit proteins in which portions of $\gamma_6$ are either deleted or replaced by the homologous sequences from $\gamma_4$ and tested their ability to decrease calcium current in HEK/Cav3.1 cells. Since the $\gamma_4$ subunit does not decrease Cav3.1 calcium current, analysis of the effects of the engineered proteins should reveal critical sequences that are necessary and sufficient for the inhibitory effect of $\gamma_6$.

Effects of $\gamma$ Subunit Chimeras on Current through Heterologously Expressed Cav3.1 Channels. We have previously shown that co-expression of either the long or short isoform of the $\gamma_6$ subunit ($\gamma_{6L}$ and $\gamma_{6S}$) with the calcium channel $\alpha$ subunit Cav3.1 in HEK-293 cells causes a significant decrease in low voltage-activated current density (Hansen et al., 2004). For the three $\gamma$ subunits tested in that study, the effect was specific for the $\gamma_6$ isoforms as no inhibition is seen with either $\gamma_4$ or $\gamma_7$.

Since the $\gamma_6$s subunit had the same effect on Cav3.1 calcium current as $\gamma_6$L, the sequence deleted in this naturally occurring short isoform $\gamma_6$ can not be required for the inhibitory action of the $\gamma_6$ subunit. The $\gamma_6$s isoform is missing all of the second transmembrane domain and much of the third transmembrane domain of the full length protein. Therefore, the regions critical for the unique ability of $\gamma_6$ to decrease current density must be found in the N or C-terminal regions (or both) of the protein including the first and fourth transmembrane domains and associated cytoplasmic and extracellular regions. To confirm this, a chimeric subunit was engineered that combined the N- and C-terminal regions of $\gamma_6$ (including TM1 and TM4 and the associated cytoplasmic tails) with TM2 and TM3 from $\gamma_4$. This construct, $\gamma_{6446}$, was then transfected into Cav3.1/HEK cells and the calcium current density compared to controls. Current density in these cells was reduced significantly to 19+/−4% (n=10, p<0.01) of control values confirming that TM2 and TM3 are not necessary to confer the inhibitory effect of $\gamma_6$ as suggested by the ability of the short isoform, $\gamma_6$s, to decrease current.

Having confirmed that the critical portion of $\gamma_6$ must be contained in either the N- or C-terminal regions including TM1 and TM4, we designed a series of chimeric $\gamma$ proteins in which these areas were targeted for substitution or deletion.

FIG. 10 shows schematic diagram of chimeras in Panels A-K. Subunits $\gamma_{6L}$ and $\gamma_{6S}$ were previously shown to inhibit the expression of low voltage-activated current in HEK-293 cells stably expressing Cav3.1, where $\gamma_4$ had no effect on current in these cells. Chimeras were designed to either confer the inhibitory function of $\gamma_{6L}$ onto $\gamma_4$, to remove the inhibitory function of $\gamma_{6L}$, or to test the necessity of specific regions of these proteins for functional significance.

The first set of chimeras was designed to determine whether either the N-terminal or the C-terminal region of $\gamma_6$ was sufficient for current inhibition or whether both regions were required simultaneously. The chimera $\gamma_{6444}$ was engineered using wild type $\gamma_4$ but with the N-terminal region substituted by the homologous region of $\gamma_6$. The substituted region contained the N-terminal cytoplasmic domain, the first transmembrane domain (TM1) and a portion of the extracellular region linking TM1 to TM2. The second chimera in this series, $\gamma_{4446}$, was also based on wild type $\gamma_4$ but in this case TM4 and the C-terminal cytoplasmic domain from $\gamma_6$ were substituted into the protein.

When expressed in the Cav3.1/HEK cells, $\gamma_{6444}$ decreased normalized current density to 46+/−7.6% (n=12, p<0.05) of control values obtained from cells transfected with a blank vector. The magnitude of this effect is similar to that seen for wild type $\gamma_6$ as described above. In contrast, cells transfected with $\gamma_{4446}$ expressed calcium currents with densities similar to those obtained in controls (100+/−15%, n=7, p>0.05) as was the case with wild type $\gamma_4$. These results indicate that the N-terminal region of $\gamma_6$ is necessary and sufficient for the inhibition of calcium current.

To confirm this result and to rule out any effects of using the wild type $\gamma_4$ as the backbone for construction of the chimeras, we engineered proteins using wild type $\gamma_6$ to which the first and fourth transmembrane domains of $\gamma_4$ were substituted for the homologous regions of γ6 ($\gamma_{6664}$, $\gamma_{4666}$). In the case of the $\gamma_{6664}$ chimera, the construct contained the cytoplasmic C-terminal region as well as TM4 of γ4. The $\gamma_{4666}$ construct contained the N-terminal cytoplasmic region, TM1 and part of the extracellular region linking Tm1 and TM2 from γ6. Calcium current density in cells transfected with $\gamma_{4666}$ was not statistically different from controls (82+/−6%, n=9, P>0.05). In contrast, the calcium current density in cells transfected with $\gamma_{6664}$ were significantly reduced (37+/−5%, n=9, p<0.01). These results are consistent with our finding that the N-terminal region of γ6 contains a region critical for the inhibitory effect of this isoform on calcium current density.

To define more precisely what portion of the N-terminal region is responsible for this inhibitory effect, we engineered additional γ6 subunits that had portions of the N-terminal cytoplasmic domains removed. The construct $\gamma_{6L, N\text{-}trunc}$ had the first region of about 30 to about 32 amino acids deleted leaving a short cytoplasmic sequence (about 10 amino acids) before TM1. A similar construct, $\gamma_{6L, N\text{-}deleted}$ had the entire N-terminal cytoplasmic region up to TM1 deleted from the protein. Finally, $\gamma_{4.6666}$ had the N-terminal cytoplasmic domain of γ6 replace by the homologous region of γ4. Expression of all of these constructs significantly decreased calcium current. The magnitude of the effect was 52+/−5% for $\gamma_{6L, N\text{-}trunc}$ (n=8, p<0.05), 22+/−3% for $\gamma_{6L, N\text{-}deleted}$ (n=10, p<0.01 ) and 29+/−5% for $\gamma_{4.6666}$ (n=10, p<0.01). These results show that the N-terminal cytoplasmic region of γ6 is not necessary for the inhibitory effect of this isoform, since it can be removed or replaced with the homologous region of γ4 without diminishing the effect. By default these results suggest that the critical region of γ6 that is sufficient and necessary for its inhibitory effect on calcium current resides in TM1 (or a short sequence of the extracellular region that links TM1 and TM2).

FIG. 12 illustrates results of averaged normalized current densities of low voltage-activated current from HEK/Cav3.1 transfected with chimeric constructs. All of the chimeric constructs used, except $\gamma_{4446}$ and $\gamma_{4666}$, decreased current density in HEK/Cav3.1 cells. This demonstrates that the first transmembrane region of $\gamma_{6L}$ is both necessary and sufficient, when expressed within the context of a γ subunit, to confer an inhibitory function on the γ subunit protein with regard to low voltage-activated current.

To directly test the idea that TM1 of γ6 contains the sequence critical for its inhibitory effect on calcium current, two sets of expression plasmids were constructed that encoded TM1 of either γ4 or γ6. In one case, a bi-cistronic vector was used so that the γ subunit fragment and GFP were expressed as separate proteins. In the second case, TM1-GFP fusion proteins were encoded. Western analysis using a GFP antibody confirmed that the TM1-GFP fusion proteins were being expressed in the Cav3.1/HEK cells and that they localized to the plasma membrane.

For this experimental series, calcium current density in control cells transfected with a blank vector was −48.39+/−2.6 (n=45). The average calcium current in cells transfected with the full length γ6 subunit decreased 42% to −7.8+/−3.3 (n=18, p<0.05). When TM1 of γ6 was introduced into the cells, calcium current decreased 20% to −38.6+/−2.9 (n=35, p<0.05). Thus the first transmembrane domain of γ6 causes a significant decrease in calcium current, although the effect is somewhat less than that seen with the full length protein. In contrast, mean calcium current density in cells transfected with full length γ4 and with TM1 of γ4 was −56.3+/−5 (n=20, p>0.05) and −48.3+/−3 (n=16, p>0.05), respectively, confirming that the effect is specific for TM1 of the γ6 isoform. The ability of the TM1-fusion proteins to affect Cav3.1 calcium current was also determined with similar results. Average control currents were −46.9+/−5 (n=12). In cells transfected with the γ6 TM1-GFP fusion protein, average current fell to −32.9+/−6 (n=12) or a 30% decrease.

The normalized current-voltage relationships for low voltage-activated currents from HEK/Cav3.1 cells transfected with either vector, $\gamma_{6L}$, $\gamma_{6S}$, γ4, or the chimeras $\gamma_{6L\ N\text{-}trunc}$, $\gamma_{4\ C\text{-}trunc}$, $\gamma_{6444}$, $\gamma_{4666}$, $\gamma_{6664}$, $\gamma_{4446}$, $\gamma_{6446}$, $\gamma_{4.6666}$, and $\gamma_{6L\ N\text{-}del}$ are shown in FIG. 13. In FIG. 13, Panels A-I illustrate results of normalized current-voltage relationships from HEK/Cav3.1 cells expressing chimeras. Each panel shows I-V curves from vector control, native $\gamma_{6L}$, native $\gamma_4$, and a specific chimera. For the $\gamma_{6446}$ chimera, the I-V curve for the native $\gamma_{6S}$ protein is also shown as it has structural and functional similarities to $\gamma_{6446}$. Only the $\gamma_{4446}$ and $\gamma_{4666}$ chimeras (panels D and F) failed to significantly decrease normalized current density when expressed in HEK/Cav3.1 cells; the other chimeras decreased current density significantly from 48-81% compared to control levels with the vector alone. Additionally, none of the chimeras had any significant effect on the voltage at which peak current occurred compared to vector (vector V-peak=−29.5±0.9 mV, see Table 1).

TABLE 1

Effects of γ subunit chimeras on the biophysical properties of Cav3.1 dependent current in HEK-293 cells.

|  | Cav3.1 + adcgi | Cav3.1 + g6l | Cav3.1 + g6s | Cav3.1 + g4 |
|---|---|---|---|---|
| V peak (mV) Activation | −29.5 ± 0.9 (n = 10) | −31.1 ± 3.1 (n = 9) | −27.0 ± 2.5 (n = 5) | −30.6 ± 1.5 (n = 9) |
| V 0.5 (mV) | −32.3 ± 1.5 (n = 9) | −36.3 ± 6.2 (n = 4) | −36.3 ± 6.2 (n = 4) | −37.3 ± 0.9 (n = 8) |
| k | 13.3 ± 0.3 (n = 9) | 12.7 ± 1.5 (n = 4) | 12.7 ± 1.5 (n = 4) | 11.8 ± 0.5 (n = 8) |
| time to peak @ −20 mV (ms) Inactivation | 5.7 ± 0.4 (n = 10) | 6.0 ± 0.8 (n = 5) | 6.4 ± 0.5 (n = 3) | 5.2 ± 0.5 (n = 9) |
| V 0.5 (mV) | −71.9 ± 1.4 (n = 8) | −78.5 ± 2.6 (n = 6) | −72.0 ± 5.9 (n = 3) | −79.2 ± 1.5 (n = 7) |
| k | 5.4 ± 0.1 (n = 8) | 5.4 ± 0.3 (n = 6) | 5.9 ± 0.7 (n = 3) | 6.1 ± 0.2 (n = 7) |
| tau @−20 mV (ms) | 19.8 ± 1.3 (n = 8) | 18.6 ± 1.1 (n = 6) | 22.9 ± 0.7 (n = 2) | 15.8 ± 0.7 (n = 7) |
| Deactivation tau @ −100 mV (ms) | 1.19 ± 0.19 (n = 9) | 1.54 ± 0.48 (n = 4) | 1.20 ± 0.06 (n = 3) | 1.84 ± 0.28 (n = 8) |

TABLE 1-continued

Effects of γ subunit chimeras on the biophysical properties of Cav3.1 dependent current in HEK-293 cells.

|  | Cav3.1 + g6l n-trunc | Cav3.1 + g4 c-trunc | Cav3.1 + g6444 | Cav3.1 + g4666 | Cav3.1 + g6664 |
|---|---|---|---|---|---|
| V peak (mV) Activation | −31.6 ± 1.9 (n = 10) | −28.6 ± 1.8 (n = 7) | −29.5 ± 0.8 (n = 11) | −26.6 ± 3.1 (n = 6) | −31.9 ± 2.3 (n = 8) |
| V 0.5 (mV) | −28.3 ± 5.0 (n = 8) | −32.6 ± 1.3 (n = 8) | −33.2 ± 0.8 (n = 11) | −38.0 ± 3.3 (n = 3) | −32.9 ± 1.4 (n = 6) |
| k | 13.1 ± 0.8 (n = 8) | 12.1 ± 0.8 (n = 8) | 12.4 ± 0.4 (n = 11) | 12.0 ± 0.8 (n = 3) | 12.4 ± 0.7 (n = 6) |
| time to peak @ −20 mV (ms) Inactivation | 6.3 ± 0.5 (n = 9) | 6.3 ± 0.7 (n = 7) | 4.9 ± 0.3 (n = 11) | 17.0 ± 5.9 (n = 6) | 14.4 ± 4.7 (n = 8) |
| V 0.5 (mV) | −74.0 ± 2.2 (n = 5) | −71.5 ± 0.7 (n = 8) | −74.1 ± 0.5 (n = 9) | −72.1 ± 1.9 (n = 3) | −73.0 ± 1.7 (n = 6) |
| k | 5.6 ± 0.1 (n = 5) | 5.5 ± 0.1 (n = 8) | 5.2 ± 0.1 (n = 9) | 5.8 ± 0.3 (n = 3) | 6.3 ± 0.3 (n = 6) |
| tau @−20 mV (ms) Deactivation tau @ −100 mV (ms) | 19.4 ± 1.1 (n = 5) | 19.2 ± 1.3 (n = 8) | 16.5 ± 1.1 (n = 9) | 23.3 ± 1.1 (n = 3) | 24.9 ± 1.9 (n = 6) |
| Fast | 1.41 ± 0.18 (n = 7) | 1.22 ± 0.13 (n = 8) | 1.18 ± 0.10 (n = 11) | 1.47 ± 0.48 (n = 4) | 1.38 ± 0.26 (n = 7) |

|  | Cav3.1 + g4446 | Cav3.1 + g6446 | Cav3.1 + g4.6666 | Cav3.1 + g6 n-del |
|---|---|---|---|---|
| V peak (mV) Activation | −30.0 ± 1.64 (n = 8) | −31.3 ± 1.3 (n = 8) | −31.4 ± 1.8 (n = 7) | −31.1 ± 2.7 (n = 9) |
| V 0.5 (mV) | −30.8 ± 3.3 (n = 9) | −36.0 ± 1.1 (n = 8) | −33.2 ± 2.0 (n = 6) | −26.2 ± 2.5 (n = 9) |
| k | 11.2 ± 0.7 (n = 9) | 10.8 ± 0.6 (n = 8) | 14.9 ± 1.6 (n = 6) | 15.0 ± 1.7 (n = 9) |
| time to peak @ −20 mV (ms) Inactivation | 8.0 ± 1.1 (n = 8) | 7.6 ± 2.0 (n = 10) | 6.7 ± 0.9 (n = 7) | 12.1 ± 2.4 (n = 9) |
| V 0.5 (mV) | −67.0 ± 2.3 (n = 8) | −75.3 ± 1.2 (n = 8) | −78.1 ± 1.2 (n = 6) | −70.2 ± 0.4 (n = 9) |
| k | 5.9 ± 0.5 (n = 8) | 4.4 ± 0.3 (n = 8) | 5.8 ± 0.2 (n = 6) | 5.0 ± 0.2 (n = 9) |
| tau @−20 mV (ms) Deactivation tau @ −100 mV (ms) | 22.8 ± 3.0 (n = 6) | 16.4 ± 0.9 (n = 8) | 19.0 ± 1.5 (n = 6) | 25.4 ± 1.0 (n = 9) |
| Fast | 1.69 ± 0.32 (n = 7) | 1.20 ± 0.15 (n = 8) | 1.39 ± 0.19 (n = 7) | 1.24 ± 0.14 (n = 9) |

As reflected in the Table 1 results for γ subunit chimeras, there are no significant differences in the voltage at peak current, voltage dependency, or kinetic parameters between cells transiently transfected with vector as compared to cells transfected with $\gamma_{6L}$, $\gamma_{6S}$, $\gamma_4$ or any of the chimeras studied, with the exception of the τ (tau) of inactivation and k of activation from cells expressing $\gamma_{6L}$ N-del.

The voltage dependency of activation for low voltage-activated current from HEK/Cav3.1 cells transfected with either vector, $\gamma_{6L}$, $\gamma_{6S}$, $\gamma_4$, or the chimeras $\gamma_{6L\ N\text{-}trunc}$, $\gamma_{4\ C\text{-}trunc}$, $\gamma_{6444}$, $\gamma_{4666}$, $\gamma_{6664}$, $\gamma_{4446}$, $\gamma_{6446}$, $\gamma_{4.6666}$, and $\gamma_{6L\ N\text{-}del}$ is shown in FIG. 14 (see FIG. 14, Table 1). Only the Boltzman fits to voltage dependency of non-isochronic activation curves are shown for ease of interpretation. The V0/5 and k values of activation curves are shown in Table 1. None of the transfected γ subunits or chimeras had a significant effect on the V0.5 or the k of the voltage dependency of activation curves compared to vector control, except for $\gamma_{6L}$ N-del which shifted the k of activation from a control value of 13.3±0.3 to 15.0±1.7 (p>0.05).

FIG. 15 shows the voltage dependency of inactivation for low voltage-activated current from HEK/Cav3.1 cells transfected with either vector, $\gamma_{6L}$, $\gamma_{6S}$, $\gamma_4$, or the chimeras $\gamma_{6L\ N\text{-}trunc}$, $\gamma_{4\ C\text{-}trunc}$, $\gamma_{6444}$, $\gamma_{4666}$, $\gamma_{6664}$, $\gamma_{4446}$, $\gamma_{6446}$, $\gamma_{4.6666}$, and $\gamma_{6L\ N\text{-}del}$. Boltzman fits to voltage dependency of inactivation curves only are shown. The V0.5 and k values of inactivation curves are reported in Table 1. There were no significant differences in either the V0.5 or k values for the inactivation curves for $\gamma_{6L}$, $\gamma_4$, or any of the chimeras compared to vector.

FIG. 16 illustrates voltage dependency of time to peak current of low voltage-activated current from HEK/Cav3.1 cells expressing chimeric constructs. Spline curves connecting data points only are shown. Specific data points along with standard error bars are not shown for ease of interpretation. The times to peak current values at −20 mV, approximately where peak current occurred, are reported in Table 1. There were no significant differences in the times to peak current at −20 mV for $\gamma_{6L}$, $\gamma_4$, or any of the chimeras compared to vector.

FIG. 17 illustrates results of voltage dependency of the time constant, τ (tau), of inactivation of low voltage-activated current from HEK/Cav3.1 cells expressing chimeric constructs. Spline curves connecting data points only are shown. The time constant of inactivation values at −20 mV, approximately where peak current occurred, are reported in Table 1. There were no significant differences in the time constant of inactivation at −20 mV for $\gamma_{6L}$ or $\gamma_4$ compared to vector. There were also no significant differences in the time constant of inactivation at −20 mV between vector and any of the chimeras. However, there was considerable variability in the inactivation τ among the chimeras. Given that there were no differences between the native subunits from which the chimeras were derived and vector, the effects of the chimeras on the τ of inactivation may be a consequence of a non-native protein interacting with the channel.

FIG. 18 illustrates results of voltage dependency of the fast component of the time constant (τ) of deactivation for low voltage-activated current from HEK/Cav3.1 cells expressing chimeric constructs. Spline curves connecting data points only are shown. The time constant of deactivation values at −100 mV are reported in Table 1. There were no significant differences in the fast τ (tau) of deactivation at −100 mV for $\gamma_{6L}$, $\gamma_4$, or any of the chimeras compared to vector. The slow component of the time constant of deactivation accounted for <10% of the deactivation parameter, and did not exhibit voltage dependency. We did not report the slow τ of deactivation here because of its relatively minor functional importance.

In summary, there were no significant differences in the time to peak (see FIG. 16, Table 1), the time constant of inactivation (see FIG. 17, Table 1), or the fast component of the time constant of deactivation (see FIG. 18, Table 1) between vector, $\gamma_{6L}$, $\gamma_{6S}$, $\gamma_4$, or the chimeras $\gamma_{6L\ N\text{-}trunc}$, $\gamma_{4\ C\text{-}trunc}$, $\gamma_{6444}$, $\gamma_{4666}$, $\gamma_{6664}$, $\gamma_{4446}$, $\gamma_{6446}$, $\gamma_{4.6666}$, and $\gamma_{6L\ N\text{-}del}$. Although there appears to be considerable variability for the time constant of inactivation curve among the γ subunit chimeras, the variability occurs around the vector values and is not skewed either positively or negatively, and was not significant. Tail currents from HEK/Cav3.1 cells were best fit with a double exponential equation. We have only shown the fast component of the time constant of deactivation here, because its magnitude was about 10 fold greater than that of the slow component. Also, the slow component did not exhibit voltage dependency, and was not significantly affected by any of the chimeras.

Mammalian 2-hybrid assay for $\gamma_{6L}$ Cav3. 1 interaction domains. To determine whether the $\gamma_{6L}$ subunit interacts directly with Cav3.1 to inhibit expression of current through this channel, we used a mammalian 2-hybrid assay. The results of this assay are shown in FIG. 19.

FIG. 19 illustrates results of the mammalian 2-hybrid assay for interaction of Cav3.1 and $\gamma_{6L}$. Fold induction in chloramphenicol-acetyl-transferase (CAT) in transfected HEK-293 parental cells (not expressing Cav3.1) is shown. Negative control transfections of non-fusion pMGAL4 (DBD)+non-fusion pVP16 (AD), non-fusion pMGAL4 (DBD)+pVP16T (positive control AD; binds to pM53), and pMGAL4 (DBD) fused to pM53 (known to bind product of pVP16T)+non-fusion pVP16 (AD) do not induce transcription of CAT. About 130 fold induction in CAT is seen with positive control transfection of pMGAL4 (DBD) fused to pM53 (known to bind product of pVP16T)+pVP16T (fusion of AD to product known to bind pM53). Further transfections of pMGAL-4 fused to either the N-terminal of $\gamma_{6L}$ (6N) or the C-terminal of $\gamma_{6L}$ (6C) along with the specified intracellular regions of Cav3.1 fused to pVP16 did not induce transcription of CAT. No interaction between either the N-terminal or C-terminal regions of $\gamma_{6L}$ with any of the major intracellular regions of Cav3.1 was seen (courtesy of Karen Weis).

The major limitation of using a 2-hybrid assay to detect the interaction of membrane bound proteins is that in order for the assay to induce transcription in the nucleus, the two interacting proteins the fragments of the proteins expressed must be soluble. We therefore used the N- and C-terminal domains of $\gamma_{6L}$, which are by far the longest intracellular regions in the native protein, and the N- and C-terminal regions of Cav3.1, which again are intracellular in the native protein. We also used the I-II, II-III, and III-IV intracellular linker regions from Cav3.1 as these are long cytoplasmic domains in the native protein. The positive control from the 2-hybrid assay shows approximately 130 fold induction in CAT expression, with no induction from the negative controls. However, there were no interactions detected between any of the regions of $\gamma_{6L}$ and Cav3.1 studied. This result is consistent with the finding that the first transmembrane domain of $\gamma_{6L}$ is responsible for the modulation of Cav3.1 current. This result could also be explained if there is no direct interaction between $\gamma_{6L}$ and Cav3.1 (i.e. the $\gamma_{6L}$ effect is mediated by another protein).

Additionally, the site of interaction could be extracellular, although this seems unlikely given the small size of the $\gamma_{6L}$ extracellular regions.

Discussion

Our results provide the first description of the domain structures, which mediate the effects of γ subunits on Cav3 channels, and demonstrate that the N-terminal transmembrane domain of γ subunits plays a critical role in their modulation of Cav3 channels. The subunit $\gamma_{6L}$, but not $\gamma_4$ has previously been shown to inhibit current expression through Cav3.1 channels expressed in HEK-293 cells. Through the use of a series of $\gamma_6/\gamma_4$ chimeras, we showed that the inhibitory function of $\gamma_6$ on current through Cav3.1 channels could be conferred upon $\gamma_4$ by splicing the N-terminal region up to and including transmembrane domain (TM1) only of $\gamma_6$ into $\gamma_4$. Conversely, we showed that the inhibitory function of $\gamma_6$ could be removed by splicing only the N-terminal domain including TM1 from $\gamma_4$ into $\gamma_6$. Additionally, the removal of the cytoplasmic N-terminal region up to but not including TM1 from $\gamma_6$ had no effect on its function, nor did the substitution of the N-terminal cytoplasmic region of $\gamma_4$ to $\gamma_6$ have a functional effect. Furthermore, substitution of TM2 and TM3 from $\gamma_4$ to $\gamma_6$ did not affect the function of $\gamma_6$ and the substitution of TM4 from $\gamma_4$ to $\gamma_6$ also had no effect on $\gamma_6$. The inhibitory effect Of $\gamma_6$ could not be conferred onto $\gamma_6$ by substituting TM4 from $\gamma_6$ into $\gamma_4$. None of the chimeras tested significantly altered the voltage dependency or kinetics of the Cav3.1 channels when co-expressed with the exception of the $\gamma_6$ N-terminal deletion chimera, which significantly flattened the activation curve of Cav3.1.

Although we have clearly shown that chimeras containing the TM1 from $\gamma_6$ have an inhibitory effect on Cav3.1, it is unclear whether the TM1 of $\gamma_6$ interacts directly with Cav3.1. There may be a direct interaction; however, this has not been explicitly tested in our study. In assessing this prospect, antibodies are made to $\gamma_6$ and Cav3.1 for use in co-immunoprecipitation experiments to determine whether these two subunits directly interact.

Given that the inhibitory effect of $\gamma_{6L}$ on Cav3 channels appears to be mediated by the first transmembrane region, we looked closely at the sequence differences between $\gamma_{6L}$, $\gamma_4$, $\gamma_7$, and $\gamma_1$ ($\gamma_1$ is homologous to $\gamma_6$ and can also inhibit calcium current, and $\gamma_7$ has no effect on Cav3.1 current density in HEK/Cav3.1 cells).

FIG. 20 shows a TM1 sequence alignment of amino acids for all 8 of the γ subunits grouped by phylogeny. Subunits $\gamma_6$ and $\gamma_1$ show considerable divergence from the TARP subgroup and $\gamma_7$ and $\gamma_5$. In FIG. 21 the TM1 amino acids from $\gamma_{6L}$, $\gamma_4$, $\gamma_7$, and $\gamma_1$ are shown by group to demonstrate which of the many substitutions in $\gamma_{6L}$ compared to $\gamma_4$ and $\gamma_7$ are conserved. The most obvious discrepancy (or least conserved region of TM1 between $\gamma_6$ and $\gamma_1$ versus $\gamma_4$ and $\gamma_7$) is seen in position 4 of TM1 where a non-polar amino acid is substituted for an uncharged polar amino acid (L→T/S for $\gamma_{6L}$, $\gamma_4$, and $\gamma_7$ respectively).

Although there is a substitution at position 3 from a glycine (non-polar) in $\gamma_6$ to a threonine/serine (uncharged polar) in $\gamma_4$ and $\gamma_7$ respectively, $\gamma_1$ has a threonine (uncharged polar) at this position. Since $\gamma_1$ is relatively closely related to $\gamma_6$ and has been shown to have strong calcium channel regulatory ability, our initial assessment was that it seemed unlikely that position 3 (and the noted substitution) should be of functional consequence.

The other amino acids in TM1 are generally conserved within their group among $\gamma_6$, $\gamma_4$, and $\gamma_7$ and are non-polar. Although the substitution of a single amino acid may seem like a relatively small change to drastically alter the function of a protein, there have been examples in the past of single amino acid substitutions having profound functional consequences on ion channels (Li, Gamper et al. 2004; Njue, Hayashi et al. 2004; Wagner, Czajkowski et al. 2004). The amino acid substitutions in these studies were not in the selectivity filter region (where substitutions can in some cases cause dramatic functional changes) and did not generate premature stop codons. As a next step in determining whether these two amino acids modulate the inhibitory effects of $\gamma_6$, our laboratory is performing mutational analysis at this position followed by patch clamp recording to determine whether a mutation affects $\gamma_6$ function.

One result of this study which was particularly unexpected, and which did not coincide with the rest of the results obtained, was that the C-truncated $\gamma_4$ construct reduced current in HEK/Cav3.1 cells (see FIG. 12; however, see also FIG. 38 and statements further below). In none of our previous studies on Cav3.1 and Cav3.2 in HEK cells or in HL-1 cells has $\gamma_4$ reduced current expression. Why this would be the case in this study is unknown. The region of $\gamma_4$ which was removed in this construct contains a PDZ binding domain at the extreme C-terminal end of the protein. We have considered that the removal of this region may release the $\gamma_4$ protein from binding some other target in the cell ($\gamma_4$ is a TARP) and allow the remaining sequence to act as a calcium channel modulator. This explanation seems implausible, however, because $\gamma_{4446}$ (which also has the C-terminal PDZ binding domain removed) had no effect on current. In the C-terminal truncated $\gamma_4$ construct tested, the entire C-terminal region, over 100 amino acids long, was removed. In order to better understand whether it is removal of the PDZ binding domain specifically that is responsible for the effect of $\gamma_4$ C-trunc, our laboratory is generating a chimera that has only the 4 amino acid PDZ binding domain removed from $\gamma_4$. This construct will then be tested in HEK/Cav3.1 cells to determine whether it has the same effect as the $\gamma_4$ C-truncated construct described here.

As a follow-up to the results observed with the $\gamma_4$ C-truncated construct, further efforts led to results in FIG. 38 (discussed in Example 6 herein) which contradicted the results shown in FIG. 12. It is presently believed that the results in FIG. 38 are accurate, where the subject construct is not able to mediate a reduction of current.

In conclusion, we have shown for the first time that the inhibitory effects of the $\gamma_6$ subunit are dependent upon its first transmembrane domain. We have shown that this transmembrane domain is both necessary and sufficient to confer low voltage-activated calcium channel modulatory ability on members of the $\gamma$ subunit family, including a member of the TARP subgroup whose functions include modulation of AMPA receptor targeting. Isolating the domain of the $\gamma$ subunit that is responsible for calcium channel regulatory function may serve to distinguish the TARPs from the rest of the $\gamma$ subunit family. This finding is of important consequence as $\gamma$ subunits are potential targets for interventions seeking to modulate calcium current in a variety of tissues.

EXAMPLE 3

Analysis of $\gamma 6$ Structure and Function: Role of TM1, GxxxA Motifs and Glycine Residues Brief Description of Figures for Example 3

FIG. 22 illustrates a comparison of the three-dimensional structure of the first transmembrane domain of $\gamma 6$ and $\gamma 4$. Glycine, alanine, leucine, polar residue, charged residue and others are shown in blue (B), ice blue (IB), red (R), yellow (Y), green (G), and pink (P), respectively. The glycine and alanine residues on $\gamma 6$ subunit produce a long groove on one side of the helix (colored blue and ice blue, respectively). This figure was made using VMD. Instead of correspondingly yellow text, the sequence alignment lists one letter amino acids in black and underlined.

FIG. 23 illustrates a comparison of three-dimensional structures of wild type of the first transmembrane domain of $\gamma 6$ subunits with mutants with mutants G42L and G49L. Glycine, alanine, leucine, polar residue, charged residue and others are shown in blue, ice blue, red, yellow, green and pink, respectively. The mutant G42L can effectively remove the first GxxxA motif, and the mutant G49L can effectively remove the second GxxxA motif. This figure was made using VMD. Instead of correspondingly yellow text, the sequence alignment lists one letter amino acids in black and underlined.

FIG. 24 illustrates a comparison of three-dimensional structures of wild type of the first transmembrane domain of $\gamma 4$ subunits with mutants L23G. Glycine, alanine, leucine, polar residue, and others are shown in blue, ice blue, red, yellow, and pink, respectively. The replacement of leucine with glycine produces a long groove on one face of helix (colored blue and ice blue). This figure was made using VMD. Instead of correspondingly yellow text, the sequence alignment lists one letter amino acids in black and underlined.

FIG. 25 illustrates results of electrophysiology experiments. The $\gamma 6$ subunit and its first transmembrane domain decreases Cav3.1 dependent calcium currents in Cav3.1-HEK cells. A, representative whole-cell current traces for an individual Cav3.1-HEK cell stably transfected with Cav3.1 in response to voltage steps from holding potential from −100 mV to +55 mV in 5 mV interval. B, averages of normalized current voltage relationship from Cav3.1-HEK cells transiently transfected with a bicistronic vector (adCGI) expressing either GFP, GFP plus $\gamma 6$, and GFP plus $\gamma 6$ first transmembrane domain only. C, averages of normalized peak current density of Cav3.1-HEK cell transiently transfected with empty vector (adcGI), GFP plus $\gamma 6$, GFP plus $\gamma 4$, GFP plus $\gamma 6$ first transmembrane domain, and GFP plus $\gamma 4$ first transmembrane domain. Only $\gamma 6$ and its transmembrane domain significantly decreased Cav3.1 calcium current density. The $\gamma 6$ significantly decreased the current density by 42%, and its first transmembrane domain was 20%.

FIG. 26 illustrates results for voltage dependency of activation and inactivation of Cav3.1 coexpressed with $\gamma$ subunits and chimeras. Activation and inactivation curves for currents recorded in Cav3.1-HEK cells co-expressing with one $\gamma$ subunits, $\gamma 4$ or $\gamma 6$, or their first transmembrane domain only. No significant differences were seen for all these co-expression for either the V½ or K value of both activation and inactivation when compared to control vector.

FIG. 27 illustrates results for kinetics properties of Cav3.1 co-expressed with $\gamma 4$, $\gamma 6$ or their first transmembrane domain. A, Time to peak, B, Time constant for inactivation, C, Time constant for deactivation. No significant differences were found among these $\gamma$ subunits and chimeras.

Table 3.2: Effects of $\gamma 4$, $\gamma 6$, $\gamma 4$(TM1); first transmembrane domain), and $\gamma 6$ (TM1) on the biophysical properties of Cav3.1 dependent current in Cav3.1-HEK cells. There are no significant differences in the voltage at peak current, voltage dependency, or kinetic parameters between cells transiently transfected with vector as compared to cells transfected with $\gamma 4$ subunit and the first transmembrane domain of $\gamma 4$. However, cells transfected with $\gamma 6$ subunit slightly shifted the peak voltage by 4.5 mV in the positive direction, with the first transmembrane domain of γ6 by 3 mV; both are statistically significant.

FIG. 28 illustrates a Western blot experiment. The results indicated that these GFP tagged first transmembrane domains were located in cell membrane. GFP fusion proteins contain GFP and the first transmembrane domain from γ6 and γ4. The band "a" is GFP fusion protein, and band "b" is GFP protein (courtesy of Janice Jones).

FIG. 29 illustrates averages of current density of Cav3.1-HEK cell transiently transfected with either empty vector (adcGI), γ6 TM1 and fusion GFP- γ6 TM1. The γ6 TM1 and fusion GFP-γ6 TM1 decreased Cav3.1 calcium current density.

FIG. 30 averages of normalized peak current density of Cav3.1-HEK cell transiently transfected with either empty vector (adcgi), GFP plus γ6, GFP plus γ4, GFP plus γ6 and γ4 mutants. Only the G42L mutant of γ6 removes its inhibitory function.

Table 3.3 Normalized current density of gamma subunits (γ6, γ4, and variants).

Abstract

We have demonstrated that the γ6, but not γ4 or γ7 subunits decreased LVA (Cav3.1 and Cav3.2) and HVA (Cav2.3) calcium current densities in heterologous expression systems. However, the amino acid sequences within γ6 that are critical for its unique modulatory function are not known. All γ subunits have a similar structure consisting of four helical transmembrane domains (TM) and intracellular C- and N-terminals, although there are significant differences in amino acid composition. We used chimeric proteins, engineered by systematically swapping sequences between γ6 and γ4, to identify critical peptide domains of γ6 subunits involved in modulation of voltage dependent calcium currents. The results showed that the N-terminal transmembrane domain was necessary for the γ6 subunit inhibitory effect.

We subsequently constructed plasmids to contain only the first transmembrane domains (TM1) of γ6 or γ4 subunit, to further demonstrate that the TM1 of γ6 subunit is both necessary and sufficient to inhibit calcium current, though at an impaired level. The TM1 of γ6 subunit significantly inhibits the expression of Cav3.1 current by 20%, while the γ4 subunit and its TM1 have no effect on Cav3.1 calcium current.

The γ6 subunit has a unique predicted structural feature in its TM1. Two adjacent GxxxA motifs are predicted to produce a long groove on one side of the helix due to the short side chains of the glycine and alanine residues. This feature is not present in the other γ subunits. Therefore we performed site directed mutagenesis of several specific residues in TM1 to determine which residues are critical for the inhibitory function of the γ6 subunit. We identified two adjacent GxxxA motifs ($G^{42}$xxx$A^{46}$xx$G^{49}$xxx$A^{53}$) within γ6 TM1. We predict that these structural motifs can produce a long groove on one face of the transmembrane helix, at least partly due to the short side chains of the glycine and alanine residues. The motifs can be implicated in the mechanism of promoting and stabilizing helix-helix interactions. We performed site directed mutagenesis of specific residues in TM1, for example replacing the G and A residues with amino acids containing large side chains. Our results show that the G42L and A461 mutants are no longer inhibitory while the G49L mutant retained the inhibitory function of the wild type. Stated differently, substituting glycine with leucine at position 42 (G42L), but not at the position 49 (G49L), completely removes the γ6 subunit's inhibitory function.

Our results suggest that structurally, the first GxxxA motif and the surrounding region are able to impact the γ6 function.

Introduction

Voltage-dependent calcium channels are multi-subunit protein complexes. They are composed of four subunits, including a pore forming α1 subunit, and auxiliary β, α2δ, γ subunits. To date, ten α1 subunits, four β subunits, four α2δ subunit and eight γ subunits have been identified. It has been shown that expression of the α1 subunit alone can produce functional calcium channels although the resultant currents are not always identical to native calcium currents. However in most cases native calcium channels are complexes of a α1 subunit with one or more auxiliary subunits. Coexpression studies have further verified that addition of auxiliary subunits can have significant effects on channel trafficking or on channel biophysical properties (see Arikkath and Campbell 2003 for review) making them more like those seen in native cells.

Besides characterizing the role of accessory subunits in modifying calcium channel function, it is also important to identify critical sequences underlying subunit interaction. Most of the previous work in this area has focused on the β and α2δ subunits; much less is known about the function of γ subunits. Extensive experimental work has been done on the α1-β interaction. The β subunit interaction domain (BID) is a sequence of 41 amino acids, found in all β subunits (De Waard, Pragnell et al. 1994). In the α1 subunits, there is a corresponding α interaction domain (AID) located in the intracellular linker of the first and second transmembrane domains (Pragnell, De Waard et al. 1994). It is thought that the β subunit associates with the α1 subunit directly through AID/BID interaction. Recently, the crystal structure of this binding complex was reported (Van Petegem, Clark et al. 2004). Mutations at critical amino acids in the AID can severely reduce the ability of β to bind to α1, and further hinder the protein trafficking to the membrane. The β subunits can form heterogeneous complexes with α1 subunits both in vivo and in vitro (Scott, De Waard et al. 1996; Pichler, Cassidy et al. 1997). However, the affinity of interaction is isoform specific, so that each channel associates with a specific β subunit.

The α2δ subunit is composed of two separate proteins that are transcribed by a single gene, cleaved and rejoined by a disulfide bond (De Jongh, Warner et al. 1991). The δ subunit is a single alpha-helix that passes through the membrane once and acts as an anchor for the α2 subunit, which sits extracellularly. The α2 subunit interacts with the α1 subunits through its repeat III loop (Gurnett, Felix et al. 1997).

While it is generally known that γ subunits have inhibitory effects on calcium channels, the functional domains of γ subunits are unclear. Using a phylogenetic analysis it is possible to organize the eight γ subunits into three subgroups (Chu, Robertson et al. 2001). One subgroup consists of the γ2, γ3, γ4, and γ8 isoforms. Members of this group are also called TARP's, transmembrane a-amino-3-hydroxyl-5-methyl-4-isoxazolepropionate (AMPA) receptor regulatory proteins, because they contain a C-terminal PSD-95/DGL/ZO-1 (PDF) binding motif (T-T-P-V), which is essential for the targeting of AMPA receptors to the membrane (Tomita, Chen et al. 2003). The remaining four γ subunits form two subgroups. The first includes γ5 and γ7, which have a C-terminal motif similar to that of the TARPS (T/S-S-P-C). The second group contains γ1 and γ6, which have a truncated C-terminal region. Given the diversity of structure within the γ subunit family, it is difficult to predict what region might act as an interaction domain.

The γ1 subunit was initially identified as a component of the skeletal muscle voltage dependent calcium channel complex (Curtis and Catterall 1984). The specific region of γ1 subunit necessary for the association with the α1 subunit has not been identified. However, Arikkath et al recently reported that the first half of the γ1 subunit is necessary for its function with the Cav1.1 channel using γ1/γ2 chimeras, which swapped the first half and second half between γ1 and γ2 (Arikkath, Chen et al. 2003). The wide type γ1 subunit but not the γ2 subunit, has an inhibitory effect on the Cav 1.1 calcium current (Freise, Held et al. 2000; Arikkath and Campbell 2003). Arikkath demonstrated that the chimera containing the first half of γ1 and the second half of γ2 could restore γ1 inhibitory function in γ1 null mouse myotubes, while the chimera containing the first half of γ2 and the second half γ1 did not have the functional effect of γ1 (Arikkath, Chen et al. 2003).

The γ6 subunit, but not the γ4 subunit, decreased calcium current density mediated by Cav3.1 in HEK cells. We designed chimeric proteins consisting of portions from γ4 and γ6 to screen for sequences required for γ6 modulation of Cav3.1 channels. The γ6 subunit consists of two isoforms, long and short. The short isoform is missing the second and third transmembrane domains. However, both γ6 isoforms have similar inhibitory effects on Cav3.1 indicating that the second and third transmembrane domains are not required for its action. A series of γ4/γ6 chimeras were constructed by shortening the terminals and swapping the first or fourth domains between γ4 and γ6 subunits.

of γ6 is necessary for its function, since the inhibitory effect only existed when first transmembrane domain of γ6 subunit was part of the chimera.

Herein, we demonstrate that just the first transmembrane domain of γ6 is sufficient for γ6's inhibitory function. Those findings allowed us to investigate further in an attempt to identify critical sequences, motifs, or residues in this region of the protein with mutational analysis. The first transmembrane domains of γ subunits are fairly short being 20 amino acids in length. As shown in Table 3.1, there is a reasonably high homology among all the γ subunits in the first transmembrane domain. However a careful comparison of the first transmembrane domain of γ6 and that of the other isoforms reveals several possible targets for mutation. The most obvious discrepancy is at position 4 of the first transmembrane domains, where both γ6 and γ1 have a leucine residue (position 43 of full length γ6, Leu43; and position 13 of full length γ1, Leu13), a nonpolar amino acid, but all the other γ subunits contain a threonine/serine, an uncharged polar amino acid. There are reports that single amino acid substitutions have functional consequence as they could be essential for subunit binding and channel conductance (De Waard, Scott et al. 1996; Bahinski, Yatani et al. 1997). The mutations of a nonpolar residue to a polar one have been linked with lost function and leading to disease (Curran and Engelman 2003). Therefore we generated site-specific mutations targeting this residue to determine if this leucine residue, or the difference between a non-polar and polar residue is critical for the γ6 subunit function.

TABLE 3.1

The alignment of first transmembrane domains of all gamma subunits.

| | 1 | 2 | 3 | 4 | 5 | 6 | 7 | 8 | 9 | 10 | 11 | 12 | 13 | 14 | 15 | 16 | 17 | 18 | 19 | 20 | (SEQ ID NO:) |
|---|---|---|---|---|---|---|---|---|---|---|---|---|---|---|---|---|---|---|---|---|---|
| | 40 | 41 | 42 | 43 | 44 | 45 | 46 | 47 | 48 | 49 | 50 | 51 | 52 | 53 | 54 | 55 | 56 | 57 | 58 | 59 | |
| γ6 | K | L | G | L | L | V | A | I | V | G | A | T | L | A | V | L | A | V | G | T | 12 |
| γ1 | R | V | T | L | F | F | I | L | A | G | G | T | L | A | M | V | A | V | V | T | 13 |
| | 10 | 11 | 12 | 13 | 14 | 15 | 16 | 17 | 18 | 19 | 20 | 21 | 22 | 23 | 24 | 25 | 26 | 27 | 28 | 29 | |
| γ3 | L | I | T | T | V | G | A | F | A | A | F | S | L | M | T | I | A | V | G | T | 14 |
| γ2 | L | L | T | T | V | G | A | F | A | A | F | S | L | M | T | I | A | V | G | T | 15 |
| γ8 | L | I | T | T | I | G | A | F | A | A | F | G | L | M | T | I | A | I | S | T | 16 |
| γ4 | L | L | T | T | A | G | A | F | A | A | F | S | L | M | A | I | A | I | G | T | 17 |
| | 11 | 12 | 13 | 14 | 15 | 16 | 17 | 18 | 19 | 20 | 21 | 22 | 23 | 24 | 25 | 26 | 27 | 28 | 29 | 30 | |
| γ7 | L | I | S | S | V | F | G | A | C | G | L | L | L | V | G | I | A | V | S | T | 18 |
| γ5 | L | I | S | S | V | F | A | V | C | G | L | G | L | L | G | I | A | V | S | T | 19 |
| | * | | * | | | | * | | | # | | | * | | # | * | | # | | | |

\# single, fully conserved residue
\* relatively conserved residue
Bold and underlined-mutation candidates We identified the first transmembrane domain of γ6 as being necessary for the inhibitory effect of the subunit with chimeric proteins. Functional analysis using patch clamp showed that the N-terminal truncated γ6 still retained its inhibitory function; that the γ6 subunit lost its inhibitory function when the first transmembrane domain was substituted by the counterpart of γ4 subunit; and that the γ4 subunit gained an inhibitory function when its first transmembrane domain was replaced by the counterpart from the γ6 subunit. Furthermore, the replacements of the second, third and fourth domain between γ4 and γ6 did not change either subunits original function. Thus only the first transmembrane domain As mentioned, the first transmembrane domains of γ subunits are approximately 20 amino acids long and form α-helical structures. It is possible that the first transmembrane domain of γ6 binds to one of the α1 transmembrane domains through transmembrane helix-helix interaction. Van der Waals interaction between tightly packed helices, CαH—O hydrogen bonds across the helical backbone, and interhelical ion pairs are three possible driving forces for transmembrane helix association (Zhou, Cocco et al. 2000). For the first transmembrane domains of γ subunits, which lack charged residues, the possibilities are limited to the first two forces, which require close proximity between helices.

The GxxxG motif, where two glycine residues are separated by three residues (about out one helical turn), has been identified as the most frequently occurring sequence motif in transmembrane helices (Senes, Gerstein et al. 2000). Since the two glycines are separated by three residues, they are located next to each other on the same helical face. It is believed that their small side chains (consisting of just a hydrogen atom) create a physical space that enhances transmembrane helix-helix interactions (Curran and Engelman 2003). Additional research suggests that GxxxG related motifs, like the GxxxxxxG motif (Liu, Engelman et al. 2002), in which two glycine residues are located on the same face after two helical turns; and the (G/A/S) xxx(G/A/S) motif, in which small residues (glycine, alanine, and serine) in various combination occur on one face of a helix, have similar properties (Senes, Gerstein et al. 2000; Kleiger, Grothe et al. 2002; Leonov and Arkin 2005). It should be noted, however, that the context of adjacent residues may also be significant for (small)xxx(small) motif function.

Analyzing the first transmembrane domains of all γ subunits, we found that a GxxxA motif exists in some, but not all, of the isoforms. Specifically, the γ5 and γ7 subunits lack the motif. Interestingly, only the γ6 subunit has two GxxxA motifs. Furthermore, the two glycine residues are separated by 6 residues so that they likely occur on the same helical face. The existence of an additional alanine residue produces (GxxxAxxGxxxAxxA) creating what we predict to be a groove along almost the full length of one face of the γ6 first transmembrane domain (see FIG. 22 for theoretical three dimensional structure comparison between the γ6 and γ4 first transmembrane domains).

We have designed a number of point mutations in the γ subunits to test the hypothesis that the unique double GXXXA motifs in the first transmembrane domain of γ6 are significant for the inhibitory function of this protein. If so, it is interesting to determine whether the full-length groove is required for this function, or whether one GxxxA motif is sufficient. We also wanted to determine if these glycine residues could be substituted by other small side-chain residues without interfering with protein function. To address these questions, we used site directed mutagenesis to change the glycines in the GxxxA motifs at positions 42 and 49 to alanine or leucine (see FIG. 23 for the 3D structure). We also replaced leucine at position 23 on γ4 to glycine to test if a long groove (GxxxAxxGxxxA) on γ4 provided by this L23G mutation would act as a "gain-of function" mutation for γ4 (see FIG. 24 for the three dimensional schematic structure).

The results suggest that the first transmembrane domain of γ6 is not only necessary but also sufficient to produce inhibition of Cav3.1 calcium current. We also find that the glycine at position 42 ($Gly^{42}$; also corresponding to position 3 relative to a different starting reference) but not the glycine at position 49 ($Gly^{49}$) is critical for its inhibitory function, suggesting that the first GxxxA motif plays an important role for γ6 function.

Methods and Materials

Cell Culture. Stably transfected HEK-293 cells expressing Cav3.1 α1 subunit, obtained as a gift from Dottie Hank and the University of Chicago, were grown at 37° C. in Dulbecco's modified Eagles medium (DMEM Gibco BRL, Grand Island, N.Y.) with 10% FBS (ATCC), 1% penicillin/streptomycin in 5% $CO_2$. Geneticin (G418) was added at a concentration of 200 ug/mL for selection of transfected cells. Cells having a low-passage number (p<20) were used. The cells were kept frozen in FBS supplemented with 10% DMSO at –80° C. for stock. Cells were maintained in 25 $cm_2$ culture flasks (Corning). Medium was renewed every 24-48 hours. The cells were dissociated from the flasks with a 0.05% room temperature Trypsin-EDTA solution for 3 minutes and suspended with medium for low density replated for every 4-6 days. During re-plating, a fraction of the cells were plated on 35 mm culture dishes, which were then used for transfection and electrophysiology. Cells were again trypsinized and re-suspended in bath solution prior to use.

Transfection. HEK-293 cells stably transfected with the Cav3.1 α1 subunit were transiently transfected with vectors containing GFP and γ subunits cDNA when the cultures reached 50% confluency. Lipofectamine 2000 reagent (Invitrogen) was used following manufacturer's protocol.

Electrophysiology. Whole cell Ca2+ currents were recorded at room temperature using an Axon Instruments Axopatch-1D amplifier, a Digidata 1200 interface and pClamp8.0 software about 48 hours after transfection. Cell capacitance was typically around 10 pF, but ranged from 5-40 pF. Recording micropipettes were made from borosilicate glass (2-3 Mohms tip resistance), and filled with solution contained (in mM) 130 NaCl, 10 EGTA, 2 $MgCl_2$, 1 $CaCl_2$, 10 HEPES, 3 Tris-ATP, and 0.3 $Li_2GTP$ or 0.3 Tris-GTP. Tyrode's solution was used as the bath solution. It contained (in mM) 137 NaCl, 1 KCl, 1 $MgCl_2$, 0.33 $NaH_2PO_4$, 2 $CaCl_2$, 10 HEPES. Both solutions were adjusted to pH 7.4 with NaOH and 280 mOsm with sucrose.

We determined the biophysical characteristics of Cav3.1 currents in transfected HEK-293 cells and effects of the first transmembrane domain of γ4 and γ6 on these properties. Test parameters were optimized for studying Cav3.1 current. The time constant ($\tau$) of deactivation ($\tau_{deac}$) was obtained by single exponential fitting of tail currents. For Cav3.1 currents, the cells were clamped at a holding potential of –100 mV, then depolarized to –20 mV for 4 msec, and repolarized to various voltages from –120 mV to –60 mV at 10 mV interval for 150 msec to elicit tail currents.

The voltage dependence of activation was measured using tail currents. For Cav3.1 currents, the cells were clamped at a holding potential equal to –100 mV, and then depolarized briefly to a conditioning potential, varying from –90 mV to +60 mV, and finally clamped at –60 mV before inactivation. Using this protocol, all tail currents are elicited at the same driving force (at –60 mV), so the current amplitude accurately reflects the number of channels opened during the different conditioning potentials.

A series of conditioning prepulses of 500 msec were used to measure voltage dependence of inactivation in our experiments. Channels initially open and then reach steady-state inactivation during the 500 msec long prepulses. The membrane potential is stepped to a fixed test potential of –20 mV, where maximal peak current is elicited. Currents elicited at each test potential reflect how many channels are not in the inactivated state after a steady-state inactivation; that is, how many channels are available to open. The conditioning prepulse potentials were changed from –120 mV to 50 mV, and the test potential is fixed at –20 mV.

Data collection and analysis. To probe the structural features necessary for the function of γ subunits, we are using HEK-293 cell line stably transfected with Cav3.1 α1 subunit. These cells are then transiently transfected with vectors containing various chimeric, truncated or mutant gamma subunits. Since our previous data showed that γ6 had no effects on the kinetics of calcium currents, we focused on peak current density when we analyzed γ6 mutants. There is inherent variation in calcium current density in the HEK-Cav3.1 stable cell line likely due to differences in the batch used, passenger number, extent of cellular confluence, or for other unknown reasons. The averaged current density of each test group of cells was normalized to the mean current density of a parallel control group of cells plated from the same batch of cells and analyzed on the same day. A minimum of 5 cells (typically 7 to 10) from each group was used to calculate the mean behavior of test and control cells from each days recording. At least two independent transfections were performed for each test condition. Overall, averages were obtained from 21 control groups of cells that had been transfected with empty vector over several months. The data are pooled together to reduce the variance. Overall 166 control cells were recorded which had a mean current density of 47.86±1.31 pA/pF. The current density of the control cells over many months justified the pooling of data recorded from different batches of cells transfected with mutated γ subunits.

All data are reported as means +/− standard error of mean (S.E.M) and numbers of cells (n). Mean values are tested for statistical significance using single factor ANOVA. Differences between mean values were considered significance if the probability of error (p) was less than 0.05 and when significant p-values were encountered. Groups were compared against the control group with Dunnett test.

Results

The first transmembrane domain of γ6 is sufficient for the inhibitory effect of this isoform on Cav3.1 calcium current. Current traces elicited from HEK 293 cells that are stably transfected by the Cav3.1 αsubunit have the typical voltage dependency and kinetics of Cav3.1 calcium current (FIG. 24, Table3.2). Using the same cell line, we have demonstrated that the N-terminal region, including the first transmembrane domain of γ6 has an inhibitory effect on Cav3.1 calcium current (Hansen unpublished data). In order to test the effects of the first transmembrane domains of γ subunits on Cav3.1 calcium currents, we then added vectors encoding the complete γ4 or γ6 subunits and vectors containing only the first transmembrane domain of γ4 or γ6. The averaged current density of peak voltage for the various vectors (blank adcgi vector, adcgi-γ6, adcgi-γ4, adcgi-1stTM γ6 or adcgi-1stTM γ4) show that the γ6 subunits and the first transmembrane domain of γ6 subunits, but not the γ4 or its first transmembrane domain, cause a significant decrease in peak calcium current (FIG. 25C).

The γ6 subunit decreased peak current density 42% from control (48.43±2.62 pA/pF, n=45, control to 27.85±3.32 pA/pF, n=18, γ6). Co-expression of just the first transmembrane domain of γ6 decreased peak current density 20% (38.65±2.92 pA/pF, n=35). Both are statistically significant at P<0.05 (FIG. 25C).

In contrast, neither γ4 nor the first transmembrane domain of γ4 had a statistically significant effect on mean peak current density (mean values were 48.28±3.30 pA/pF, n=16, p>0.05 for γ4, and 56.34±5.01 pA/pF, n=20, p>0.05, for the first transmembrane domain of γ4) (FIG. 25C).

The γ6 subunit (−28.75±0.80 mV (n=20)) produced a slight shift in the positive direction (about 5 mV) for peak voltage, the membrane potential at which peak current is reached, as compared to control group (−24.29±0.63 mV (n=20)). A smaller positive shift of about 3 mV was seen for the first transmembrane domain of γ6 (−26.00±1.00 mV (n=20)). Both are statistically significant at p<0.05 (Table 3.2). Small currents are observed which are typical for cells transfected with γ6 subunit and its first transmembrane domain. It is possible that the slight positive shift is an artifact due to the difficulty of making accurate measurements from the tiny currents. This possibility was tested by comparing a high current and a low current group from the control cells. A set of 20 recordings were pooled from two independent experiments, regrouped them into two groups, and determined their averaged peak current to be −709.1±70.3 pA (n=10) for the high current group, and −362.8±26.6 pA (n=10) for the low current group, which was similar to a group transfected with γ6 (−344.2±48.4, n=10). There is a two-fold difference between these rearranged groups in mean of peak current, but the peak voltages were almost the same, −29.0±1.0 mV (n=10) and −28.5±1.3 mV (n=10), respectively. Thus, the voltage differences for both γ6 subunit and its first transmembrane are most likely due to regulation of Cav3.1 calcium current.

TABLE 3.2

Effects of γ4, γ6, γ4 and γ6 first transmembrane domain on the biophysical properties of Cav3.1 dependent current in Cav3.1-HEK cells.

|  | Cav3.1 + adcgi | Cav3.1 + γ6 | Cav3.1 + γ6 1stTM | Cav3.1 + γ4 | Cav3.1 + γ4 1stTM |
|---|---|---|---|---|---|
| Activation | | | | | |
| V peak (mV) | −28.75 ± 0.80 (n = 20) | −24.29 ± 0.63 (n = 20) | −26.00 ± 1.00 (n = 20) | −29.44 ± 1.89 (n = 18) | −28.57 ± 0.82 (n = 14) |
| V½ (mV) | −31.5 ± 2.00 (n = 10) | −28.12 ± 4.07 (n = 4) | −30.33 ± 2.32 (n = 7) | −31.62 ± 3.24 (n = 8) | −29.71 ± 2.03 (n = 9) |
| K | 11.11 ± 0.47 (n = 10) | 11.99 ± 1.39 (n = 4) | 10.85 ± 0.49 (n = 7) | 12.83 ± 0.79 (n = 8) | 13.29 ± 0.70 (n = 9) |
| Time to peak @−25 mV | 11.71 ± 1.13 (n = 20) | 9.03 ± 0.57 (n = 20) | 11.06 ± 0.97 (n = 20) | 8.37 ± 0.39 (n = 18) | 9.00 ± 0.51 (n = 14) |
| Inactivation | | | | | |
| V½ (mV) | −65.22 ± 0.91 (n = 10) | −67.53 ± 4.81 (n = 4) | −62.43 ± 0.65 (n = 7) | −67.77 ± 1.86 (n = 8) | −66.17 ± 0.83 (n = 9) |
| K | −5.52 ± 0.12 (n = 10) | −5.42 ± 0.34 (n = 4) | −5.54 ± 0.12 (n = 7) | −6.04 ± 0.24 (n = 8) | −5.92 ± 0.12 (n = 9) |
| τ (ms) @−20 mV | 24.3 ± 1.5 (n = 10) | 23.9 ± 1.6 (n = 4) | 24.0 ± 1.3 (n = 7) | 27.3 ± 1.4 (n = 8) | 25.5 ± 0.9 (n = 7) |
| Deactivation | | | | | |
| τ (ms) @−100 mV | 2.21 ± 0.12 (n = 10) | 2.22 ± 0.19 (n = 4) | 2.01 ± 0.21 (n = 7) | 2.20 ± 0.11 (n = 8) | 2.40 ± 0.22 (n = 7) |

There was no significant shift for the peak voltage found when the γ4 subunit or its first transmembrane domain was introduced into the cells (mean value were −29.44±1.89 mV n=18, −28.57±0.82 mV, n=14, for γ4 and its first transmembrane domain respectively) (Table 3.2).

The voltage dependency of activation and inactivation, and the kinetics for activation, inactivation and deactivation have been analyzed (Table 3.2 and FIG. 26, 3.6). There is no significant difference among cells co-expressed with the various γ subunits and their first transmembrane domains for any of those biophysical properties.

The first transmembrane domain of γ6 had a reduced inhibitory effect on Cav3.1 dependent calcium current in HEK-293 cells compared to the full length γ6 subunit. This decreased inhibitory effect might be due to more rapid digestion or altered targeting of the TM1 construct. To test the ability of TM1 to associate with the membrane, we constructed two GFP fusion proteins containing GFP and the first transmembrane domain from γ6 and γ4, respectively. Western blot experiments indicated these GFP-tagged first transmembrane domains were located in the cell membrane (FIG. 28 courtesy of Janice Jones). Whole cell recording indicated that the GFP-γ6 TM1 fusion protein had a similar inhibitory function as γ6 TM1 (FIG. 25C and FIG. 30B).

These results demonstrate that the first transmembrane of γ6 is both necessary and sufficient for the inhibitory effect of the subunit on peak Cav3.1 calcium current density.

Site directed mutagenesis to determine the role of specific residues and sequence motifs. A goal of this study was to identify significant motifs or residues for γ6 function. We generated site specific mutations targeting some specific residues in the first transmembrane domain which we identified as the structurally important functional region. We transiently transfected bicistronic vectors encoding GFP and either γ6 or γ4, or a mutant to test their function on Cav3.1 calcium currents. The current densities of peak voltage for these various sets of co-expression were measured, and compared (FIG. 30). See also Table 3.3.

and 49 were mutated to either leucine (relatively large side-chain) or alanine (relatively small side-chain). When the G42A mutant was expressed, Cav3.1 current density decreased to 73.4%±8.9% (n=19) ($p<0.05$) relative to control levels. With the G42L mutant, current density was 107.5%±10.9% (n=16) compared with control. These results indicate that a relatively small side chain at position 42 is necessary for the inhibitory activity of the first transmembrane domain of γ6 (FIG. 30).

Two mutants at Gly$^{49}$ (G49A and G49L) were tested. Relative to control values, current densities were 67.6%±5.9% (n=36) and 73.1%±4.8% (n=22) for the two mutations, respectively. These results show that both mutations on γ6 Gly49 retained the inhibitory function of the γ6 subunit on Cav3.1 calcium currents. We suggest that strict maintenance of the glycine at position 49 is not crucial for γ6 function and further suggest that the importance of an amino acid residue can depend on its location or context.

To test whether the double GxxxA motifs or the GxxxxxxG motif is required for γ6 inhibitory function, we also mutated Leu$^{23}$ to Gly (L23G) on γ4. This change introduced the second GxxxA motif and a GxxxxxxG motif to γ4 (GxxxAxxG23xxxA). The current density with the γ4 subunit was 116.02%±11.4% (n=20), and that of the mutant (L23G) of γ4 was 99.9%±7.8% (n=15) compared to control. Both γ4 and this mutant (L23G) have no significant effect on Cav3.1 calcium current. Thus, the γ4 did not gain inhibitory function when the GxxxAxxGxxxA motif was constructed. We therefore suggest that the specific location of a structural motif, for example on helices, can be important for its function.

Discussion

We showed the γ6 subunit to be a unique modulator of voltage dependent calcium current that decreases current density by about 50% without a significant effect on kinetics. In contrast, neither γ4 nor γ7 has any significant effect on calcium current in various contexts. Further, using chimeric proteins constructed with different transmembrane domains from γ6 and γ4, we demonstrated that the N-terminal region

TABLE 3.3

Normalized current density of gamma subunits (γ6, γ4, and variants).

|  | Vector | γ6 | γ6 L43S | γ6 G42A | γ6 G42L | γ6 G49A | γ6 G49L | γ4 | γ4 L43S |
|---|---|---|---|---|---|---|---|---|---|
| Normalized Current Density | 100.0% | 55.4% | 48.2% | 73.4% | 107.5% | 67.6% | 73.1% | 116.0% | 99.9% |
| Standard error | 4.4% | 5.7% | 7.3% | 8.9% | 10.9% | 5.9% | 4.8% | 11.4% | 7.8% |
| Cell number | 91 | 32 | 20 | 19 | 16 | 36 | 22 | 20 | 15 |

We developed and studied a γ6 mutation at position 43 involving substitution of the Leucine (Leu$^{43}$) with serine (L43S) to determine if this leucine residue is important for γ6 subunit function. After co-expressing this mutant, Cav3.1 calcium current density decreased to 48.2%±7.2% (n=20) compared with control (FIG. 30B, Table 3.2). The wild type γ6 subunit decreased Cav3.1 calcium peak current density 45% from control (100%±4.4%, n=91, control to 55.4%±5.7%, n=32, γ6). Therefore, this mutation does not change the γ6 inhibitory effect on Cav3.1 calcium current. Thus, strict maintenance of this leucine residue at position 43 is not critical.

To test the importance of glycine residues on the first transmembrane domain of γ6, glycine residues at position 42 which included the first transmembrane domain of γ6 was required for its modulation. We have also probed the function of specific amino acids and sequence motifs to determine which have structural relevance for the function of γ6 subunit.

We found that the first transmembrane domain of γ6 can be sufficient to decrease current density of Cav3.1 dependent calcium currents. Neither γ4 subunit nor its first transmembrane domain had any effects on Cav3.1 dependent calcium currents. This is the first report that the first transmembrane domain can be sufficient for the γ6 subunit inhibitory effect on calcium channel function.

Once the functional domain was narrowed down to the first transmembrane domain of γ6, our structural and functional analysis then focused on this region. We tested a substitution of leucine with serine, γ6 (L43S). This substitution (L43S) is from a non-polar residue to a polar amino acid as is found at that position by alignment with certain other γ subunits. However, mutant L43S did not alter the inhibitory function of γ6. Thus, the difference between non-polar and polar residues such as threonine/serine is not critical at this position. This finding is interesting in light of reports that polar or charged amino acid residues are often important for the function of transmembrane domains (Curran and Engelman 2003).

When analyzing sequences within γ subunit transmembrane domains, we found that G/AxxxG/A motifs exist in all γ subunits. The γ6 subunit is unique, however, in having two GxxxA motifs in its first transmembrane domain; this structural feature can create a groove along one face of the helix. We note that the groove is extended by the existence of an additional alanine (A56) residue (G42xxxAxxG49xxxAxxA56). The (Small)xxx(Small) motif and the GxxxxxxG motif can be important for enhancing and stabilizing helix-helix interactions. Our determining the unique structural aspects of γ6 led us to further test whether the long groove, GxxxxxxG, or the repeated GxxxA motifs are significant in the function of γ6.

We tested mutations of the glycine residue at position 49 (G42xxxAxxG49xxxAxxA56). We thought it might be critical, since it is located in the middle of the long groove of γ6, at the end of the GxxxxxxG motif, and also at the beginning of the second GxxxA motif. Mutation of this glycine can help illuminate the involvement of those proposed structures and motifs in determining γ6 function. This glycine was changed to generate individual mutants of alanine (G49A; to increase the size of the side-chain slightly) and to leucine (G49L; to increase the side-chain to a relatively larger size). One goal was to test whether side-chain size at this particular position is important. Both mutants retained the inhibitory effect, however, indicating that strict maintenance of this glycine (Gly$^{49}$) is not critical for γ6 function on calcium current. We suggest that these results can indicate: a) that the whole length of the groove on the first transmembrane domain of γ6 is not required for γ6 function, since the G49L mutant interrupted the long groove; b) that the proposed GxxxxxxG motif alone, only found in γ6, may not be responsible for its function, since the function remained when the glycine at the end was replaced by leucine; c) that the second motif is not necessary for γ6 function; and d) that only the first GxxxA motif may be critical for the inhibitory function of the first transmembrane domain of γ6.

To confirm the importance of the first GxxxA motif, glycine at position 42 was replaced by alanine or leucine, to change the side-chain of residues from relatively small to large. The γ6 function was completely lost when the glycine at position 42 was replaced by leucine (G42L), suggesting this glycine is critical and is necessary for γ6 function (see FIG. 30). In addition, the γ6 inhibitory function remained, but at reduced level, for the G42A mutant, suggesting that interruption of function for mutant (G42L) was due at least in part to the size of the side-chain. Presumably, the glycine residue (which only has a hydrogen atom for its side-chain) can provide the closest contact point for an interaction. Substitution with alanine (which also has a small side-chain) can increase the contact distance but can still preserve the interaction. When leucine (with its large side chain) is introduced, however, the capability for interaction is disrupted.

Overall, our finding is consistent with the idea that the (Small)xxx(Small) motif near the N-terminal end of the first transmembrane domain is necessary for γ6 function. The different results obtained with the wild type and mutants (G42A and G42L) further suggest that the size of side-chains may affect the efficiency of this motif for enhancement of intermembrane helix-helix interaction. Glycine can potentially provide an optimal condition to permit such interaction.

We attempted to create a structure on γ4, similar to that of γ6, by mutating a leucine to glycine (L23G). With this substitution, there would be a long groove on one face of γ4 (GxxxAxxG$^{23}$xxA), including repeated GxxxA motifs, and a GxxxxxxG motif. However, the mutant did not show inhibitory function like γ6 does. Thus, this substitution did not produce a "gain-of-function" mutation of γ4. This result confirms that repeated GxxxA motifs are not necessary for γ6's inhibitory function. Furthermore, a single GxxxA motif (γ4 has one) may not be able to exert its function if it is in the wrong relative position. Thus both the location and the context of the structural motif can also be important for its function.

We predicted that the importance of the first GxxxA motifs on the first transmembrane domain of γ6 could be further tested by creating a γ6 mutation at A46. We predict that introduction of a large side chain residue at this position should inhibit its function. This experiment showed that the mutant A46I (alanine replaced by isoleucine) did not inhibit calcium current, confirming the importance of the first GXXXA motif.

Other efforts can be performed to further identify the importance of location and context of the first GxxxA motifs on the first transmembrane domain of γ6. As a first example, γ4 (T23G) would introduce a GxxxA in relatively the same position of γ4 as in γ6. As a second example, a γ1 double mutant (T12G, I16G) would create in γ1 a very similar first transmembrane domain as in γ6. In an investigation of native γ1 it was determined that it had no effect on Cav3.1 calcium current. The doubly mutated γ1 (T12G, I16G) can be useful to illustrate the importance of location and context for the function of the GxxxA motif in the event γ1 gained inhibitory function.

The GxxxG motif has been investigated for the dimerization of the glycophorin A (GpA) transmembrane helices (Lemmon, Flanagan et al. 1992; Mendrola, Berger et al. 2002). Some GxxxG-like motifs' functions were explored in a variety of protein families, including ErbB receptor (Mendrola, Berger et al. 2002; Gerber, Sal-Man et al. 2004), F0F1-ATP synthase (Arselin, Giraud et al. 2003), G-protein-coupled receptors (Chinault, Overton et al. 2004), and major coat protein (MCP) (Melnyk, Kim et al. 2004). Recently, such a motif was studied for the ability to mediate α-helical interaction in soluble proteins (Mottamal and Lazaridis 2005). Our finding, however, is the first report that a GxxxG-like motif can mediate subunit function for calcium channels.

We have characterized the inhibitory function of γ6 on Cav3.1 ($α1_G$), Cav3.2 ($α1_H$), and Cav2.3 ($α1_E$) calcium channels. A full-length wild-type gamma6 was able to mediate a decrease in calcium current for several isoforms of pore-forming subunits and hence several different calcium channels.

We can further examine the interaction between α1 and γ6 subunits. Our results suggest that the GxxxA motif at the N-terminal of the first transmembrane domain of γ6 can mediate this interaction. This is consistent with our mammalian 2-hybrid assay efforts, where we did not find interaction between γ6 and any intracellular region of the Cav3.1 α1 subunit; this supports the idea that α1-γ6 interaction involves transmembrane helix-helix association.

We can address the issue of the location of the interaction site on the α1 subunit for α1-γ6 helix-helix interaction. Based on sequence analysis, some GxxxA motifs located on the transmembrane domain of the Cav calcium channel α1 subunit may serve as potential interaction locations.

We propose that the α1-γ6 association is mediated by a GxxxA motif. The intersubunit association may occur before or after the subunits are inserted into the plasma membrane. Upon binding with γ6, the channel will undergo some conformational rearrangement that changes channel properties. The fact that the force of an α1-γ6 interaction is potentially as strong as a pairing of charged residues may explain why the γ6 inhibitory function on calcium current brings about the observed relative levels of change in current density.

The γ2, γ3 γ4, and γ8 subunits, a subgroup of calcium channel γ subunits, have been shown to regulate AMPA receptor trafficking and (TARPs) (Vandenberghe, Nicoll et al. 2005). They can mediate surface expression of AMPA receptors. Previously, the C-terminal PDZ motif was the only functional domain identified, as trafficking was the only recognized function for this subunit family. Two studies have reported about the effects of γ2 on AMPA receptor kinetics, including increasing the channel opening rate, decreasing desensitization, and slowing the deactivation (Priel, Kolleker et al. 2005; Tomita, Adesnik et al. 2005). The C-terminal portion is apparently not involved in γ2's modulatory function. Thus, there could be other distinct domains responsible for the direct interaction between γ2 and AMPA receptor. The first extracellular loop may be the site of this interaction based on functional analysis of a γ2/γ5chimera (Tomita, Adesnik et al. 2005).

The TM1 domain (and more discrete subdomain structures, e.g. a GxxxA motif with potential influence by the surrounding region) can potentially serve in the role of interaction with an AMPA receptor.

Overall, we demonstrate that the first transmembrane domain of γ6 is sufficient for its inhibitory function on Cav3.1 calcium current, and that glycine at position 42 of γ6 ($G^{42}$) is critical for its function. We believe that the functionality of glycine is likely due to the structural feature of the small size of its side chain. Our data strongly suggests the involvement of the GxxxA motif in γ6 function, but we also note that its location and the sequence surrounding that motif can also be very important.

References Cited in Example 3

Arikkath, J. and K. P. Campbell (2003). "Auxiliary subunits: essential components of the voltage-gated calcium channel complex." Curr Opin Neurobiol 13(3): 298-307.

Arikkath, J., C. C. Chen, et al. (2003). "Gamma 1 subunit interactions within the skeletal muscle L-type voltage-gated calcium channels." J Biol Chem 278(2): 1212-9.

Bahinski, A., A. Yatani, et al. (1997). "Charged amino acids near the pore entrance influence ion-conduction of a human L-type cardiac calcium channel." Mol Cell Biochem 166(1-2): 125-34.

Chu, P. J., H. M. Robertson, et al. (2001). "Calcium channel gamma subunits provide insights into the evolution of this gene family." Gene 280(1-2): 37-48.

Curran, A. R. and D. M. Engelman (2003). "Sequence motifs, polar interactions and conformational changes in helical membrane proteins." Curr Opin Struct Biol 13(4): 412-7.

Curtis, B. M. and W. A. Catterall (1984). "Purification of the calcium antagonist receptor of the voltage-sensitive calcium channel from skeletal muscle transverse tubules." Biochemistry 23(10): 2113-8.

De Jongh, K. S., C. Warner, et al. (1991). "Characterization of the two size forms of the alpha 1 subunit of skeletal muscle L-type calcium channels." Proc Natl Acad Sci USA 88(23): 10778-82.

De Waard, M., M. Pragnell, et al. (1994). "Ca2+ channel regulation by a conserved beta subunit domain." Neuron 13(2): 495-503.

De Waard, M., V. E. Scott, et al. (1996). "Identification of critical amino acids involved in alpha1-beta interaction in voltage-dependent Ca2+ channels." FEBS Lett 380(3): 272-6.

Doura, A. K., F. J. Kobus, et al. (2004). "Sequence context modulates the stability of a GxxxG-mediated transmembrane helix-helix dimer." J Mol Biol 341(4): 991-8.

Freise, D., B. Held, et al. (2000). "Absence of the gamma subunit of the skeletal muscle dihydropyridine receptor increases L-type Ca2+ currents and alters channel inactivation properties." J Biol Chem 275(19): 14476-81.

Gurnett, C. A., R. Felix, et al. (1997). "Extracellular interaction of the voltagedependent Ca2+ channel alpha2delta and alpha1 subunits." J Biol Chem 272(29): 18508-12.

Kleiger, G., R. Grothe, et al. (2002). "GXXXG and AXXXA: common alpha-helical interaction motifs in proteins, particularly in extremophiles." Biochemistry 41(19): 5990-7.

Leonov, H. and 1. T. Arkin (2005). "A periodicity analysis of transmembrane helices." Bioinformatics 21(11): 2604-10.

Liu, Y., D. M. Engelman, et al. (2002). "Genomic analysis of membrane protein families: abundance and conserved motifs." Genome Biol 3(10): research0054.

Melnyk, R. A., S. Kim, et al. (2004). "The affinity of GXXXG motifs in transmembrane helix-helix interactions is modulated by long-range communication." J Biol Chem 279 (16): 16591-7.

Pichler, M., T. N. Cassidy, et al. (1997). "Beta subunit heterogeneity in neuronal L-type Ca2+ channels." J Biol Chem 272(21): 13877-82.

Pragnell, M., M. De Waard, et al. (1994). "Calcium channel beta-subunit binds to a conserved motif in the I-II cytoplasmic linker of the alpha 1-subunit." Nature 368(6466): 67-70.

Priel, A., A. Kolleker, et al. (2005). "Stargazin reduces desensitization and slows deactivation of the AMPA-type glutamate receptors." J Neurosci 25(10):2682-6.

Scott, V. E., M. De Waard, et al. (1996). "Beta subunit heterogeneity in N-type Ca2+ channels." J Biol Chem 271(6): 3207-12.

Senes, A., M. Gerstein, et al. (2000). "Statistical analysis of amino acid patterns in transmembrane helices: the GxxxG motif occurs frequently and in association with beta-branched residues at neighboring positions." J Mol Biol 296 (3): 921-36.

Tomita, S., H. Adesnik, et al. (2005). "Stargazin modulates AMPA receptor gating and trafficking by distinct domains." Nature 435(7045): 1052-8.

Tomita, S., L. Chen, et al. (2003). "Functional studies and distribution define a family of transmembrane AMPA receptor regulatory proteins." J Cell Biol 161(4): 805-16.

Van Petegem, F., K. A. Clark, et al. (2004). "Structure of a complex between a voltage-gated calcium channel beta-subunit and an alpha-subunit domain." Nature 429(6992): 671-5.

Vandenberghe, W., R. A. Nicoll, et al. (2005). "Stargazin is an AMPA receptor auxiliary subunit." Proc Natl Acad Sci USA 102(2): 485-90.

Zhou, F. X., M. J. Cocco, et al. (2000). "Interhelical hydrogen bonding drives strong interactions in membrane proteins." Nat Struct Biol 7(2): 154-60.

EXAMPLE 4

Further Variants of gamma6 Peptides

Variants of gamma6 peptides capable of calcium channel regulation are generated. Based on Chu et al., 2001, the relationship of gamma6 subunits from rat, mouse, and human show difference of about 20% in phylogenetic relationships for amino acid sequences (see FIG. 4 therein). Therefore we generate peptide variants having homology to a gamma6 fragment of about at least 80%, about at least 85%, about at least 90%, or about at least 95%. In particular, the gamma6 fragment is a TM1 domain.

EXAMPLE 5

Inhibition of Endogenous Expression of gamma6

With this disclosure of the significance of subunit gamma6 regarding calcium channel function, therapeutic interventions are developed. An RNA-interference approach is used to at least partially silence gene expression of the gamma6 subunit using and adapting techniques available in the art (e.g., see US 20050209180, 20050209179, 20050203040). The approach can use exogenously added siRNA or vector-driven technology. In an alternative approach, antisense technology is used to modify gene expression. In an embodiment, if the native function of a gamma6 subunit is to decrease calcium current, a down regulation of the gamma6 subunit can result in a relative increase of calcium current.

EXAMPLE 6

A Critical GXXXA Motif in the First Transmembrane Domain of the gamma6 Calcium Channel Subunit Mediates its Inhibitory Effect on $Ca_v3.1$ Calcium Current Introduction. Calcium channel γ subunits comprise a family of eight proteins that share a common primary structure consisting of four transmembrane domains with intracellular N- and C-terminal ends. The first member of this protein family to be described, $\gamma_1$, was isolated as a subunit of the high voltage activated (HVA), L-type calcium channel found in skeletal muscle. Unlike other calcium channel accessory subunits (β, $\alpha\text{-}_2\delta$) which enhance calcium current, $\gamma_1$ was shown to suppress L-type calcium current in heterologous systems when co-expressed with an HVA, L-type pore forming α subunit. Skeletal muscle isolated from knockout mice lacking the $\gamma_1$ gene have increased L-type calcium current density confirming a physiological role of $\gamma_1$ as a negative regulator of HVA, L-type calcium current density in developing skeletal myocytes.

Phylogenetic and sequence homology analysis indicates that the recently described $\gamma_6$ protein is the closest homologue of $\gamma_1$ within the γ subunit family. Both $\gamma_1$ and $\gamma_6$ have short C-terminal regions that lack the consensus PDZ-binding motif that is a notable characteristic of the four γ subunits known collectively as the TARP proteins ($\gamma_2$, $\gamma_3$, $\gamma_4$, and $\gamma_8$). The $\gamma_1$ and $\gamma_6$ subunits also share similarities in their tissue distribution since both are expressed primarily or exclusively in striated muscle. As mentioned, the $\gamma_1$ subunit was originally isolated from skeletal muscle and its expression seems largely limited to that tissue. mRNA encoding the $\gamma_6$ subunit is robustly expressed in cardiac myocytes as two distinct isoforms of varying length and mRNA encoding the full length isoform of $\gamma_6$ is also expressed in skeletal muscle. Given the similarities in molecular evolution, structure and tissue distribution between $\gamma_1$ and $\gamma_6$, it seemed likely that the $\gamma_6$ subunit might share with $\gamma_1$ an ability to modulate myocyte calcium current. This prediction was recently confirmed. Co-expression of the $\gamma_6$ subunit cloned from cardiac muscle with the pore forming α1 subunits of low voltage activated (LVA) calcium channels (Cav3.1) known to be expressed in the heart dramatically decreases calcium current (Hansen, Chien et al. 2004). The other γ subunits found in cardiac myocytes ($\gamma_4$, $\gamma_7$) do not cause an inhibition of Cav3 dependent calcium current; a finding that is consistent with the prediction that the $\gamma_6$ subunit shares with $\gamma_1$ unique functional effects on myocyte calcium channels.

To identify critical sequences or structural features within the $\gamma_6$ subunit that are involved in its modulation of LVA calcium current, we have created a series of truncated γ subunits lacking either their N- or C-terminal cytoplasmic regions and a series of chimeric γ subunit proteins in which portions of $\gamma_6$ are replaced by the homologous sequences from $\gamma_4$. Analysis of the effects of the engineered proteins reveals that the first transmembrane (TM1) domain of $\gamma_6$ is necessary for the inhibitory effect of the subunit. Further analysis using single amino acid substitutions has identified a critical GXXXA motif within TM1 of γ6 that is required for its inhibitory effect on calcium current. These results suggest a potential mechanism where a helix-helix interaction between TM1 of $\gamma_6$ and an as yet unidentified helix in the $\alpha_1$ subunit is necessary for the function of the $\gamma_6$ subunit.

Methods

Cell culture. Stably transfected HEK-293 cells expressing the Cav3.1 $\alpha_1$ subunit, obtained as a gift from Professor Dottie Hank at The University of Chicago, were grown at 37° C. in Dulbecco's modified Eagles medium (DMEM Gibco BRL, Grand Island, N.Y.) with 10% FBS (ATCC), 1% penicillin/streptomycin in 5% $CO_2$. Geneticin (G418) was added at a concentration of 200 μg/mL for selection of transfected cells. Cells having a low-passage number (p<20) were used and were maintained in 25 cc culture flasks. Medium was renewed every 24-48 hours. The cells were dissociated from the flasks with a 0.05% room temperature Trypsin-EDTA solution for 3 minutes and suspended with medium for low density re-plating every 4-6 days. During re-plating, a fraction of the cells were plated on 35 mm culture dishes, which were then used for transfection and electrophysiology. Cells were again trypsinized and re-suspended in bath solution prior to use.

Transfection. HEK-293 cells stably transfected with either Cav3.1 or Cav3.2 were transiently transfected, at 50% confluency, with a bicistronic vector encoding both GFP and γ subunit cDNA's using Lipofectamine 2000 reagent (Invitrogen, Carlsbad, Calif.) as per the manufacturer's recommendations. Cells were visualized using an Nikon inverted microscope with an FITC filter.

Electrophysiology. Whole cell $Ca^{2+}$ currents were recorded using an Axon Instruments Axopatch-1D amplifier and Clampex 8.0 software. Pipettes were made from borosilicate glass and had typical resistances of 2-4 Mohms. The pipette solution contained (in mM) 130 NaCl, 10 EGTA, 2 or 5 $MgCl_2$, 1 $CaCl_2$, 10 HEPES, 3 Tris-ATP, and 0.3 $Li_2GTP$. Two different bath solutions were used. The first, used for experiments with γ subunit chimeras, contained (in mM) 130 NaCl, 1 $MgCl_2$, 2 $CaCl_2$, 10 glucose, 10 HEPES, and 0.03 TTX. The second, used for experiments with γ subunit containing point mutations, contained (in mM) 137 NaCl, 1 KCl, 1 $MgCl_2$, 0.33 $NaH_2PO_4$, 2 $CaCl_2$, 10 HEPES. All solutions were adjusted to pH 7.4 with NaOH and 280 mOsm with sucrose. No $Cl^-$ currents were evident in any HEK-293 cells line, stably transfected or not, and no attempt was made to eliminate Cl⁻ currents from data records.

All electrophysiological data are from current records in which voltage offset was adjusted, pipette capacitance and whole cell capacitance were compensated and series resistance was compensated to >80%. Currents were filtered at 10 kHz and recorded at 40 kHz. In some cases, current records were off-line filtered at 1K. Current voltage relationships were recorded using an on-line P/−4 subtraction procedure to eliminate linear capacitative and leakage currents. Only recordings with less than 50 pA leakage current were used.

Several different protocols were used to determine the biophysical characteristics of currents in HEK-293 cells. The voltage dependence of activation was determined using "tail" currents. Cells were depolarized from a holding potential of −100 mV to test potentials ranging from −90 mV to +60 mV. Pulse durations varied and corresponded to the time to peak current measured at the corresponding test potentials. Following the conditioning pulse cells were re-polarized to −60 mV and the amplitude of the resulting "tail" current measured. The voltage dependence of inactivation was measured by depolarizing the cells to voltages ranging from −120 mV to 50 mV for 500 ms to inactivate the $Ca^{2+}$ channels. After this conditioning step the membrane was returned to the holding potential (−100 mV) for 3 ms and then depolarized a second time to +20 mV for 150 ms during which time the peak current was measured. Time constants for inactivation were measured by fitting a single exponential equation to the decay phase of currents elicited by voltage steps from −50 to +30 mV from a holding potential of −100 mV. Time constants for deactivation were measured by fitting either a single or a double exponential to the decay phase of tail currents.

To account for the inherent variation in calcium current density in the HEK-Cav3.1 stable cell line the averaged current density of each test group of cells was normalized to the mean current density of a control group of cells. A minimum of 5 cells (typically 7 to 10) from each group was used to calculate the mean current densities of test and control cells. At least two independent transfections were performed for each test condition.

All data are reported as means +standard error of mean (S.E.M). Mean values were tested for statistical significance using single factor ANOVA with a p-value of 0.05. Statistically significant differences were explored using a Dunnett post-hoc test.

Immunoprecipitation and Immunodetection. HEK-293 cells stably transfected with Cav3.1 were grown in T25 tissue culture flasks and transiently transfected when 70-90% confluent. Five μg of each plasmid expression vector was transfected per T25 flask using 15 μL Lipofectamine 2000 reagent (Invitrogen, Carlsbad, Calif.) as per the manufacturer's recommendations. Cells were processed for immunoprecipitation assay and immunoblot analysis 24 hr post-transfection. Cells were washed and scraped from flasks with ice cold PBS (without $Ca^{2+}$ or $Mg^+$) and centrifuged for 5 min at 500×g at 4° C. Cell pellets were resuspended in 1.0 mL lysis buffer (50 mM Tris HCl, 150 mM NaCl, 1 mM EDTA, 2% Triton X-100, and 1:100 Protease Inhibitor Cocktail Set III (EMD Biosciences, San Diego, Calif.)) and incubated with constant mixing for 1 hr at 4° C. Samples were cleared by centrifugation at 10,000×g for 2 min at 4° C. Equal amounts of cell lysate were added to a 75 μL bed volume of anti-FLAG M2 affinity gel (Sigma, St. Louis, Mo.) that was washed three times with lysis buffer. Samples were immunoprecipitated with constant mixing overnight at 4° C. Beads were washed three times with lysis buffer and incubated in sample buffer containing 1% SDS, 50 mM DTT, and 10% glycerol for 30 minutes at 25° C. Protein samples were separated from the beads and transferred to new tubes with polyethylene spin columns (Pierce, Rockford, Ill.). Equal amounts of cell lysate and immunoprecipitate were separated by SDS-PAGE on 6% or 12% polyacrylamide gels containing 0.4% SDS. Samples were transferred to PVDF membrane and immunoblotted. For detection of Cav3.1 and the FLAG epitope, polyclonal anti-Cav3.1 antibody (Alomone Laboratories, Jerusalem, Israel) and polyclonal anti-FLAG antibody (Sigma, St. Louis, Mo.) were used, respectively, both at 1:1,000 dilution. HRP-conjugated goat anti-rabbit IgG secondary antibody (Zymed, South San Francisco, Calif.) was used at 1:20,000 dilution. Chemiluminescent detection was performed using ECL reagent (Amersham Biosciences, Piscataway, N.J.).

Results

We have previously shown that co-expression of the $\gamma_6$ subunit with the calcium channel $\alpha_1$ subunit Cav3.1 causes a significant decrease in LVA calcium current density when compared to the expression of Cav3.1 alone (Hansen et al., 2004; also see FIG. 38 this paper). This inhibitory effect is unique to the $\gamma_6$ isoform as no inhibition is seen with $\gamma_4$. A simple hypothesis to explain this difference is that the $\gamma_6$ subunit interacts directly with Cav3.1 to produce its effect on LVA calcium current while sequence differences in $\gamma_4$ either prevent or alter its interaction with Cav3.1 making $\gamma_4$ ineffective as a regulator of LVA current.

To test the idea that $\gamma_6$ and $\gamma_4$ interact differently with Cav3.1, coimmunoprecipitation was used to assay γ/Cav3.1 binding (FIG. 36). Flag-tagged γ subunits were transiently expressed in HEK-293 cells that stably expressed Cav3.1. Cell lysates were immunoprecipitated with Flag antibody and then probed with anti-$\alpha_1$G antibody to identify γ/Cav3.1 complexes. As shown (FIG. 36A), there was robust coimmunoprecipittion of γ6 with Cav3.1 indicating a strong physical interaction between these two calcium channel subunits. In contrast, the interaction between Cav3.1 and $\gamma_4$ was significantly reduced, being approximately 10% of $\gamma_6$ (FIG. 36B). Thus the inability of $\gamma_4$ to alter calcium current density is likely due to its reduced ability to form a stable complex with Cav3.1.

Based on these results we designed $\gamma_6/\gamma_4$ chimeras with the goal of identifying regions within the $\gamma_6$ subunit that are necessary for its function.

Effects of γ Subunit Chimeras on LVA Calcium Current Density of Heterologously Expressed Cav3.1 Channels:

We have previously shown that the short subunit of $\gamma_6$ ($\gamma_{6S}$) has the same effect on Cav3.1 calcium current as the full length protein, $\gamma_{6L}$. Thus the sequence deleted in the naturally occurring short isoform can not be required for the inhibitory action of the $\gamma_6$ subunit. The $\gamma_{6S}$ isoform is missing all of the second transmembrane domain and much of the third transmembrane domain of the full length protein (FIG. 10). Therefore sequence motifs that are required for the unique ability of $\gamma_6$ to decrease LVA current density must be found outside of the central core of the protein. To confirm this prediction, a chimeric subunit was engineered that combined the N- and C-terminal regions of $\gamma_6$ (including TM1 and TM4 and the associated cytoplasmic tails) with TM2 and TM3 from $\gamma_4$. This construct, $\gamma_{6446}$, was then transfected into Cav3.1/HEK cells and the calcium current density compared to that of positive controls transfected with wild-type $\gamma_6$ (which show decreased current) and negative controls transfected with $\gamma_4$ (in which current is unaffected). Current density in the cells transfected with $\gamma_{6446}$ was reduced significantly (19±4%; n=10; p<0.01) compared to control values (FIG. 37A, FIG. 38). This result shows that replacement of TM2 and TM3 of $\gamma_6$ with the homologous regions from $\gamma_4$ does not alter its ability to inhibit calcium current. It also indicates that the critical portion(s) of γ6 must be contained in the N- or C-terminal regions including TM1 and TM4 and their associated cytoplasmic tails.

To probe the importance of the terminal regions of $\gamma_6$, a series of chimeric γ proteins was designed in which the N- and C-terminal regions were targeted for substitution or truncation. The first set of chimeras was designed to determine whether either the N-terminal or the C-terminal region of $\gamma_6$ was sufficient for current inhibition or whether both regions were required simultaneously. The chimera $\gamma_{6444}$ was engineered using wild type $\gamma_4$ but with the N-terminal region substituted by the homologous region of $\gamma_6$. The substituted region contained the N-terminal cytoplasmic domain, TM1 and a portion of the extracellular region linking TM1 to TM2. The second chimera in this series, $\gamma_{4446}$, was also based on wild-type $\gamma_4$ but in this case TM4 and the C-terminal cytoplasmic domain from $\gamma_6$ were substituted into the protein. When expressed in the Cav3.1/HEK cells, $\gamma_{6444}$ decreased normalized current density to 46±7.6% (n=12, p<0.05) of control values obtained from cells transfected with $\gamma_4$ as a negative control (FIG. 37B, FIG. 38). The magnitude of this effect is similar to that seen for wild-type $\gamma_6$. In contrast, cells transfected with $\gamma_{4446}$ expressed calcium currents with densities similar to those obtained in controls (100%±15%, n=7, p>0.05) as was the case with wild type $\gamma_4$ (FIG. 38). These results indicate that the N-terminal region of $\gamma_6$, including the cytoplasmic region and TM1, is necessary for the inhibition of LVA calcium current.

To test this result and to rule out any effects of using the wild-type $\gamma_4$ as the backbone for construction of the chimeras, we engineered proteins using wild-type $\gamma_6$ into which TM1 and TM4 of γ4 were substituted for the homologous regions of $\gamma_6$ ($\gamma_{6664}$, $\gamma_{4666}$). In the case of the $\gamma_{6664}$ chimera, the construct contained the cytoplasmic C-terminal region as well as TM4 of $\gamma_4$. The $\gamma_{4666}$ construct contained the N-terminal cytoplasmic region, TM1 and part of the extracellular region linking Tm1 and TM2 from $\gamma_4$. Calcium current density in cells transfected with $\gamma_{4666}$ was not statistically different from controls (82+6%, n=9, P>0.05) (FIG. 38). In contrast, the calcium current density in cells transfected with $\gamma_{6664}$ was significantly reduced (37±5%, n=9, p<0.01) (FIG. 38). These results indicated that the N-terminal region of γ6 is critical for the inhibitory effect of this isoform on calcium current density.

To define more precisely what portion of the N-terminal region is responsible for this effect, we engineered additional $\gamma_6$ subunits that had portions of the N-terminal cytoplasmic domains removed. The construct $\gamma_{6L, N-trunc}$ had the first XXX amino acids deleted leaving a short (YY amino acid) cytoplasmic sequence before TM1. A similar construct, $\gamma_{6L, N-deleted}$ had the entire N-terminal cytoplasmic region up to TM1 deleted from the protein. Finally, $\gamma_{4.6666}$ had the N-terminal cytoplasmic domain of $\gamma_6$ replaced by the homologous region of $\gamma_4$. Expression of all of these constructs significantly decreased calcium current. The magnitude of the effect was 52±5% for $\gamma_{6L, N-trunc}$ (n=8, p<0.05), 22±3% for $\gamma_{6L, N-deleted}$ (n=10, p<0.01) and 29±5% for $\gamma_{4.6666}$ (n=10, p<0.01). These results show that the N-terminal cytoplasmic region of $\gamma_6$ is not necessary for the inhibitory effect of this isoform, since it can be removed or replaced with the homologous region of $\gamma_4$ without diminishing the effect compared to that of the wild-type.

One major difference between $\gamma_6$ and $\gamma_4$ is the presence of a C-terminal PDZ-binding domain in $\gamma_4$. To determine whether the PDZ-binding domain in $\gamma_4$ somehow prevented it from altering calcium current, we constructed a truncated form of $\gamma_4$ in which the C-terminal region was deleted ($\gamma_4$ C-trunc). It had no significant effect on calcium current indicating that differences in the C-terminal region between γ6 and γ4 do not explain the difference in their function (FIG. 38).

Taken together, these results demonstrate that TM1 of $\gamma_6$ is required for the inhibitory effect of this protein on Cav3.1 calcium current.

There are no presently observed effects of γ6 subunit chimeras on the biophysical properties of the Cav3.1 calcium current. We have previously shown that the effect of $\gamma_6$ on Cav3.1 calcium current is limited to decreasing current density with little change in the voltage dependency and kinetics of the currents. Our results indicate that the chimeric γ subunit proteins had little effect on the biophysical properties of the currents (FIG. 39). For instance, none of the chimeras or truncated forms studied had a significant effect on the voltage at which peak current occurred. In all but one case, no effects were seen on $V_{0.5}$ or k derived from the Boltzman curve used to fit the voltage dependency of activation. The exception was the $\gamma_{6L}$ N-del chimera in which the k of activation was shifted from a control value of 13.3±0.3 to 15.0±1.7 (p<0.05). Similarly, none of the transfected γ subunits or chimeras had a significant effect on $V_{0.5}$ or k of the voltage dependency of inactivation. There were no significant differences in the time to peak current, the time constant of inactivation, or the fast component of the time constant of inactivation for any chimera studied.

A GXXXA motif is required for inhibition of LVA calcium current by γ6. To identify specific residues or motifs within TM1 of $\gamma_6$ that are required for its functional effect we constructed $\gamma_6$ proteins with targeted amino acid substitutions. The first transmembrane domain of $\gamma_6$ is unique in that it contains two GXXXA motifs ($G^{42}XXXA^{46}$ and $G^{49}XXXA^{53}$) (FIG. 40). (G/A/S)XXX(G/A/S) motifs can enable helix-helix interactions between transmembrane helical domains within proteins. The presence of amino acids with small side chains located one helical turn along the helix axis may provide indentations that promote close association of adjacent helices. Since we have shown that a helical transmembrane domain is required for the functional effect of $\gamma_6$, it is reasonable to hypothesize that helix/helix interactions are a critical aspect of the molecular mechanism underlying its effects. We therefore focused our analysis on the two GXXXA motifs in TM1 of $\gamma_6$.

As an initial test to determine whether one or both of the GXXXA motifs within TM1 of $\gamma_6$ are, in fact, functionally significant, mutants were created in which the glycine (G) residues at positions 42 and 49 were replaced with either leucine (L, large side-chain) or alanine (A, small side-chain). The goal was to determine if the presence of small side chains was an obligatory feature of residues at these positions and whether substitution of residues with large side chains would eliminate the subunit's functional effect. When the G42A mutant was expressed, Cav3.1 current density decreased to 73.4%±8.9% (n=16) (p<0.05) compared to control, not significantly different to what is seen with co-expression of the wild type protein (FIG. 41A). In contrast, current density in cells expressing the G42L mutant was 107.5%±10.9% (n=19) compared with control indicating that the mutant protein had lost its inhibitory function. Thus an amino acid with a small side chain at position 42 appears to be necessary for the inhibitory activity of TM1 of $\gamma_6$. This result suggests that the first GXXXA motif ($G^{42}xxxA^{46}$) is required for the $\gamma_6$ protein to retain its function. To test this idea further we engineered the A46I mutant and found that it also altered Cav3.1 current density (FIG. 41). This result confirms that a small side chain residue is required at the A46 position and demonstrates that the complete $G^{42}XXXA^{46}$ motif is necessary for the $\gamma_6$ subunit to be effective in altering Cav3.1 calcium current density.

A similar set of substitutions was made at $G^{49}$ (FIG. 41). Both the G49A and G49L mutants caused a decrease in LVA calcium current density (67.6%±5.9%, n=36; and 73.1%±4.8%, n=22, respectively) indicating that the second GXXXA motif in $\gamma_6$ is not required for the ability of the subunit to decrease LVA current density.

Introduction of a GXXXA motif into γ1 makes it inhibitory for Cav3.1 current. Wild-type $\gamma_1$ does not alter calcium current density when co-expressed with Cav3.1 (FIG. 41 B) suggesting that the functional effect of $\gamma_1$ may be limited to HVA, L-type channels as shown by Campbell and colleagues. Unlike TM1 of $\gamma_6$, the first TM of γ1 contains only a single GXXXA motif ($G^{19}XXXA^{23}$) that corresponds with respect to its relative position within the helix to the second motif in $\gamma_6$ ($G^{49}XXXA^{53}$). We have demonstrated the second motif of $\gamma_6$ ($G^{49}XXXA^{53}$) is not necessary for the protein to alter LVA calcium current density (FIG. 40). Given the close homology of the $\gamma_1$ and $\gamma_6$ subunits we hypothesized that introducing a second GXXXA motif into TM1 of γ1 at the same position as the first (functional) motif in $\gamma_6$ would make $\gamma_1$ inhibitory when co-expressed with Cav3.1. To test this idea two $\gamma_1$ mutants were made. The first (T12G) contained just part of the GXXXA motif while the second, double mutant (T12G, I16A) contained the complete motif. When co-expressed with Cav3.1 the double mutant (12TG,I16A) significantly inhibited Cav3.1 current while the single mutant had, like wild type γ1, no effect (FIG. 41B). Thus introduction of a GXXXA motif at the appropriate position in TM1 of $\gamma_1$ imparts a new function to the $\gamma_1$ subunit (an ability to modulate Cav3.1 current) that is not seen in the wild-type protein. This result is consistent with our observation that the first GXXXA motif within TM1 of γ6 is the critical sequence that determines its functional effect on Cav3.1 calcium current.

Discussion.

The $\gamma_6$ subunit has a unique ability to reduce current density when co-expressed with the pore forming Cav3.1 α subunits. Using both chimeric proteins and site directed mutagenesis, we have now identified a specific GXXXA motif within $\gamma_6$ located near the cytoplasmic end of the first transmembrane domain of the protein that is required for this inhibitory effect. Our demonstration using co-immunoprecipitation that $\gamma_6$ forms stable complexes with Cav3.1 suggests that the function of the GXXXA motif is to promote helix/helix interactions between γ6 and Cav3.1.

While this is the first study designed to identify functional motifs in $\gamma_6$, Arikkath and colleagues investigated the ability of $\gamma_1$, the closest homologue of $\gamma_6$ within the γ subunit family, to reduce HVA calcium currents using $\gamma_1/\gamma_2$ chimeras. There is biochemical evidence supporting the existence of 65 $_1$/Cav1.1 complexes in native cells, and functional assays demonstrate a pronounced inhibitory effect of $\gamma_1$ on HVA calcium currents (Curtis and Catterall 1984; Flockerzi, Oeken et al. 1986; Freise, Held et al. 2000; Arikkath and Campbell 2003). $\gamma_2$, however, does not have any functional effect on Cav1.1. Arikkath and Campbell showed that a chimera containing the N-terminal half of $\gamma_1$ and the C-terminal half of 72 possessed the same functionality as the $\gamma_1$ subunit in both a heterologous expression system and in native $\gamma_1-/-$ mouse myotubes (Arikkath, Chen et al. 2003). However, chimeras containing the N-terminal half of $\gamma_2$ and the C-terminal half of $\gamma_1$, were not inhibitory. Our present studies have delineated that the critical functional domain is the TM1 structural segment; this is consistent with our data, e.g., on $\gamma_6$ and its effects on Cav3.1 current.

GXXXG and related motifs enhance transmembrane helix interactions in both soluble and membrane associated proteins (Senes et al 2004; Curran and Engelman, 2003; Russ and Engelman, 2000). The presence of amino acids with small side chains (G,A, or S) located three residues (one helical turn) apart creates on one helical face an area that permits close contact with a neighboring helix. This close association may then allow the formation of hydrogen bonds or van der Waals interactions (Kleiger and Eisenberg, 2002). While the presence of a GXXXG or related motif can promote helical interactions, the presence of suitable near neighbor residues may also be important, even necessary, for the formation of stable complexes. Senes, Gerstein and Engelman (2000) have shown that the GXXXG motif frequently occurs with neighboring β-branched residues (V, I, L) at adjoining positions (±1) and have proposed that they may be significant for helix/helix interactions or in modulating helix flexibility. Thus while the GXXXG or related motif creates an appropriate contact surface, side chain interactions can also be significant for determining the stability of any helix/helix associations (Schneider, 2004).

The GXXXA motifs found in TM1 of the $\gamma_6$ calcium channel subunits of rat, mouse and human conform to the classical description of these helical interaction domains (for sequence comparisons, see Chu, Roberston and Best, 2001). By definition, each contains two residues with small side chains separated by three intervening residues (GXXXA) and each motif is accompanied by residue(s) with β-branching side chain (for rat: $G^{42}XXV^{45}A^{46}I^{47}$; $G^{49}XXL^{52}A^{53}V^{54}$). In TM1 of human $\gamma_6$ the first motif becomes AXXLA while the second motif is identical to that of rat and mouse (GXXLAV). Thus there is a high degree of sequence conservation amongst species for these motifs in the $\gamma_6$ subunit. It is interesting that while TM1 of $\gamma_4$ does contain overlapping AXXXA and GXXXA motifs they are more centrally located and neither is associated with a residue with a β-branching side chain. Mechanistically, this difference may underly $\gamma_4$'s inability to bind robustly to Cav3.1 and to alter calcium current.

Despite being a close homologue of $\gamma_6$, the $\gamma_1$ subunit does not alter Cav3.1 calcium current in our heterologous expression system suggesting that the $\gamma_1$ and $\gamma_6$ subunits are capable of selectively targeting HVA and LVA channels. This selectivity can occur as follows. The $\gamma_6$ subunit contains two GXXXA motifs in TM1 while $\gamma_1$ contains only one. Only the GXXXA motif near the cytoplasmic end of $\gamma_6$ TM1 ($G^{42}XXXA^{46}$) is required for its inhibitory affect on Cav3.1. The GXXXA motif in TM1 of $\gamma_1$ is located near the extracellular end of the domain in a position homologous to the non-critical motif in $\gamma_6$. Thus we proposed a possible answer, that the position of the motif within TM1 determines the identity of its target. If this is correct then introduction of a second GXXXA motif into $\gamma_1$ near the cytoplasmic end of TM1 should allow it to inhibit Cav3.1 calcium current. This is exactly what we discovered with the $\gamma_1$ subunit containing the double mutation (12TG, I16A). A further prediction of our idea that it is the relative location of the GXXXA motif with TM1 that defines its target is that $\gamma_6$, since it has the motif in two locations, should be capable of inhibiting HVA, as well as LVA, calcium current.

While our coimmunoprecipitation experiments have demonstrated $\gamma_6$/Cav3.1 binding, the precise location of the interaction site on Cav3.1 is as yet unidentified. Nor is it certain how $\gamma_6$ and $\gamma_1$ binding alters calcium current. Since the major effect of these subunits is a decrease in current density with little or no effect on the voltage dependency or kinetics of the current, one likely mechanistic possibility is that the subunit reduces the number of functional channels in the plasma membrane. However, this remains to be verified. It is interesting that the subset of γ subunits that contain PDZ binding domains at their C-termini ($\gamma_2$, $\gamma_3$ $\gamma_4$, and $\gamma_8$, the TARP proteins) have been shown to regulate AMPA receptor trafficking (Vandenberghe, Nicoll et al. 2005). This effect is mediated by the PDZ binding domain. If $\gamma_1$ and $\gamma_6$ are shown to alter calcium channel trafficking then they must do so via a different mechanism.

Finally, when compared with other studies our results reinforce the idea that members of the calcium channel γ subunit family may perform multiple functions within cells. The proposed function of members of this family of proteins was originally defined by the properties of $\gamma_1$ which associates with and alters the properties of the HVA current in skeletal muscle. More recently the four isoforms containing PDZ binding domains ($\gamma_2$, $\gamma_3$ $\gamma_4$, and $\gamma_8$, the TARP proteins) have been shown to play major physiological roles as auxiliary subunits of AMPA receptors rather than as subunits of calcium channels. They are involved in transport, targeting and anchoring of AMPA receptors and may also modulate their biophysical properties (Osten and Stern-Bach, 2006). The $\gamma_2$ isoform has also been shown to modify cell aggregation. In contrast, while neither $\gamma_1$ nor $\gamma_6$ is known to alter AMPA receptor trafficking or function, both isoforms have been shown (by co-immunoprecipitation) to form complexes with $\alpha_1$ subunits of calcium channels and both dramatically alter calcium current density. Our results have identified in $\gamma_6$ an important sequence motif, lacking in the TARP proteins, that promotes interactions with Cav3.1.

We have surprisingly discovered that the introduction of the GxxxA motif in TM1 of a gamma subunit, not normally capable of decreasing calcium current, can confer to such non-functional isoform the ability to inhibit calcium current. The positioning of the motif can influence the ability to modulate calcium current at more than one level of control. In one aspect, the positioning can result in functionality at all or the lack thereof. In another aspect, the positioning can determine selectivity for regulation of a high voltage gated channel and/or a low voltage gated channel. For example, locating a motif towards an extracellular side of a transmembrane segment can allow selectivity of a high voltage gated channel whereas locating a motif towards a cytoplasmic side can allow selectivity of regulation of a low voltage gated channel.

Figure Descriptions in Example 6

FIG. 36. $\gamma_6$ co-immunoprecipitates with Cav3.1. (A) HEK/Cav3.1 cells were transfected with plasmids containing either Flag tagged $\gamma_6$ or Flag-tagged $\gamma_4$. After transfection (24 h), cells were lysed and immunoprecipitated (IP) with anti-Flag M2 beads. Western blot analysis was performed with anti-$Ca_v3.1$ and anti-Flag antibodies. (B) The bar graph represents a quantification of Cav3.1 in the immunoprecipitates normalized to total Flag$\gamma_4$ or Flag$\gamma_6$ levels from three independent experiments. Binding of $\gamma_6$ to Cav3.1 is robust compared to relatively weak binding of $\gamma_4$.

(See FIG. 10.) Schematic representations of chimeric and truncated γ subunits used in this study. Chimeric γ subunits were engineered to identify specific regions within the $\gamma_6$ subunit that are required for its ability to reduce Cav3.1 calcium current density. Note that the $\gamma_4$ subunit has no functional effect on Cav3.1 current density. Truncated subunits were used to probe the importance of C and N terminal cytoplasmic regions.

FIG. 37. The N-terminal region of $\gamma_6$ is required for its inhibitory effect on Cav3.1 calcium current density. Representational Cav3.1 current traces and I/V curves demonstrating the effects of transiently transfecting Cav3.1/HEK cells with plasmids expressing: (A) $\gamma_4$ (B) $\gamma_{6L}$ (C) $\gamma_{6446}$ and (D) $\gamma_{6444}$. (E) and (F) Normalized current voltage curves. The $\gamma_4$ subunit does not affect Cav3.1 calcium current and these traces represent negative controls. They are equivalent to currents recorded from untransfected Cav3.1/HEK cells. The chimeric proteins $\gamma_{6446}$ and $\gamma_{6444}$ decrease calcium current to an extent similar to that seen with the wild-type $\gamma_6$. These results indicate that the N-terminal region of $\gamma_6$ contains critical sequences that are involved in modulation of Cav3.1 current by $\gamma_6$.

FIG. 38. Average effects on Cav3.1 calcium current density of the wild type y subunits ($\gamma_{6L}$, $\gamma_{6S}$, $\gamma_4$) compared to all chimeras and truncated peptides studied. A comparison of the effects of the engineered peptides with those of the wild-type indicate that any peptide containing TM1 of $\gamma_6$ decreases Cav3.1 current density.

FIG. 39. Wild type and chimeric γ subunits do not affect the voltage dependency and kinetics of Cav3.1 current. (A) Voltage dependency of activation (B) Voltage dependency of inactivation (C) Time to peak current (D) τ of inactivation (E) τ fast of deactivation (F) τ slow of deactivation.

FIG. 40. TM1 of γ6 contains unique GXXXA motifs Top: Sequence alignments of TM1 of $\gamma_6$, $\gamma_4$ and $\gamma_1$. TM1 of $\gamma_6$ contains two unique GXXXA motifs starting at positions 42G and 49G. TM1 of $\gamma_1$ contains only a single GXXXA motif starting at position G19. The residues mutated in the study are circled. Bottom: Space filling model of the same sequences (G in dark blue, A in ice blue) illustrating the groove formed by the small side chains along one face of the helix in $\gamma_6$.

FIG. 41. The first GXXXA motif in TM1 of $\gamma_6$ is necessary for the effect of the subunit on Cav3.1 current density. (A) Normalized, averaged data showing the effects of various point mutations on the ability of $\gamma_6$ to decrease Cav3.1 current. Substitution of residues with large side chains at positions G42, and A46 remove the ability of the subunit to alter current. (B) Introduction of a GXXXA motif into TM1 of $\gamma_1$ gives it the ability to decrease Cav3.1 calcium current.

STATEMENTS REGARDING INCORPORATION BY REFERENCE AND VARIATIONS

All references throughout this application, for example patent documents including issued or granted patents or equivalents; patent application publications; unpublished patent applications; and non-patent literature documents or other source material; are hereby incorporated by reference herein in their entireties, as though individually incorporated by reference, to the extent each reference is at least partially not inconsistent with the disclosure in this application (for example, a reference that is partially inconsistent is incorporated by reference except for the partially inconsistent portion of the reference).

Any appendix or appendices hereto are incorporated by reference as part of the specification and/or drawings.

Where the terms "comprise", "comprises", "comprised", or "comprising" are used herein, they are to be interpreted as specifying the presence of the stated features, integers, steps, or components referred to, but not to preclude the presence or addition of one or more other feature, integer, step, component, or group thereof. Separate embodiments of the invention are also intended to be encompassed wherein the terms "comprising" or "comprise(s)" or "comprised" are optionally replaced with the terms, analogous in grammar, e.g.; "consisting/consist(s)" or "consisting essentially of/consist(s) essentially of" to thereby describe further embodiments that are not necessarily coextensive.

The invention has been described with reference to various specific and preferred embodiments and techniques. However, it should be understood that many variations and modifications may be made while remaining within the spirit and scope of the invention. It will be apparent to one of ordinary skill in the art that compositions, methods, devices, device elements, materials, procedures and techniques other than those specifically described herein can be applied to the practice of the invention as broadly disclosed herein without resort to undue experimentation. All art-known functional equivalents of compositions, methods, devices, device elements, materials, procedures and techniques described herein are intended to be encompassed by this invention. Whenever a range is disclosed, all subranges and individual values are intended to be encompassed as if separately set forth. This invention is not to be limited by the embodiments disclosed, including any shown in the drawings or exemplified in the specification, which are given by way of example or illustration and not of limitation. The scope of the invention shall be limited only by the claims.

REFERENCES

U.S. Pat. Nos. 5,364,842; 5,795,864; 6,949,554; 6,943,168; 6,617,322; 6,492,375; 6,387,897; 6,310,059; 6,267,945; 6,011,035.

US Patent Application Publication Nos. 20050014748; 20040044004; 20040034035.

Arikkath, J. and K. P. Campbell (2003). "Auxiliary subunits: essential components of the voltage-gated calcium channel complex." Curr Opin Neurobiol 13(3): 298-307.

Arikkath, J., C. C. Chen, et al. (2003). "Gamma 1 subunit interactions within the skeletal muscle L-type voltage-gated calcium channels." J Biol Chem 278(2): 1212-9.

Chu, P. J., H. M. Robertson, et al. (2001). "Calcium channel gamma subunits provide insights into the evolution of this gene family." Gene 280(1-2): 37-48.

Curtis, B. M. and W. A. Catterall (1984). "Purification of the calcium antagonist receptor of the voltage-sensitive calcium channel from skeletal muscle transverse tubules." Biochemistry 23(10): 2113-8.

Eberst, R., S. Dai, et al. (1997). "Identification and functional characterization of a calcium channel gamma subunit." Pflugers Arch 433(5): 633-7.

Flockerzi, V., H. J. Oeken, et al. (1986). "Purified dihydropyridine-binding site from skeletal muscle t-tubules is a functional calcium channel." Nature 323(6083): 66-8.

Freise, D., B. Held, et al. (2000). "Absence of the gamma subunit of the skeletal muscle dihydropyridine receptor increases L-type Ca2+ currents and alters channel inactivation properties." J Biol Chem 275(19): 14476-81.

Freise, D., B. Held, et al. (Biol Chem 2000 May 12). "Absence of the gamma subunit of the skeletal muscle dihydropyridine receptor increases L-type Ca2+ currents and alters channel inactivation properties." J 275(19): 14476-81.

Green, P. (2001). "Kinetic modification of the alpha1 I subunit-mediated T-type Ca2+ channel by a human neuronal Ca2+ channel gamma subunit." Journal of Physiology 533.2: 467-478.

Held, B., D. Freise, et al. (2002). "Skeletal muscle L-type Ca(2+) current modulation in gamma1-deficient and wild-type murine myotubes by the gamma1 subunit and cAMP." J Physiol 539(Pt 2): 459-68.

Kang, M. G., C. C. Chen, et al. (2001). "Biochemical and biophysical evidence for gamma 2 subunit association with neuronal voltage-activated Ca2+ channels." J Biol Chem 276 (35): 32917-24.

Klugbauer, N., S. Dai, et al. (2000). "A family of gamma-like calcium channel subunits." Febs 470(2): 189-97.

Lacinova, L. and N. Klugbauer (2004). "Modulation of gating currents of the Ca(v)3.1 calcium channel by alpha 2 delta 2 and gamma 5 subunits." Arch Biochem Biophys 425 (2): 207-13.

Letts, V. A., R. Felix, et al. (1998). "The mouse stargazer gene encodes a neuronal Ca2+-channel gamma subunit [see comments]." Nat Genet 19(4): 340-7.

Li, Y., N. Gamper, et al. (2004). "Single-channel analysis of KCNQ K+ channels reveals the mechanism of augmentation by a cysteine-modifying reagent." J Neurosci 24(22): 5079-90.

Moss, F. J., P. Viard, et al. (2002). "The novel product of a five-exon stargazin-related gene abolishes Ca(V)2.2 calcium channel expression." Embo J 21(7): 1514-23.

Njue, A. I., J. Hayashi, et al. (2004). "Mutations in the extracellular domains of glutamate-gated chloride channel alpha3 and beta subunits from ivermectin-resistant *Cooperia oncophora* affect agonist sensitivity." J Neurochem 89(5): 1137-47.

Singer, D., M. Biel, et al. (1991). "The roles of the subunits in the function of the calcium channel." Science 253(5027): 1553-7.

Tomita, S., L. Chen, et al. (2003). "Functional studies and distribution define a family of transmembrane AMPA receptor regulatory proteins." J Cell Biol 161(4): 805-16.

Wagner, D. A., C. Czajkowski, et al. (2004). "An arginine involved in GABA binding and unbinding but not gating of the GABA(A) receptor." J Neurosci 24(11): 2733-41.

Hansen J P et al., 2004, Calcium channel γ6 subunits are unique modulators of low voltage-activated (Cav3.1) calcium current. Journal of Molecular and Cellular Cardiology 37:1147-1158.

Schneider and Engelman, 2004.

Kobus and Fleming, 2005.

The invention claimed is:

1. An isolated calcium channel gamma6 subunit peptide fragment comprising an N-terminal first transmembrane domain segment of at least 15 continuous amino acids of a rat, mouse, or human source; wherein the peptide fragment has a maximum total length of 15 to 40 amino acids, and wherein the segment comprises a $Gx_2x_3x_4G$-like structural motif located near the cytoplasmic end of the first transmembrane domain, wherein the $Gx_2x_3x_4G$-like motif is a $x_1x_2x_3x_4x_5$ in which $x_1$ and $x_5$ are each independently glycine or alanine or serine and wherein $x_2$, $x_3$, and $x_4$ are each independently selected from leucine, valine, phenylalanine, glycine, threonine, isoleucine, alanine and serine, and wherein said peptide fragment can reduce voltage dependent calcium current in a cell.

2. The peptide fragment of claim 1 having a maximum total length of 15 amino acids.

3. The peptide fragment of claim 1 having a maximum total length of about 20 amino acids.

4. The peptide fragment of claim 1 having a homology level of at least 90% to the N-terminal first transmembrane domain segment of a gamma6 ($\gamma_6$) subunit amino acid sequence from a human source.

5. The peptide fragment of claim 1 having a homology level of at least 90% to the N-terminal first transmembrane domain segment of a $\gamma_6$ subunit amino acid sequence from a rat source.

6. The peptide fragment of claim 1 having a homology level of at least 90% to the N-terminal first transmembrane domain segment of a $\gamma_6$ subunit amino acid sequence from a mouse source.

7. The peptide fragment of claim 1 wherein $x_1$ and $x_5$ are glycine and alanine respectively.

8. The peptide fragment of claim 1 wherein X1 is glycine.

9. The peptide fragment of claim 1 having a structural groove along at least a portion of a three-dimensional projection of a helical face of the first transmembrane domain of the peptide.

10. A method of modifying an ability of a calcium channel to regulate calcium in a cell, comprising exposing said cell to the calcium channel gamma6 subunit peptide fragment of claim 1.

11. A method of decreasing calcium current in a cell, comprising exposing said cell to the calcium channel gamma6 subunit peptide fragment of claim 1.

12. The method of claim 11, wherein said exposing step comprises recombinantly expressing said peptide fragment within said cell.

13. The peptide fragment of claim 1 wherein the N-terminal first transmembrane domain segment has the sequence of SEQ ID NO: 12 or a sequence at least 90% homologous to SEQ ID NO: 12.

14. The peptide fragment of claim 1 having a homology level of at least 90% to the N-terminal first transmembrane domain segment of a gamma6 subunit amino acid sequence from a human, rat, or mouse source.

* * * * *